US012749571B2

(12) United States Patent
Arrizza et al.

(10) Patent No.: US 12,749,571 B2
(45) Date of Patent: Sep. 29, 2026

(54) MEDICAL DEVICE UPDATE SYSTEM

(71) Applicant: ICU Medical, Inc., San Clemente, CA (US)

(72) Inventors: John Arrizza, Oceanside, CA (US); James R. Shults, Ramona, CA (US); Thomas J. Vaccaro, Encinitas, CA (US); Patrick A. Ward, San Diego, CA (US)

(73) Assignee: ICU Medical, Inc., San Clemente, CA (US)

(*) Notice: Subject to any disclaimer, the term of this patent is extended or adjusted under 35 U.S.C. 154(b) by 0 days.

(21) Appl. No.: 19/452,118

(22) Filed: Jan. 16, 2026

(65) Prior Publication Data

US 2026/0142025 A1 May 21, 2026

Related U.S. Application Data

(63) Continuation of application No. 19/267,385, filed on Jul. 11, 2025, which is a continuation of application
(Continued)

(51) Int. Cl.
*G16H 40/40* (2018.01)
*A61M 5/142* (2006.01)
(Continued)

(52) U.S. Cl.
CPC ............ *G16H 40/40* (2018.01); *A61M 5/142* (2013.01); *G06F 8/65* (2013.01); *G16H 20/17* (2018.01);
(Continued)

(58) Field of Classification Search
CPC ................................................... G06F 8/60–66
(Continued)

(56) References Cited

U.S. PATENT DOCUMENTS

| | | | |
|---|---|---|---|
| 4,024,864 | A | 5/1977 | Davies et al. |
| 4,055,175 | A | 10/1977 | Clemens et al. |

(Continued)

FOREIGN PATENT DOCUMENTS

| | | |
|---|---|---|
| AU | 2004226440 | 10/2004 |
| AU | 2004305087 | 7/2005 |

(Continued)

OTHER PUBLICATIONS

Siv-Lee, Lor, et al., Implementation of Wireless "Intelligent" Pump IV Infusion Technology in a Not-for-Profit Academic Hospital Setting, Hospital Pharmacy, vol. 42, No. 9, 9 pages, 2007, [retrieved on Mar. 24, 2026], Retrieved from the Internet: <URL:https://journals.sagepub.com/doi/full/10.1310/hpj4209-832>.*
(Continued)

*Primary Examiner* — Geoffrey R St Leger
(74) *Attorney, Agent, or Firm* — Knobbe, Martens Olson & Bear, LLP

(57) ABSTRACT

A system and method for providing updates to medical devices is disclosed. In one example, the medical devices are configured to pull update files in response to the reception of an update message from a server. Once the update files are downloaded by a medical device, the update files can be installed. While the medical device pulls the update files, the medical device can continue with its normal operation. If desired, a user can select which medical devices should be updated, based on any desired factors, such as the physical location of the device, the model of the device, the type of device, and the way the device is being used.

21 Claims, 16 Drawing Sheets

Related U.S. Application Data

No. 18/651,439, filed on Apr. 30, 2024, now Pat. No. 12,380,997, which is a continuation of application No. 17/655,981, filed on Mar. 22, 2022, now Pat. No. 11,996,188, which is a continuation of application No. 15/435,230, filed on Feb. 16, 2017, now Pat. No. 11,626,205, which is a continuation of application No. 13/655,690, filed on Oct. 19, 2012, now Pat. No. 9,594,875.

(60) Provisional application No. 61/549,826, filed on Oct. 21, 2011.

(51) Int. Cl.
*G06F 8/61* (2018.01)
*G06F 8/65* (2018.01)
*G16H 20/17* (2018.01)
*G16H 70/40* (2018.01)

(52) U.S. Cl.
CPC ......... *G16H 70/40* (2018.01); *A61M 5/14212* (2013.01); *A61M 2205/3561* (2013.01); *G06F 8/61* (2013.01)

(58) Field of Classification Search
USPC .................................................. 717/168–178
See application file for complete search history.

(56) References Cited

U.S. PATENT DOCUMENTS 4,151,845 A 5/1979 Clemens
4,213,454 A 7/1980 Shim
4,240,438 A 12/1980 Updike et al.
4,280,494 A 7/1981 Cosgrove et al.
4,308,866 A 1/1982 Jeliffe
4,370,983 A 2/1983 Lichtenstein et al.
4,373,527 A 2/1983 Fischell
4,392,849 A 7/1983 Petre et al.
4,395,259 A 7/1983 Prestele et al.
4,457,751 A 7/1984 Rodler
4,464,170 A 8/1984 Clemens
4,469,481 A 9/1984 Kobayashi
4,475,901 A 10/1984 Kraegen et al.
4,494,950 A 1/1985 Fischell
4,498,843 A 2/1985 Schneider et al.
4,515,584 A 5/1985 Abe et al.
4,526,568 A 7/1985 Clemens et al.
4,529,401 A 7/1985 Leslie et al.
4,543,955 A 10/1985 Schroeppel
4,551,133 A 11/1985 Zegers de Beyl et al.
4,553,958 A 11/1985 LeCocq
4,559,037 A 12/1985 Franetzki et al.
4,613,937 A 9/1986 Batty
4,624,661 A 11/1986 Arimond
4,633,878 A 1/1987 Bombardieri
4,634,426 A 1/1987 Kamen
4,634,427 A 1/1987 Hannula et al.
4,674,652 A 6/1987 Aten et al.
4,676,776 A 6/1987 Howson et al.
4,679,562 A 7/1987 Luksha
4,685,903 A 8/1987 Cable et al.
4,695,954 A 9/1987 Rose
4,696,671 A 9/1987 Epstein et al.
4,714,462 A 12/1987 DiDomenico
4,722,734 A 2/1988 Kolin
4,730,849 A 3/1988 Siegel
4,731,051 A 3/1988 Fischell
4,741,732 A 5/1988 Crankshaw et al.
4,756,706 A 7/1988 Kerns et al.
4,776,842 A 10/1988 Franetzki et al.
4,785,969 A 11/1988 Mclaughlin
4,803,625 A 2/1989 Fu et al.
4,835,372 A 5/1989 Gombrich et al.
4,838,275 A 6/1989 Lee
4,838,856 A 6/1989 Mulreany et al.
4,838,857 A 6/1989 Strowe et al.
4,854,324 A 8/1989 Hirschman et al.
4,857,716 A 8/1989 Gombrich et al.
4,858,154 A 8/1989 Anderson et al.
4,898,578 A 2/1990 Rubalcaba, Jr.
4,908,017 A 3/1990 Howson et al.
4,933,873 A 6/1990 Kaufman et al.
4,943,279 A 7/1990 Samiotes et al.
4,946,439 A 8/1990 Eggers
4,953,745 A 9/1990 Rowlett
4,978,335 A 12/1990 Arthur, III
5,000,739 A 3/1991 Kulisz et al.
5,010,473 A 4/1991 Jacobs
5,014,698 A 5/1991 Cohen
5,016,172 A 5/1991 Dessertine
5,026,084 A 6/1991 Paisfield
5,034,004 A 7/1991 Crankshaw
5,041,086 A 8/1991 Koenig et al.
5,058,161 A 10/1991 Weiss
5,078,683 A 1/1992 Sancoff et al.
5,084,828 A 1/1992 Kaufman et al.
5,088,981 A 2/1992 Howson et al.
5,097,505 A 3/1992 Weiss
5,100,380 A 3/1992 Epstein et al.
5,102,392 A 4/1992 Sakai et al.
5,104,374 A 4/1992 Bishko et al.
5,109,850 A 5/1992 Blanco et al.
5,131,816 A 7/1992 Brown
5,142,484 A 8/1992 Kaufman et al.
5,153,827 A 10/1992 Coutre et al.
5,157,640 A 10/1992 Backner
5,161,222 A 11/1992 Montejo et al.
5,177,993 A 1/1993 Beckman et al.
5,181,910 A 1/1993 Scanlon
5,190,522 A 3/1993 Wocicki et al.
5,199,439 A 4/1993 Zimmerman et al.
5,200,891 A 4/1993 Kehr et al.
5,216,597 A 6/1993 Beckers
5,221,268 A 6/1993 Barton et al.
5,230,061 A 7/1993 Welch
5,243,982 A 9/1993 Möstl et al.
5,244,463 A 9/1993 Cordner, Jr. et al.
5,249,260 A 9/1993 Nigawara et al.
5,254,096 A 10/1993 Rondelet et al.
5,256,156 A 10/1993 Kern et al.
5,256,157 A 10/1993 Samiotes et al.
5,261,702 A 11/1993 Mayfield
5,317,506 A 5/1994 Coutre et al.
5,319,355 A 6/1994 Russek
5,319,363 A 6/1994 Welch et al.
5,330,634 A 7/1994 Wong et al.
5,338,157 A 8/1994 Blomquist
5,341,476 A 8/1994 Lowell
5,364,346 A 11/1994 Schrezenmeir
5,366,346 A 11/1994 Danby
5,368,562 A 11/1994 Blomquist et al.
5,373,454 A 12/1994 Kanda et al.
5,376,070 A 12/1994 Purvis et al.
5,378,231 A 1/1995 Johnson et al.
5,389,071 A 2/1995 Kawahara et al.
5,389,078 A 2/1995 Zalesky et al.
5,417,222 A 5/1995 Dempsey et al.
5,423,748 A 6/1995 Uhala
5,429,602 A 7/1995 Hauser
5,431,627 A 7/1995 Pastrone et al.
5,432,777 A 7/1995 Le Boudec et al.
5,445,621 A 8/1995 Poli et al.
5,447,164 A 9/1995 Shaya et al.
5,455,851 A 10/1995 Chaco et al.
5,461,365 A 10/1995 Schlager et al.
5,464,392 A 11/1995 Epstein et al.
5,465,082 A 11/1995 Chaco
5,485,408 A 1/1996 Blomquist
5,486,286 A 1/1996 Peterson et al.
5,493,430 A 2/1996 Lu et al.
5,496,273 A 3/1996 Pastrone et al.
5,505,828 A 4/1996 Wong et al.

(56) References Cited

U.S. PATENT DOCUMENTS 5,507,288 A 4/1996 Bocker et al.
5,507,786 A 4/1996 Morgan et al.
5,508,499 A 4/1996 Ferrario
5,515,713 A 5/1996 Saugues et al.
5,520,637 A 5/1996 Pager et al.
5,522,798 A 6/1996 Johnson et al.
5,547,470 A 8/1996 Johnson et al.
5,554,013 A 9/1996 Owens et al.
5,562,615 A 10/1996 Nassif
5,577,169 A 11/1996 Prezioso
5,582,323 A 12/1996 Kurtenbach
5,582,593 A 12/1996 Hultman
5,594,786 A 1/1997 Chaco et al.
5,598,519 A 1/1997 Narayanan
5,620,608 A 4/1997 Rosa et al.
5,630,710 A 5/1997 Tune et al.
5,636,044 A 6/1997 Yuan et al.
5,643,212 A 7/1997 Coutre et al.
5,651,775 A 7/1997 Walker et al.
5,658,131 A 8/1997 Aoki et al.
5,658,250 A 8/1997 Blomquist et al.
5,665,065 A 9/1997 Colman et al.
5,669,877 A 9/1997 Blomquist
5,672,154 A 9/1997 Sillén et al.
5,681,285 A 10/1997 Ford et al.
5,685,844 A 11/1997 Marttila
5,687,717 A 11/1997 Halpern et al.
5,689,229 A 11/1997 Chaco et al.
5,697,899 A 12/1997 Hillman et al.
5,699,509 A 12/1997 Gary et al.
5,708,714 A 1/1998 Lopez et al.
5,713,350 A 2/1998 Yokota et al.
5,713,856 A 2/1998 Eggers et al.
5,718,562 A 2/1998 Lawless et al.
5,719,761 A 2/1998 Gatti et al.
5,733,259 A 3/1998 Valcke et al.
5,738,102 A 4/1998 Lemelson
5,744,027 A 4/1998 Connell et al.
5,752,621 A 5/1998 Passamante
5,754,111 A 5/1998 Garcia
5,764,034 A 6/1998 Bowman et al.
5,764,159 A 6/1998 Neftel et al.
5,772,635 A 6/1998 Dastur et al.
5,774,865 A 6/1998 Glynn
5,778,256 A 7/1998 Darbee
5,778,345 A 7/1998 McCartney
5,781,442 A 7/1998 Engleson et al.
5,782,805 A 7/1998 Meinzer et al.
5,788,669 A 8/1998 Peterson
5,797,515 A 8/1998 Liff et al.
5,800,387 A 9/1998 Duffy et al.
5,814,015 A 9/1998 Gargano et al.
5,822,544 A 10/1998 Chaco et al.
5,822,715 A 10/1998 Worthington et al.
5,827,179 A 10/1998 Lichter et al.
5,832,448 A 11/1998 Brown
5,836,910 A 11/1998 Duffy et al.
5,850,344 A 12/1998 Conkright
5,867,821 A 2/1999 Ballantyne et al.
5,870,733 A 2/1999 Bass et al.
5,871,465 A 2/1999 Vasko
5,873,731 A 2/1999 Predergast
5,885,245 A 3/1999 Lynch et al.
5,897,493 A 4/1999 Brown
5,897,498 A 4/1999 Canfield, II et al.
5,910,252 A 6/1999 Truitt et al.
5,912,818 A 6/1999 McGrady et al.
5,915,240 A 6/1999 Karpf
5,920,054 A 7/1999 Uber, III
5,920,263 A 7/1999 Huttenhoff et al.
5,924,074 A 7/1999 Evans
5,931,764 A 8/1999 Freeman et al.
5,935,099 A 8/1999 Peterson et al.
5,935,106 A 8/1999 Olsen
5,941,846 A 8/1999 Duffy et al.
5,956,501 A 9/1999 Brown
5,957,885 A 9/1999 Bollish et al.
5,960,085 A 9/1999 de la Huerga
5,961,448 A 10/1999 Swenson et al.
5,967,559 A 10/1999 Abramowitz
5,971,594 A 10/1999 Sahai et al.
5,975,081 A 11/1999 Hood et al.
5,990,838 A 11/1999 Burns et al.
5,997,476 A 12/1999 Brown
6,000,828 A 12/1999 Leet
6,003,006 A 12/1999 Colella et al.
6,012,034 A 1/2000 Hamparian et al.
6,017,318 A 1/2000 Gauthier et al.
6,021,392 A 2/2000 Lester et al.
6,024,539 A 2/2000 Blomquist
6,024,699 A 2/2000 Surwit et al.
6,032,155 A 2/2000 de la Huerga
6,032,676 A 3/2000 Moore
6,039,251 A 3/2000 Holowko et al.
6,070,761 A 6/2000 Bloom et al.
6,073,106 A 6/2000 Rozen et al.
6,104,295 A 8/2000 Gaisser et al.
6,112,182 A 8/2000 Akers et al.
6,112,323 A 8/2000 Meizlik et al.
RE36,871 E 9/2000 Epstein et al.
6,115,365 A 9/2000 Newberg
6,115,390 A 9/2000 Chuah
6,122,536 A 9/2000 Sun et al.
6,126,637 A 10/2000 Kriesel et al.
6,135,949 A 10/2000 Russo et al.
6,150,942 A 11/2000 O'Brien
6,151,643 A 11/2000 Cheng et al.
6,157,914 A 12/2000 Seto et al.
6,159,147 A 12/2000 Lichter et al.
6,167,567 A 12/2000 Chiles et al.
6,182,667 B1 2/2001 Hanks et al.
6,189,105 B1 2/2001 Lopes
6,195,589 B1 2/2001 Ketcham
6,208,974 B1 3/2001 Campbell et al.
6,222,323 B1 4/2001 Yamashita et al.
6,223,440 B1 5/2001 Rashman
6,226,277 B1 5/2001 Chuah
6,227,371 B1 5/2001 Song
6,234,176 B1 5/2001 Domae et al.
6,241,704 B1 6/2001 Peterson et al.
6,248,067 B1 6/2001 Causey, III et al.
6,249,705 B1 6/2001 Snell
6,257,265 B1 7/2001 Brunner et al.
6,259,355 B1 7/2001 Chaco et al.
6,269,340 B1 7/2001 Ford et al.
6,270,455 B1 8/2001 Brown
6,271,813 B1 8/2001 Palalau
6,277,072 B1 8/2001 Bardy
6,280,380 B1 8/2001 Bardy
6,283,761 B1 9/2001 Joao
6,285,665 B1 9/2001 Chuah
6,292,860 B1 9/2001 Cochcroft, Jr.
6,312,378 B1 11/2001 Bardy
6,327,254 B1 12/2001 Chuah
6,330,008 B1 12/2001 Razdow et al.
6,339,718 B1 1/2002 Zatezalo et al.
6,346,886 B1 2/2002 de la Huerga
6,363,282 B1 3/2002 Nichols et al.
6,371,719 B1 4/2002 Hildebrandt
6,377,548 B1 4/2002 Chuah
6,388,951 B1 5/2002 Matsumoto et al.
6,406,426 B1 6/2002 Reuss et al.
6,408,330 B1 6/2002 de la Huerga
6,418,334 B1 7/2002 Unger et al.
6,427,088 B1 7/2002 Bowman et al.
6,428,483 B1 8/2002 Carlebach
6,442,432 B2 8/2002 Lee
6,469,991 B1 10/2002 Chuah
6,475,180 B2 11/2002 Peterson et al.
6,482,158 B2 11/2002 Mault
6,485,418 B2 11/2002 Yasushi et al.
6,494,694 B2 12/2002 Lawless et al.
6,494,831 B1 12/2002 Koritzinsky
6,497,680 B1 12/2002 Holst et al.

(56) References Cited

U.S. PATENT DOCUMENTS

| | | | |
|---|---|---|---|
| 6,514,460 | B1 | 2/2003 | Fendrock |
| 6,517,482 | B1 | 2/2003 | Eiden et al. |
| 6,519,569 | B1 | 2/2003 | White et al. |
| 6,520,930 | B2 | 2/2003 | Critchlow et al. |
| 6,540,672 | B1 | 4/2003 | Simonsen et al. |
| 6,542,902 | B2 | 4/2003 | Dulong et al. |
| 6,544,212 | B2 | 4/2003 | Galley et al. |
| 6,544,228 | B1 | 4/2003 | Heitmeier |
| 6,546,350 | B1 | 4/2003 | Hartmann et al. |
| 6,551,276 | B1 | 4/2003 | Mann et al. |
| 6,554,798 | B1 | 4/2003 | Mann et al. |
| 6,558,320 | B1 | 5/2003 | Causey et al. |
| 6,558,351 | B1 | 5/2003 | Steil et al. |
| 6,565,509 | B1 | 5/2003 | Say et al. |
| 6,567,416 | B1 | 5/2003 | Chuah |
| 6,571,294 | B2 | 5/2003 | Simmon et al. |
| 6,572,542 | B1 | 6/2003 | Houben et al. |
| 6,572,545 | B2 | 6/2003 | Knobbe et al. |
| 6,578,002 | B1 | 6/2003 | Derzay et al. |
| 6,581,117 | B1 | 6/2003 | Klein et al. |
| 6,587,034 | B1 | 7/2003 | Heiman et al. |
| 6,589,229 | B1 | 7/2003 | Connelly et al. |
| 6,599,281 | B1 | 7/2003 | Struys et al. |
| 6,602,191 | B2 | 8/2003 | Quy |
| 6,605,072 | B2 | 8/2003 | Struys et al. |
| 6,628,809 | B1 | 9/2003 | Rowe et al. |
| 6,631,353 | B1 | 10/2003 | Davis et al. |
| 6,640,246 | B1 | 10/2003 | Gardy, Jr. et al. |
| 6,641,533 | B2 | 11/2003 | Causey, III et al. |
| 6,647,299 | B2 | 11/2003 | Bourget |
| 6,652,455 | B1 | 11/2003 | Kocher |
| 6,653,937 | B2 | 11/2003 | Nelson et al. |
| 6,659,947 | B1 | 12/2003 | Carter et al. |
| 6,669,630 | B1 | 12/2003 | Joliat et al. |
| 6,671,563 | B1 | 12/2003 | Engleson et al. |
| 6,673,033 | B1 | 1/2004 | Sciulli et al. |
| 6,674,403 | B2 | 1/2004 | Gray et al. |
| 6,681,003 | B2 | 1/2004 | Linder et al. |
| 6,689,091 | B2 | 2/2004 | Bui et al. |
| 6,692,241 | B2 | 2/2004 | Watanabe et al. |
| 6,694,191 | B2 | 2/2004 | Starkweather et al. |
| 6,694,334 | B2 | 2/2004 | DuLong et al. |
| 6,721,286 | B1 | 4/2004 | Williams et al. |
| 6,721,582 | B2 | 4/2004 | Trepagnier et al. |
| 6,725,200 | B1 | 4/2004 | Rost |
| 6,731,989 | B2 | 5/2004 | Engleson et al. |
| 6,740,072 | B2 | 5/2004 | Starkweather et al. |
| 6,751,651 | B2 | 6/2004 | Crockett |
| 6,752,787 | B1 | 6/2004 | Causey, III et al. |
| 6,753,830 | B2 | 6/2004 | Gelbman |
| 6,758,810 | B2 | 7/2004 | Lebel et al. |
| 6,773,396 | B2 | 8/2004 | Flach et al. |
| 6,774,786 | B1 | 8/2004 | Havekost et al. |
| 6,775,577 | B2 | 8/2004 | Cmkovich et al. |
| 6,780,156 | B2 | 8/2004 | Haueter et al. |
| 6,790,198 | B1 | 9/2004 | White et al. |
| 6,792,470 | B2 | 9/2004 | Hakenberg et al. |
| 6,796,956 | B2 | 9/2004 | Hartlaub et al. |
| 6,799,149 | B2 | 9/2004 | Hartlaub |
| 6,809,653 | B1 | 10/2004 | Mann et al. |
| 6,811,534 | B2 | 11/2004 | Bowman, IV et al. |
| 6,816,605 | B2 | 11/2004 | Rowe et al. |
| 6,839,753 | B2 | 1/2005 | Biondi et al. |
| 6,852,104 | B2 | 2/2005 | Blomquist |
| 6,859,134 | B1 | 2/2005 | Heiman et al. |
| 6,871,211 | B2 | 3/2005 | Labounty et al. |
| 6,873,268 | B2 | 3/2005 | Lebel et al. |
| 6,876,303 | B2 | 4/2005 | Reeder et al. |
| 6,885,881 | B2 | 4/2005 | Leonhardt |
| 6,891,525 | B2 | 5/2005 | Ogoro |
| 6,892,278 | B2 | 5/2005 | Ebergen |
| 6,899,695 | B2 | 5/2005 | Herrera |
| 6,915,170 | B2 | 7/2005 | Engleson et al. |
| 6,923,763 | B1 | 8/2005 | Kovatchev et al. |
| 6,924,781 | B1 | 8/2005 | Gelbman |
| 6,928,338 | B1 | 8/2005 | Buchser et al. |
| 6,928,490 | B1 | 8/2005 | Bucholz et al. |
| 6,936,029 | B2 | 8/2005 | Mann et al. |
| 6,945,954 | B2 | 9/2005 | Hochman et al. |
| 6,948,492 | B2 | 9/2005 | Wemeling et al. |
| 6,958,677 | B1 | 10/2005 | Carter |
| 6,958,691 | B1 | 10/2005 | Anderson et al. |
| 6,958,705 | B2 | 10/2005 | Lebel et al. |
| 6,961,448 | B2 | 11/2005 | Nichols et al. |
| 6,969,352 | B2 | 11/2005 | Chiang et al. |
| 6,969,865 | B2 | 11/2005 | Duchon et al. |
| 6,974,437 | B2 | 12/2005 | Lebel et al. |
| 6,979,326 | B2 | 12/2005 | Mann et al. |
| 6,980,958 | B1 | 12/2005 | Surwit et al. |
| 6,985,870 | B2 | 1/2006 | Martucci et al. |
| 6,986,347 | B2 | 1/2006 | Hickle |
| 6,997,880 | B2 | 2/2006 | Carlebach et al. |
| 6,997,920 | B2 | 2/2006 | Mann et al. |
| 6,998,984 | B1 | 2/2006 | Zittrain |
| 7,016,752 | B1 | 3/2006 | Ruben et al. |
| 7,017,293 | B2 | 3/2006 | Riley |
| 7,025,743 | B2 | 4/2006 | Mann et al. |
| 7,029,455 | B2 | 4/2006 | Flaherty |
| 7,038,584 | B2 | 5/2006 | Carter |
| 7,060,031 | B2 | 6/2006 | Webb et al. |
| 7,060,059 | B2 | 6/2006 | Keith et al. |
| 7,069,552 | B2 | 6/2006 | Lindberg et al. |
| 7,072,725 | B2 | 7/2006 | Bristol et al. |
| 7,079,035 | B2 | 7/2006 | Bock et al. |
| 7,092,943 | B2 | 8/2006 | Roese et al. |
| 7,096,072 | B2 | 8/2006 | Engleson et al. |
| 7,099,809 | B2 | 8/2006 | Dori |
| 7,103,419 | B2 | 9/2006 | Engleson et al. |
| 7,103,578 | B2 | 9/2006 | Beck et al. |
| 7,107,106 | B2 | 9/2006 | Engleson et al. |
| 7,108,680 | B2 | 9/2006 | Rohr et al. |
| 7,109,878 | B2 | 9/2006 | Mann et al. |
| 7,114,002 | B1 | 9/2006 | Okumura et al. |
| 7,117,041 | B2 | 10/2006 | Engleson et al. |
| 7,136,645 | B2 | 11/2006 | Hanson et al. |
| 7,137,964 | B2 | 11/2006 | Flaherty |
| 7,142,190 | B2 | 11/2006 | Martinez |
| 7,150,741 | B2 | 12/2006 | Erickson et al. |
| 7,153,289 | B2 | 12/2006 | Vasko |
| 7,154,397 | B2 | 12/2006 | Zerhusen et al. |
| 7,156,807 | B2 | 1/2007 | Carter et al. |
| 7,158,030 | B2 | 1/2007 | Chung |
| 7,161,484 | B2 | 1/2007 | Tsoukalis et al. |
| 7,167,755 | B2 | 1/2007 | Seeberger et al. |
| 7,167,920 | B2 | 1/2007 | Traversat |
| 7,171,277 | B2 | 1/2007 | Engleson et al. |
| 7,171,492 | B1 | 1/2007 | Borella et al. |
| 7,181,493 | B2 | 2/2007 | English et al. |
| 7,185,288 | B2 | 2/2007 | McKeever |
| 7,193,514 | B2 | 3/2007 | Ritson |
| 7,197,025 | B2 | 3/2007 | Chuah |
| 7,201,734 | B2 | 4/2007 | Hickle |
| 7,204,823 | B2 | 4/2007 | Estes et al. |
| 7,213,009 | B2 | 5/2007 | Pestotnik |
| 7,216,802 | B1 | 5/2007 | de la Huerga |
| 7,220,240 | B2 | 5/2007 | Struys et al. |
| 7,224,979 | B2 | 5/2007 | Singhal et al. |
| 7,229,430 | B2 | 6/2007 | Hickle et al. |
| 7,230,529 | B2 | 6/2007 | Ketcherside |
| 7,236,936 | B2 | 6/2007 | White et al. |
| 7,238,164 | B2 | 7/2007 | Childers et al. |
| 7,247,154 | B2 | 7/2007 | Hickle |
| 7,248,239 | B2 | 7/2007 | Dowling |
| 7,250,856 | B2 | 7/2007 | Havekost et al. |
| 7,255,683 | B2 | 8/2007 | Vanderveen et al. |
| 7,256,888 | B2 | 8/2007 | Staehr et al. |
| 7,258,534 | B2 | 8/2007 | Fathallah et al. |
| 7,263,213 | B2 | 8/2007 | Rowe |
| 7,267,664 | B2 | 9/2007 | Rizzo |
| 7,267,665 | B2 | 9/2007 | Steil et al. |
| 7,275,156 | B2 | 9/2007 | Balfanz et al. |
| 7,278,983 | B2 | 10/2007 | Ireland et al. |
| 7,289,815 | B2 | 10/2007 | Gfeller et al. |
| 7,289,948 | B1 | 10/2007 | Mohri |

(56) References Cited

U.S. PATENT DOCUMENTS

| | | | |
|---|---|---|---|
| 7,293,107 | B1 | 11/2007 | Hanson et al. |
| 7,295,119 | B2 | 11/2007 | Rappaport et al. |
| 7,295,556 | B2 | 11/2007 | Roese et al. |
| 7,301,451 | B2 | 11/2007 | Hastings |
| 7,308,300 | B2 | 12/2007 | Toews et al. |
| 7,315,825 | B2 | 1/2008 | Rosenfeld et al. |
| 7,319,386 | B2 | 1/2008 | Collins, Jr. et al. |
| 7,324,000 | B2 | 1/2008 | Zittrain et al. |
| 7,327,705 | B2 | 2/2008 | Fletcher et al. |
| 7,343,224 | B2 | 3/2008 | DiGianfilippo et al. |
| 7,346,025 | B2 | 3/2008 | Bryson |
| 7,347,836 | B2 | 3/2008 | Peterson et al. |
| 7,354,420 | B2 | 4/2008 | Steil et al. |
| 7,369,897 | B2 | 5/2008 | Boveja et al. |
| 7,369,948 | B1 | 5/2008 | Ferenczi et al. |
| 7,383,088 | B2 | 6/2008 | Spinelli et al. |
| 7,384,410 | B2 | 6/2008 | Eggers et al. |
| 7,398,183 | B2 | 7/2008 | Holland et al. |
| 7,398,279 | B2 | 7/2008 | Muno, Jr. et al. |
| 7,399,277 | B2 | 7/2008 | Saidara et al. |
| 7,402,153 | B2 | 7/2008 | Steil et al. |
| 7,420,472 | B2 | 9/2008 | Tran |
| 7,432,807 | B2 | 10/2008 | Schmitt |
| 7,436,454 | B2 | 10/2008 | Yamaguchi et al. |
| 7,447,643 | B1 | 11/2008 | Olson |
| 7,454,314 | B2 | 11/2008 | Holland et al. |
| 7,457,804 | B2 | 11/2008 | Uber, III et al. |
| 7,464,040 | B2 | 12/2008 | Joao |
| 7,469,213 | B1 | 12/2008 | Rao |
| 7,471,994 | B2 | 12/2008 | Ford et al. |
| 7,483,756 | B2 | 1/2009 | Engleson et al. |
| 7,489,808 | B2 | 2/2009 | Gerder |
| 7,490,021 | B2 | 2/2009 | Holland et al. |
| 7,490,048 | B2 | 2/2009 | Joao |
| 7,491,187 | B2 | 2/2009 | Van Den Berghe et al. |
| 7,519,905 | B2 | 4/2009 | Kougiouris et al. |
| 7,523,401 | B1 | 4/2009 | Aldridge |
| 7,524,304 | B2 | 4/2009 | Genosar |
| 7,551,078 | B2 | 6/2009 | Carlson |
| 7,559,321 | B2 | 7/2009 | Wermeling et al. |
| 7,565,197 | B2 | 7/2009 | Haulbrich et al. |
| 7,572,230 | B2 | 8/2009 | Neumann et al. |
| 7,578,802 | B2 | 8/2009 | Hickle |
| 7,621,009 | B2 | 11/2009 | Elhabashy |
| D606,533 | S | 12/2009 | De Jong et al. |
| 7,636,718 | B1 | 12/2009 | Steen et al. |
| 7,640,172 | B2 | 12/2009 | Kuth |
| 7,645,258 | B2 | 1/2010 | White et al. |
| 7,647,237 | B2 | 1/2010 | Malave et al. |
| 7,662,124 | B2 | 2/2010 | Duchon et al. |
| 7,668,731 | B2 | 2/2010 | Martucci et al. |
| 7,671,733 | B2 | 3/2010 | McNeal et al. |
| 7,678,071 | B2 | 3/2010 | Lebel et al. |
| 7,687,678 | B2 | 3/2010 | Jacobs |
| 7,697,994 | B2 | 4/2010 | VanDanacker et al. |
| 7,698,239 | B2 | 4/2010 | Lieuallen |
| 7,705,727 | B2 | 4/2010 | Pestotnik |
| 7,724,147 | B2 | 5/2010 | Brown et al. |
| 7,739,126 | B1 | 6/2010 | Cave |
| 7,746,218 | B2 | 6/2010 | Collins, Jr. |
| 7,766,873 | B2 | 8/2010 | Moberg et al. |
| 7,776,029 | B2 | 8/2010 | Whitehurst et al. |
| 7,776,031 | B2 | 8/2010 | Hartlaub et al. |
| 7,785,313 | B2 | 8/2010 | Mastrototaro |
| 7,788,369 | B2 | 8/2010 | McAllen et al. |
| 7,806,852 | B1 | 10/2010 | Jurson |
| 7,806,886 | B2 | 10/2010 | Kanderian, Jr. et al. |
| 7,826,981 | B2 | 11/2010 | Goode, Jr. et al. |
| 7,835,927 | B2 | 11/2010 | Schlotterbeck et al. |
| 7,836,314 | B2 | 11/2010 | Chieu |
| 7,856,276 | B2 | 12/2010 | Ripart et al. |
| 7,860,583 | B2 | 12/2010 | Condurso et al. |
| 7,864,771 | B2 | 1/2011 | Tavares et al. |
| 7,868,754 | B2 | 1/2011 | Salvat, Jr. |
| 7,871,394 | B2 | 1/2011 | Halbert et al. |
| 7,886,231 | B2 | 2/2011 | Hopermann et al. |
| 7,895,053 | B2 | 2/2011 | Holland et al. |
| 7,896,842 | B2 | 3/2011 | Palmroos et al. |
| 7,899,546 | B2 | 3/2011 | Sieracki et al. |
| 7,905,710 | B2 | 3/2011 | Wang et al. |
| 7,920,061 | B2 | 4/2011 | Klein et al. |
| 7,933,780 | B2 | 4/2011 | de la Huerga |
| 7,938,796 | B2 | 5/2011 | Moubayed |
| 7,945,452 | B2 | 5/2011 | Fathallah et al. |
| 7,974,714 | B2 | 7/2011 | Hoffberg |
| 7,976,508 | B2 | 7/2011 | Hoag |
| 7,996,241 | B2 | 8/2011 | Zak |
| 8,034,026 | B2 | 10/2011 | Grant |
| 8,038,593 | B2 | 10/2011 | Friedman et al. |
| 8,048,040 | B2 | 11/2011 | Kiani |
| 8,060,576 | B2 | 11/2011 | Chan et al. |
| 8,065,161 | B2 | 11/2011 | Howard et al. |
| 8,066,672 | B2 | 11/2011 | Mandro |
| 8,075,514 | B2 | 12/2011 | Butterfield et al. |
| 8,078,983 | B2 | 12/2011 | Davis et al. |
| 8,082,018 | B2 | 12/2011 | Duchon et al. |
| 8,082,312 | B2 | 12/2011 | Chan et al. |
| 8,095,692 | B2 | 1/2012 | Mehta et al. |
| 8,126,730 | B2 | 2/2012 | Dicks et al. |
| 8,147,448 | B2 | 4/2012 | Sundar et al. |
| 8,149,131 | B2 | 4/2012 | Blomquist |
| 8,169,914 | B2 | 5/2012 | Bajpai |
| 8,171,094 | B2 | 5/2012 | Chan et al. |
| 8,172,798 | B2 | 5/2012 | Hungerford et al. |
| 8,185,322 | B2 | 5/2012 | Schroeder et al. |
| 8,195,478 | B2 | 6/2012 | Petersen et al. |
| 8,206,350 | B2 | 6/2012 | Mann et al. |
| 8,219,413 | B2 | 7/2012 | Martinez et al. |
| 8,231,578 | B2 | 7/2012 | Fathallah et al. |
| 8,234,128 | B2 | 7/2012 | Martucci et al. |
| 8,267,892 | B2 | 9/2012 | Spencer et al. |
| 8,271,106 | B2 | 9/2012 | Wehba et al. |
| 8,287,495 | B2 | 10/2012 | Michaud et al. |
| 8,291,337 | B2 | 10/2012 | Gannin et al. |
| 8,298,184 | B2 | 10/2012 | DiPerna et al. |
| 8,312,272 | B1 | 11/2012 | Serenyl et al. |
| 8,352,290 | B2 | 1/2013 | Bartz et al. |
| 8,359,338 | B2 | 1/2013 | Butterfield et al. |
| 8,380,536 | B2 | 2/2013 | Howard et al. |
| 8,387,112 | B1 | 2/2013 | Ranjan et al. |
| 8,394,077 | B2 | 3/2013 | Jacobson et al. |
| 8,398,592 | B2 | 3/2013 | Leibner-Druska |
| 8,403,908 | B2 | 3/2013 | Jacobson et al. |
| 8,435,206 | B2 | 5/2013 | Evans et al. |
| 8,449,523 | B2 | 5/2013 | Brukalo et al. |
| 8,452,953 | B2 | 5/2013 | Buck et al. |
| 8,453,645 | B2 | 6/2013 | Figueiredo et al. |
| 8,472,630 | B2 | 6/2013 | Konrad et al. |
| 8,480,648 | B2 | 7/2013 | Burnett et al. |
| 8,486,019 | B2 | 7/2013 | White et al. |
| 8,489,427 | B2 | 7/2013 | Simpson et al. |
| 8,494,879 | B2 | 7/2013 | Davis et al. |
| 8,504,179 | B2 | 8/2013 | Blomquist |
| 8,517,990 | B2 | 8/2013 | Teel et al. |
| 8,518,021 | B2 | 8/2013 | Stewart et al. |
| 8,543,416 | B2 | 9/2013 | Palmroos et al. |
| 8,551,038 | B2 | 10/2013 | Tsoukalis et al. |
| 8,560,345 | B2 | 10/2013 | Wehba et al. |
| 8,567,681 | B2 | 10/2013 | Borges et al. |
| 8,577,692 | B2 | 11/2013 | Silkaitis et al. |
| 8,579,884 | B2 | 11/2013 | Lanier et al. |
| 8,626,530 | B1 | 1/2014 | Tran et al. |
| 8,655,676 | B2 | 2/2014 | Wehba et al. |
| 8,660,860 | B2 | 2/2014 | Wehba et al. |
| 8,662,388 | B2 | 3/2014 | Belkin |
| 8,666,769 | B2 | 3/2014 | Butler et al. |
| 8,667,293 | B2 | 3/2014 | Birtwhistle et al. |
| 8,687,811 | B2 | 4/2014 | Nierzwick et al. |
| 8,700,421 | B2 | 4/2014 | Feng et al. |
| 8,731,960 | B2 | 5/2014 | Butler et al. |
| 8,768,719 | B2 | 7/2014 | Wehba et al. |
| 8,771,251 | B2 | 7/2014 | Ruchti et al. |
| 8,777,894 | B2 | 7/2014 | Butterfield et al. |
| 8,777,895 | B2 | 7/2014 | Hsu et al. |

(56) References Cited

U.S. PATENT DOCUMENTS 8,799,012 B2 8/2014 Butler et al.
8,876,793 B2 11/2014 Ledford et al.
8,886,316 B1 11/2014 Juels
8,922,330 B2 12/2014 Moberg et al.
8,936,565 B2 1/2015 Chawla
8,945,043 B2 2/2015 Lee et al.
8,952,794 B2 2/2015 Blomquist et al.
8,959,617 B2 2/2015 Newlin et al.
8,998,100 B2 4/2015 Halbert et al.
9,026,370 B2 5/2015 Rubalcaba et al.
9,069,887 B2 6/2015 Gupta et al.
9,077,544 B2 7/2015 Baker et al.
9,089,642 B2 7/2015 Murphy et al.
9,114,217 B2 8/2015 Sur et al.
9,123,077 B2 9/2015 Silkaitis et al.
9,192,712 B2 11/2015 DeBelser et al.
9,240,002 B2 1/2016 Hume et al.
9,283,339 B2 3/2016 Sherman
9,292,692 B2 3/2016 Wallrabenstein
9,302,035 B2 4/2016 Marseille et al.
9,313,154 B1 4/2016 Son
9,381,296 B2 7/2016 Arrizza et al.
9,393,362 B2 7/2016 Cozmi et al.
9,430,655 B1 8/2016 Stockton et al.
9,438,580 B2 9/2016 Kupper
9,483,615 B2 11/2016 Roberts
9,498,583 B2 11/2016 Sur et al.
9,539,383 B2 1/2017 Kohlbrecher
9,572,923 B2 2/2017 Howard et al.
9,594,875 B2 3/2017 Arrizza et al.
9,604,000 B2 3/2017 Wehba et al.
9,641,432 B2 5/2017 Jha et al.
9,649,431 B2 5/2017 Gray et al.
9,662,436 B2 5/2017 Belkin et al.
9,690,909 B2 6/2017 Stewart et al.
9,707,341 B2 7/2017 Dumas, III et al.
9,717,845 B2 8/2017 Istoc
9,724,470 B2 8/2017 Day et al.
9,729,330 B2 8/2017 Verma
9,764,082 B2 9/2017 Day et al.
9,886,550 B2 2/2018 Lee et al.
9,904,765 B2 2/2018 Borges
9,943,269 B2 4/2018 Muhsin et al.
9,967,739 B2 5/2018 Proennecke et al.
9,971,871 B2 5/2018 Arrizza et al.
9,980,140 B1 5/2018 Spencer et al.
9,995,611 B2 6/2018 Ruchti et al.
10,022,498 B2 7/2018 Ruchti et al.
10,042,986 B2 8/2018 Ruchti et al.
10,046,112 B2 8/2018 Oruklu et al.
10,166,328 B2 1/2019 Oruklu et al.
10,173,008 B2 1/2019 Simpson et al.
10,188,849 B2 1/2019 Fangrow
10,233,179 B2 3/2019 Ng et al.
10,238,799 B2 3/2019 Kohlbrecher
10,238,801 B2 3/2019 Wehba et al.
10,242,060 B2 3/2019 Butler et al.
10,300,194 B2 5/2019 Day et al.
10,311,972 B2 6/2019 Kohlbrecher et al.
10,314,974 B2 6/2019 Day et al.
10,333,843 B2 6/2019 Jha et al.
10,341,866 B1 7/2019 Spencer et al.
10,356,087 B1 7/2019 Vetter
10,366,210 B2 7/2019 Moskal
10,409,995 B1 9/2019 Wasiq
10,430,761 B2 10/2019 Hume et al.
10,434,246 B2 10/2019 Silkaitis et al.
10,438,001 B1 10/2019 Hariprasad
10,452,842 B2 10/2019 Dhondse
10,453,157 B2 10/2019 Kamen et al.
10,463,788 B2 11/2019 Day
10,516,536 B2 12/2019 Rommel
10,617,815 B2 4/2020 Day et al.
10,646,651 B2 5/2020 Day et al.
10,681,207 B1 6/2020 Johnson et al.
10,692,595 B2 6/2020 Xavier et al.
10,728,262 B1 7/2020 Vaswani
10,740,436 B2 8/2020 Moskal et al.
10,741,280 B2 8/2020 Xavier et al.
10,757,219 B2 8/2020 Moskal
10,765,799 B2 9/2020 Belkin et al.
10,799,632 B2 10/2020 Kohlbrecher
10,812,380 B2 10/2020 Jha et al.
10,861,592 B2 12/2020 Xavier et al.
10,898,641 B2 1/2021 Day et al.
10,950,339 B2 3/2021 Xavier et al.
10,964,428 B2 3/2021 Xavier et al.
11,013,861 B2 5/2021 Wehba et al.
11,037,668 B2 6/2021 Ruchti et al.
11,052,193 B2 7/2021 Day et al.
11,139,058 B2 10/2021 Xavier et al.
11,151,290 B2 10/2021 Karakoyunlu et al.
11,152,108 B2 10/2021 Xavier et al.
11,152,109 B2 10/2021 Xavier et al.
11,152,110 B2 10/2021 Xavier et al.
11,194,810 B2 12/2021 Butler et al.
11,235,100 B2 2/2022 Howard et al.
11,289,183 B2 3/2022 Kohlbrecher
11,309,070 B2 4/2022 Xavier et al.
11,324,960 B2 5/2022 Sjoquist
11,328,804 B2 5/2022 Xavier et al.
11,328,805 B2 5/2022 Xavier et al.
11,373,753 B2 6/2022 Xavier et al.
11,437,132 B2 9/2022 Xavier et al.
11,470,000 B2 10/2022 Jha et al.
11,483,402 B2 10/2022 Xavier et al.
11,483,403 B2 10/2022 Xavier et al.
11,501,877 B2 11/2022 Kohlbrecher et al.
11,571,508 B2 2/2023 Jacobson et al.
11,574,721 B2 2/2023 Kohlbrecher
11,574,737 B2 2/2023 Dharwad et al.
11,587,669 B2 2/2023 Xavier et al.
11,590,057 B2 2/2023 Tagliamento et al.
11,594,326 B2 2/2023 Xavier et al.
11,605,468 B2 3/2023 Jacobson et al.
11,626,205 B2 4/2023 Arrizza et al.
11,628,246 B2 4/2023 Day et al.
11,628,254 B2 4/2023 Day et al.
11,654,237 B2 5/2023 Wehba et al.
11,670,416 B2 6/2023 Xavier et al.
11,763,927 B2 9/2023 Ruchti et al.
11,783,935 B2 10/2023 Xavier et al.
11,881,297 B2 1/2024 Xavier et al.
11,923,076 B2 3/2024 Xavier et al.
11,986,623 B2 5/2024 Jacobson et al.
11,996,188 B2 5/2024 Arrizza et al.
12,002,562 B2 6/2024 Kohlbrecher
12,028,414 B1 7/2024 Borges et al.
12,036,390 B2 7/2024 Wehba et al.
12,040,068 B2 7/2024 Xavier et al.
12,042,623 B2 7/2024 Day et al.
12,042,631 B2 7/2024 Day et al.
12,046,361 B2 7/2024 Xavier et al.
12,047,292 B2 7/2024 Jha et al.
12,097,351 B2 9/2024 Belkin et al.
12,130,910 B2 10/2024 Vivek et al.
12,142,370 B2 11/2024 Xavier et al.
12,205,699 B1 1/2025 Kim et al.
12,205,702 B2 1/2025 Xavier et al.
12,278,868 B2 4/2025 Borges et al.
12,303,464 B2 5/2025 Tagliamento et al.
12,337,142 B2 6/2025 Wehba et al.
12,380,982 B2 8/2025 Kohlbrecher
12,380,997 B2 8/2025 Arrizza et al.
12,395,429 B2 8/2025 Jha et al.
12,420,009 B2 9/2025 Day et al.
12,431,238 B2 9/2025 Vivek et al.
12,458,749 B2 11/2025 Jacobson et al.
12,562,268 B2 2/2026 Fryman
12,592,305 B2 3/2026 Xavier et al.
2001/0016056 A1 8/2001 Westphal et al.
2001/0029178 A1 10/2001 Criss et al.
2001/0031944 A1 10/2001 Peterson et al.
2001/0032099 A1 10/2001 Joao

(56) References Cited

U.S. PATENT DOCUMENTS

2001/0037060 A1 11/2001 Thompson et al.
2001/0044731 A1 11/2001 Coffman et al.
2001/0048027 A1 12/2001 Walsh
2001/0051787 A1 12/2001 Haller et al.
2001/0056358 A1 12/2001 Dulong et al.
2002/0010595 A1 1/2002 Kapp
2002/0013551 A1 1/2002 Zaitsu et al.
2002/0013723 A1 1/2002 Mise
2002/0015018 A1 2/2002 Shimazu et al.
2002/0019584 A1 2/2002 Schulze et al.
2002/0021700 A1 2/2002 Hata et al.
2002/0026103 A1 2/2002 Norris et al.
2002/0029776 A1 3/2002 Blomquist
2002/0032583 A1 3/2002 Joao
2002/0038392 A1 3/2002 de la Huerga
2002/0040208 A1 4/2002 Flaherty et al.
2002/0040282 A1 4/2002 Bailey et al.
2002/0044043 A1 4/2002 Chaco et al.
2002/0044059 A1 4/2002 Reeder et al.
2002/0046335 A1 4/2002 Baum-Waidner
2002/0082728 A1 6/2002 Mueller et al.
2002/0087115 A1 7/2002 Hartlaub
2002/0087116 A1 7/2002 Hartlaub
2002/0095486 A1 7/2002 Bahl
2002/0103675 A1 8/2002 Vanelli
2002/0123905 A1 9/2002 Goodroe et al.
2002/0143580 A1 10/2002 Bristol et al.
2002/0152239 A1 10/2002 Bautista-Lloyd et al.
2002/0154600 A1 10/2002 Ido et al.
2002/0161591 A1 10/2002 Danneels
2002/0173702 A1 11/2002 Lebel et al.
2002/0173875 A1 11/2002 Wallace et al.
2002/0193679 A1 12/2002 Malave et al.
2002/0194329 A1 12/2002 Alling
2003/0009244 A1 1/2003 Engleson
2003/0013959 A1 1/2003 Grunwald et al.
2003/0014222 A1 1/2003 Klass et al.
2003/0014817 A1 1/2003 Gallant et al.
2003/0025602 A1 2/2003 Medema et al.
2003/0028082 A1 2/2003 Thompson
2003/0036683 A1 2/2003 Kehr et al.
2003/0036744 A1 2/2003 Struys et al.
2003/0047126 A1 3/2003 Tomaschko
2003/0047600 A1 3/2003 Nakanishi et al.
2003/0050621 A1 3/2003 Lebel et al.
2003/0059750 A1 3/2003 Bindler et al.
2003/0060688 A1 3/2003 Ciarniello et al.
2003/0069963 A1 4/2003 Jayant et al.
2003/0079746 A1 5/2003 Hickle
2003/0097529 A1 5/2003 Arimilli et al.
2003/0104982 A1 6/2003 Wittmann et al.
2003/0105389 A1 6/2003 Noonan et al.
2003/0106553 A1 6/2003 Vanderveen
2003/0115358 A1 6/2003 Yun
2003/0120384 A1 6/2003 Haitin et al.
2003/0125662 A1 7/2003 Bui
2003/0130616 A1 7/2003 Steil
2003/0135087 A1 7/2003 Hickle et al.
2003/0139701 A1 7/2003 White et al.
2003/0140928 A1 7/2003 Bui et al.
2003/0140929 A1 7/2003 Wilkes et al.
2003/0141981 A1 7/2003 Bui et al.
2003/0143746 A1 7/2003 Sage, Jr.
2003/0144878 A1 7/2003 Wilkes et al.
2003/0158749 A1 8/2003 Olchanski et al.
2003/0187338 A1 10/2003 Say et al.
2003/0200116 A1 10/2003 Forrester
2003/0204416 A1 10/2003 Acharya
2003/0204781 A1 10/2003 Peebles et al.
2003/0212364 A1 11/2003 Mann et al.
2003/0212379 A1 11/2003 Bylund et al.
2003/0212821 A1 11/2003 Gillies et al.
2003/0216831 A1 11/2003 Hart et al.
2003/0217962 A1 11/2003 Childers et al.
2004/0008123 A1 1/2004 Carrender et al.
2004/0010786 A1 1/2004 Cool et al.
2004/0015132 A1 1/2004 Brown
2004/0019464 A1 1/2004 Martucci et al.
2004/0019607 A1 1/2004 Moubayed et al.
2004/0030323 A1 2/2004 Ullestad et al.
2004/0039257 A1 2/2004 Hickle
2004/0057226 A1 3/2004 Berthou et al.
2004/0064341 A1 4/2004 Langan et al.
2004/0064342 A1 4/2004 Browne et al.
2004/0064435 A1 4/2004 Moubayed et al.
2004/0073161 A1 4/2004 Tachibana
2004/0073811 A1 4/2004 Sanin
2004/0077934 A1 4/2004 Massad
2004/0078231 A1 4/2004 Wilkes et al.
2004/0078236 A1 4/2004 Stoodley et al.
2004/0085186 A1 5/2004 Eveland et al.
2004/0104271 A1 6/2004 Martucci et al.
2004/0122530 A1 6/2004 Hansen
2004/0128162 A1 7/2004 Schlotterbeck et al.
2004/0128163 A1 7/2004 Goodman et al.
2004/0133441 A1 7/2004 Brady et al.
2004/0139004 A1 7/2004 Cohen et al.
2004/0145480 A1 7/2004 Despotis
2004/0147034 A1 7/2004 Gore et al.
2004/0167464 A1 8/2004 Ireland et al.
2004/0167465 A1 8/2004 Kohler
2004/0167804 A1 8/2004 Simpson
2004/0172222 A1 9/2004 Simpson et al.
2004/0172283 A1 9/2004 Vanderveen
2004/0172301 A1 9/2004 Mihai et al.
2004/0172302 A1 9/2004 Martucci et al.
2004/0176667 A1 9/2004 Mihai et al.
2004/0176980 A1 9/2004 Bulitta et al.
2004/0176984 A1 9/2004 White et al.
2004/0181314 A1 9/2004 Zaleski
2004/0189708 A1 9/2004 Larcheveque et al.
2004/0193325 A1 9/2004 Bonderud
2004/0193328 A1 9/2004 Butterfield et al.
2004/0204673 A1 10/2004 Flaherty et al.
2004/0215278 A1 10/2004 Stegink et al.
2004/0220517 A1 11/2004 Starkweather et al.
2004/0225252 A1 11/2004 Gillespie et al.
2004/0236240 A1 11/2004 Kraus et al.
2004/0243438 A1 12/2004 Mintz
2004/0254434 A1 12/2004 Goodnow et al.
2005/0010269 A1 1/2005 Lebel et al.
2005/0020886 A1 1/2005 Hutchinson et al.
2005/0021006 A1 1/2005 Tonnies
2005/0027560 A1 2/2005 Cook
2005/0027567 A1 2/2005 Taha
2005/0038311 A1 2/2005 Kuth
2005/0038669 A1 2/2005 Sachdeva et al.
2005/0038680 A1 2/2005 McMahon
2005/0040226 A1 2/2005 Al-Sheikh
2005/0043620 A1 2/2005 Fallows et al.
2005/0049910 A1 3/2005 Lancaster et al.
2005/0055242 A1 3/2005 Bello et al.
2005/0055244 A1 3/2005 Mullan et al.
2005/0065465 A1 3/2005 Lebel et al.
2005/0065817 A1 3/2005 Mihai et al.
2005/0075544 A1 4/2005 Shapiro et al.
2005/0080801 A1 4/2005 Kothandaraman et al.
2005/0086071 A1 4/2005 Fox, Jr. et al.
2005/0086072 A1 4/2005 Fox
2005/0088704 A1 4/2005 Vaschillo et al.
2005/0090808 A1 4/2005 Malave et al.
2005/0099624 A1 5/2005 Staehr
2005/0102162 A1 5/2005 Blumenfeld
2005/0102165 A1 5/2005 Oshita et al.
2005/0102167 A1 5/2005 Kapoor
2005/0102669 A1 5/2005 Marney et al.
2005/0107923 A1 5/2005 Vanderveen
2005/0108057 A1 5/2005 Cohen et al.
2005/0117529 A1 6/2005 Ramos-Escano
2005/0119788 A1 6/2005 Engleson et al.
2005/0119914 A1 6/2005 Batch
2005/0131739 A1 6/2005 Rabinowitz et al.
2005/0135306 A1 6/2005 McAllen et al.
2005/0137522 A1 6/2005 Aoki

(56) References Cited

U.S. PATENT DOCUMENTS

| | | | |
|---|---|---|---|
| 2005/0137573 | A1 | 6/2005 | McLaughlin |
| 2005/0138428 | A1 | 6/2005 | McAllen et al. |
| 2005/0154769 | A1 | 7/2005 | Eckart et al. |
| 2005/0160057 | A1 | 7/2005 | Wefers et al. |
| 2005/0171503 | A1 | 8/2005 | Van Den Berghe et al. |
| 2005/0171815 | A1 | 8/2005 | Vanderveen |
| 2005/0177096 | A1 | 8/2005 | Bollish et al. |
| 2005/0177395 | A1 | 8/2005 | Blomquist |
| 2005/0182306 | A1 | 8/2005 | Sloan |
| 2005/0182355 | A1 | 8/2005 | Bui |
| 2005/0187950 | A1 | 8/2005 | Parker |
| 2005/0192557 | A1 | 9/2005 | Brauker et al. |
| 2005/0197554 | A1 | 9/2005 | Polcha |
| 2005/0197621 | A1 | 9/2005 | Poulsen et al. |
| 2005/0210037 | A1 | 9/2005 | Wefers et al. |
| 2005/0216479 | A1 | 9/2005 | Wefers et al. |
| 2005/0216480 | A1 | 9/2005 | Wefers et al. |
| 2005/0223045 | A1 | 10/2005 | Funahashi et al. |
| 2005/0224083 | A1 | 10/2005 | Crass |
| 2005/0234746 | A1 | 10/2005 | Funahashi |
| 2005/0240305 | A1 | 10/2005 | Bogash et al. |
| 2005/0246416 | A1 | 11/2005 | Blomquist |
| 2005/0251418 | A1 | 11/2005 | Fox, Jr. et al. |
| 2005/0261660 | A1 | 11/2005 | Choi |
| 2005/0273059 | A1 | 12/2005 | Mernoe et al. |
| 2005/0273367 | A1 | 12/2005 | Nourie et al. |
| 2005/0277873 | A1 | 12/2005 | Stewart et al. |
| 2005/0277890 | A1 | 12/2005 | Stewart et al. |
| 2005/0278194 | A1 | 12/2005 | Holland et al. |
| 2006/0002556 | A1 | 1/2006 | Paul |
| 2006/0004772 | A1 | 1/2006 | Hagan et al. |
| 2006/0009727 | A1 | 1/2006 | O'Mahony et al. |
| 2006/0009734 | A1 | 1/2006 | Martin |
| 2006/0010098 | A1 | 1/2006 | Goodnow et al. |
| 2006/0042139 | A1 | 3/2006 | Mendes |
| 2006/0047270 | A1 | 3/2006 | Shelton |
| 2006/0053036 | A1 | 3/2006 | Coffman et al. |
| 2006/0064020 | A1 | 3/2006 | Burnes et al. |
| 2006/0074633 | A1 | 4/2006 | Mahesh et al. |
| 2006/0074920 | A1 | 4/2006 | Wefers et al. |
| 2006/0079831 | A1 | 4/2006 | Gilbert |
| 2006/0089539 | A1 | 4/2006 | Miodownik et al. |
| 2006/0089854 | A1 | 4/2006 | Holland et al. |
| 2006/0089855 | A1 | 4/2006 | Holland et al. |
| 2006/0100746 | A1 | 5/2006 | Leibner-Druska |
| 2006/0100907 | A1 | 5/2006 | Holland et al. |
| 2006/0106649 | A1 | 5/2006 | Eggers et al. |
| 2006/0111943 | A1 | 5/2006 | Wu |
| 2006/0116639 | A1 | 6/2006 | Russell |
| 2006/0116904 | A1 | 6/2006 | Brem |
| 2006/0116907 | A1 | 6/2006 | Rhodes et al. |
| 2006/0122481 | A1 | 6/2006 | Sievenpiper et al. |
| 2006/0122867 | A1 | 6/2006 | Eggers et al. |
| 2006/0129140 | A1 | 6/2006 | Todd et al. |
| 2006/0129429 | A1 | 6/2006 | Moubayed et al. |
| 2006/0129434 | A1 | 6/2006 | Smitherman et al. |
| 2006/0129435 | A1 | 6/2006 | Smitherman et al. |
| 2006/0136266 | A1 | 6/2006 | Tarassenko et al. |
| 2006/0136271 | A1 | 6/2006 | Eggers et al. |
| 2006/0143051 | A1 | 6/2006 | Eggers et al. |
| 2006/0173260 | A1 | 8/2006 | Gaoni et al. |
| 2006/0173406 | A1 | 8/2006 | Hayes et al. |
| 2006/0173715 | A1 | 8/2006 | Wang et al. |
| 2006/0173927 | A1 | 8/2006 | Beyer et al. |
| 2006/0190302 | A1 | 8/2006 | Eggers et al. |
| 2006/0195022 | A1 | 8/2006 | Trepagnier et al. |
| 2006/0200007 | A1 | 9/2006 | Brockway et al. |
| 2006/0200369 | A1 | 9/2006 | Batch et al. |
| 2006/0211404 | A1 | 9/2006 | Cromp et al. |
| 2006/0224141 | A1 | 10/2006 | Rush et al. |
| 2006/0229918 | A1 | 10/2006 | Fotsch et al. |
| 2006/0236373 | A1 | 10/2006 | Graves et al. |
| 2006/0247606 | A1 | 11/2006 | Batch |
| 2006/0253554 | A1 | 11/2006 | Uwais |
| 2006/0258985 | A1 | 11/2006 | Russell |
| 2006/0259327 | A1 | 11/2006 | Hoag |
| 2006/0264895 | A1 | 11/2006 | Flanders |
| 2006/0267753 | A1 | 11/2006 | Hussey et al. |
| 2006/0268710 | A1 | 11/2006 | Appanna et al. |
| 2006/0270971 | A1 | 11/2006 | Gelfand et al. |
| 2006/0277206 | A1 | 12/2006 | Bailey et al. |
| 2006/0287885 | A1 | 12/2006 | Frick |
| 2007/0015972 | A1 | 1/2007 | Wang et al. |
| 2007/0016443 | A1 | 1/2007 | Wachman et al. |
| 2007/0021715 | A1 | 1/2007 | Kohlbrenner et al. |
| 2007/0027506 | A1 | 2/2007 | Stender et al. |
| 2007/0060796 | A1 | 3/2007 | Kim |
| 2007/0060870 | A1 | 3/2007 | Tolle et al. |
| 2007/0060871 | A1 | 3/2007 | Istoc |
| 2007/0061393 | A1 | 3/2007 | Moore |
| 2007/0065363 | A1 | 3/2007 | Dalal et al. |
| 2007/0073419 | A1 | 3/2007 | Sesay |
| 2007/0073822 | A1 | 3/2007 | Bennett et al. |
| 2007/0078314 | A1 | 4/2007 | Grounsell |
| 2007/0083870 | A1 | 4/2007 | Kanakogi |
| 2007/0088333 | A1 | 4/2007 | Levin et al. |
| 2007/0093786 | A1 | 4/2007 | Goldsmith et al. |
| 2007/0098565 | A1 | 5/2007 | Parsee et al. |
| 2007/0100665 | A1 | 5/2007 | Brown |
| 2007/0100667 | A1 | 5/2007 | Bardy |
| 2007/0106126 | A1 | 5/2007 | Mannheimer et al. |
| 2007/0112298 | A1 | 5/2007 | Mueller et al. |
| 2007/0116037 | A1 | 5/2007 | Moore |
| 2007/0118405 | A1 | 5/2007 | Campbell et al. |
| 2007/0135866 | A1 | 6/2007 | Baker et al. |
| 2007/0136098 | A1 | 6/2007 | Smythe et al. |
| 2007/0142822 | A1 | 6/2007 | Remde |
| 2007/0156282 | A1 | 7/2007 | Dunn |
| 2007/0156452 | A1 | 7/2007 | Batch |
| 2007/0169008 | A1 | 7/2007 | Varanasi et al. |
| 2007/0179448 | A1 | 8/2007 | Lim et al. |
| 2007/0186923 | A1 | 8/2007 | Poutiatine et al. |
| 2007/0191817 | A1 | 8/2007 | Martin |
| 2007/0191973 | A1 | 8/2007 | Holzbauer et al. |
| 2007/0213657 | A1 | 9/2007 | Jennewine et al. |
| 2007/0213684 | A1 | 9/2007 | Hickle et al. |
| 2007/0214003 | A1 | 9/2007 | Holland et al. |
| 2007/0215545 | A1 | 9/2007 | Bissler et al. |
| 2007/0232867 | A1 | 10/2007 | Hansmann |
| 2007/0233035 | A1 | 10/2007 | Wehba et al. |
| 2007/0233049 | A1 | 10/2007 | Wehba et al. |
| 2007/0233206 | A1 | 10/2007 | Frikart |
| 2007/0233521 | A1 | 10/2007 | Wehba et al. |
| 2007/0240215 | A1 | 10/2007 | Flores |
| 2007/0251835 | A1 | 11/2007 | Mehta et al. |
| 2007/0253021 | A1 | 11/2007 | Mehta et al. |
| 2007/0254593 | A1 | 11/2007 | Jollota et al. |
| 2007/0255125 | A1 | 11/2007 | Moberg et al. |
| 2007/0257788 | A1 | 11/2007 | Carlson |
| 2007/0258395 | A1 | 11/2007 | Jollota et al. |
| 2007/0288423 | A1 | 12/2007 | Kimoto |
| 2007/0291647 | A1 | 12/2007 | Smith |
| 2007/0299687 | A1 | 12/2007 | Palmer et al. |
| 2007/0299695 | A1 | 12/2007 | Jung et al. |
| 2008/0001771 | A1 | 1/2008 | Faoro et al. |
| 2008/0004904 | A1 | 1/2008 | Tran |
| 2008/0009684 | A1 | 1/2008 | Corsetti et al. |
| 2008/0013559 | A1 | 1/2008 | Smith |
| 2008/0033361 | A1 | 2/2008 | Evans et al. |
| 2008/0033966 | A1 | 2/2008 | Wahl |
| 2008/0034323 | A1 | 2/2008 | Blomquist |
| 2008/0041942 | A1 | 2/2008 | Aissa |
| 2008/0052704 | A1 | 2/2008 | Wysocki |
| 2008/0065007 | A1 | 3/2008 | Peterson et al. |
| 2008/0065417 | A1 | 3/2008 | Jung et al. |
| 2008/0071217 | A1 | 3/2008 | Moubayed et al. |
| 2008/0071251 | A1 | 3/2008 | Moubayed et al. |
| 2008/0086088 | A1 | 4/2008 | Malcolm |
| 2008/0091466 | A1 | 4/2008 | Butler et al. |
| 2008/0095339 | A1 | 4/2008 | Elliott |
| 2008/0097289 | A1 | 4/2008 | Steil et al. |
| 2008/0097552 | A1 | 4/2008 | Dicks et al. |
| 2008/0126969 | A1 | 5/2008 | Blomquist |
| 2008/0139907 | A1 | 6/2008 | Rao et al. |

(56) References Cited

U.S. PATENT DOCUMENTS

| | | | |
|---|---|---|---|
| 2008/0148047 | A1 | 6/2008 | Appenzeller et al. |
| 2008/0149117 | A1 | 6/2008 | Raghuram |
| 2008/0154177 | A1 | 6/2008 | Moubayed et al. |
| 2008/0172337 | A1 | 7/2008 | Banfield et al. |
| 2008/0184219 | A1 | 7/2008 | Matsumoto |
| 2008/0188796 | A1 | 8/2008 | Steil et al. |
| 2008/0214919 | A1 | 9/2008 | Harmon et al. |
| 2008/0244717 | A1 | 10/2008 | Jelatis et al. |
| 2008/0246748 | A1 | 10/2008 | Cassidy et al. |
| 2008/0256305 | A1 | 10/2008 | Kwon |
| 2008/0259926 | A1 | 10/2008 | Tavares et al. |
| 2008/0262469 | A1 | 10/2008 | Bristol et al. |
| 2008/0269714 | A1 | 10/2008 | Mastrototaro et al. |
| 2008/0269723 | A1 | 10/2008 | Mastrototaro et al. |
| 2008/0275384 | A1 | 11/2008 | Mastrototaro et al. |
| 2008/0300572 | A1 | 12/2008 | Rankers et al. |
| 2008/0301298 | A1 | 12/2008 | Bernardi et al. |
| 2008/0320387 | A1 | 12/2008 | Sasaki et al. |
| 2008/0320466 | A1 | 12/2008 | Dias |
| 2009/0003554 | A1 | 1/2009 | Katis et al. |
| 2009/0005703 | A1 | 1/2009 | Fasciano |
| 2009/0005728 | A1 | 1/2009 | Weinert et al. |
| 2009/0006061 | A1 | 1/2009 | Thukral et al. |
| 2009/0006129 | A1 | 1/2009 | Thukral |
| 2009/0006133 | A1 | 1/2009 | Weinert |
| 2009/0018495 | A1 | 1/2009 | Panduro |
| 2009/0036750 | A1 | 2/2009 | Weinstein et al. |
| 2009/0051560 | A1 | 2/2009 | Manning et al. |
| 2009/0054743 | A1 | 2/2009 | Stewart |
| 2009/0054754 | A1 | 2/2009 | McMahon et al. |
| 2009/0057399 | A1 | 3/2009 | Sajkowsky |
| 2009/0063187 | A1 | 3/2009 | Johnson et al. |
| 2009/0069785 | A1 | 3/2009 | Miller et al. |
| 2009/0088701 | A1 | 4/2009 | Larsen |
| 2009/0099866 | A1 | 4/2009 | Newman |
| 2009/0099867 | A1 | 4/2009 | Newman |
| 2009/0135196 | A1 | 5/2009 | Holland et al. |
| 2009/0143662 | A1 | 6/2009 | Estes et al. |
| 2009/0149743 | A1 | 6/2009 | Barron et al. |
| 2009/0150174 | A1 | 6/2009 | Buck et al. |
| 2009/0150439 | A1 | 6/2009 | Gejdos et al. |
| 2009/0150878 | A1 | 6/2009 | Pathak et al. |
| 2009/0156991 | A1 | 6/2009 | Roberts |
| 2009/0157695 | A1 | 6/2009 | Roberts |
| 2009/0158274 | A1 | 6/2009 | Roberts |
| 2009/0177146 | A1 | 7/2009 | Nesbitt et al. |
| 2009/0177769 | A1 | 7/2009 | Roberts |
| 2009/0183105 | A1 | 7/2009 | Teel et al. |
| 2009/0183147 | A1 | 7/2009 | Davis et al. |
| 2009/0209938 | A1 | 8/2009 | Aalto-Setala |
| 2009/0210250 | A1 | 8/2009 | Prax et al. |
| 2009/0221890 | A1 | 9/2009 | Saffer et al. |
| 2009/0231249 | A1 | 9/2009 | Wang et al. |
| 2009/0270833 | A1 | 10/2009 | DeBelser |
| 2009/0275886 | A1 | 11/2009 | Blomquist et al. |
| 2009/0275896 | A1 | 11/2009 | Kamen et al. |
| 2009/0284691 | A1 | 11/2009 | Marhefka et al. |
| 2009/0292340 | A1 | 11/2009 | Mass et al. |
| 2009/0306573 | A1 | 12/2009 | Gagner et al. |
| 2009/0326340 | A1 | 12/2009 | Wang |
| 2009/0326516 | A1 | 12/2009 | Bangera et al. |
| 2010/0008377 | A1 | 1/2010 | Hasti et al. |
| 2010/0022988 | A1 | 1/2010 | Wochner |
| 2010/0036310 | A1 | 2/2010 | Hillman |
| 2010/0056992 | A1 | 3/2010 | Hayter |
| 2010/0083060 | A1 | 4/2010 | Rahman |
| 2010/0088507 | A1 | 4/2010 | Cho |
| 2010/0095229 | A1 | 4/2010 | Dixon et al. |
| 2010/0121170 | A1 | 5/2010 | Rule |
| 2010/0121246 | A1 | 5/2010 | Peters et al. |
| 2010/0121415 | A1 | 5/2010 | Skelton et al. |
| 2010/0121654 | A1 | 5/2010 | Portnoy et al. |
| 2010/0121752 | A1 | 5/2010 | Banigan et al. |
| 2010/0130933 | A1 | 5/2010 | Holland et al. |
| 2010/0131434 | A1 | 5/2010 | Magent et al. |
| 2010/0138523 | A1 | 6/2010 | Umess et al. |
| 2010/0146137 | A1 | 6/2010 | Wu et al. |
| 2010/0156633 | A1 | 6/2010 | Buck et al. |
| 2010/0160854 | A1 | 6/2010 | Gauthier |
| 2010/0160860 | A1 | 6/2010 | Celentano et al. |
| 2010/0174266 | A1 | 7/2010 | Estes |
| 2010/0191525 | A1 | 7/2010 | Rabenko et al. |
| 2010/0198034 | A1 | 8/2010 | Thomas et al. |
| 2010/0198196 | A1 | 8/2010 | Wei |
| 2010/0200506 | A1 | 8/2010 | Ware et al. |
| 2010/0209268 | A1 | 8/2010 | Davis |
| 2010/0212675 | A1 | 8/2010 | Walling et al. |
| 2010/0217621 | A1 | 8/2010 | Schoenberg |
| 2010/0234708 | A1 | 9/2010 | Buck et al. |
| 2010/0250732 | A1 | 9/2010 | Bucknell |
| 2010/0271479 | A1 | 10/2010 | Heydlauf |
| 2010/0273738 | A1 | 10/2010 | Valcke et al. |
| 2010/0274218 | A1 | 10/2010 | Yodfat et al. |
| 2010/0280486 | A1 | 11/2010 | Khair et al. |
| 2010/0292634 | A1 | 11/2010 | Kircher |
| 2010/0298765 | A1 | 11/2010 | Budiman et al. |
| 2010/0305499 | A1 | 12/2010 | Matsiev |
| 2010/0318025 | A1 | 12/2010 | John |
| 2011/0001605 | A1 | 1/2011 | Kiani et al. |
| 2011/0021898 | A1 | 1/2011 | Wei et al. |
| 2011/0028885 | A1 | 2/2011 | Eggers et al. |
| 2011/0040158 | A1 | 2/2011 | Katz et al. |
| 2011/0060758 | A1 | 3/2011 | Schlotterbeck et al. |
| 2011/0067092 | A1 | 3/2011 | Baker |
| 2011/0071844 | A1 | 3/2011 | Cannon et al. |
| 2011/0072379 | A1 | 3/2011 | Gannon |
| 2011/0078253 | A1 | 3/2011 | Chan et al. |
| 2011/0078608 | A1 | 3/2011 | Gannon et al. |
| 2011/0093284 | A1 | 4/2011 | Dicks et al. |
| 2011/0099313 | A1 | 4/2011 | Bolanowski |
| 2011/0106318 | A1 | 5/2011 | Ledford et al. |
| 2011/0125095 | A1 | 5/2011 | Lebel et al. |
| 2011/0133946 | A1 | 6/2011 | Kopp |
| 2011/0138185 | A1 | 6/2011 | Ju et al. |
| 2011/0166628 | A1 | 7/2011 | Jain |
| 2011/0175728 | A1 | 7/2011 | Baker, Jr. |
| 2011/0178462 | A1 | 7/2011 | Moberg et al. |
| 2011/0185010 | A1 | 7/2011 | Shatsky et al. |
| 2011/0196748 | A1 | 8/2011 | Caron et al. |
| 2011/0231216 | A1 | 9/2011 | Fyke et al. |
| 2011/0252230 | A1 | 10/2011 | Segre et al. |
| 2011/0257496 | A1 | 10/2011 | Terashima et al. |
| 2011/0257798 | A1 | 10/2011 | Ali et al. |
| 2011/0259954 | A1 | 10/2011 | Bartz et al. |
| 2011/0264043 | A1 | 10/2011 | Kotnick et al. |
| 2011/0264044 | A1 | 10/2011 | Bartz et al. |
| 2011/0266221 | A1 | 11/2011 | Ware et al. |
| 2011/0270045 | A1 | 11/2011 | Lebel et al. |
| 2011/0275904 | A1 | 11/2011 | Lebel et al. |
| 2011/0286457 | A1 | 11/2011 | Ee |
| 2011/0289162 | A1 | 11/2011 | Furlong |
| 2011/0289314 | A1 | 11/2011 | Whitcomb |
| 2011/0289497 | A1 | 11/2011 | Kiaie et al. |
| 2011/0295196 | A1 | 12/2011 | Chazot et al. |
| 2011/0295341 | A1 | 12/2011 | Estes et al. |
| 2011/0296051 | A1 | 12/2011 | Vange |
| 2011/0296411 | A1 | 12/2011 | Tang et al. |
| 2011/0313789 | A1 | 12/2011 | Karmen et al. |
| 2011/0319813 | A1 | 12/2011 | Kamen et al. |
| 2011/0320049 | A1 | 12/2011 | Chossat et al. |
| 2012/0005680 | A1 | 1/2012 | Dolby et al. |
| 2012/0011253 | A1 | 1/2012 | Friedman et al. |
| 2012/0016305 | A1 | 1/2012 | Jollota |
| 2012/0029941 | A1 | 2/2012 | Malave et al. |
| 2012/0036102 | A1 | 2/2012 | Fletcher et al. |
| 2012/0036550 | A1 | 2/2012 | Rodriguez |
| 2012/0066501 | A1 | 3/2012 | Xiong |
| 2012/0070045 | A1 | 3/2012 | Vesper et al. |
| 2012/0079084 | A1 | 3/2012 | Forssell et al. |
| 2012/0095437 | A1 | 4/2012 | Hemmerling |
| 2012/0112903 | A1 | 5/2012 | Kaib et al. |
| 2012/0130198 | A1 | 5/2012 | Beaule |
| 2012/0143116 | A1 | 6/2012 | Ware et al. |
| 2012/0150556 | A1 | 6/2012 | Galasso et al. |

(56) References Cited

U.S. PATENT DOCUMENTS

2012/0157920 A1 6/2012 Flachbart et al.
2012/0179135 A1 7/2012 Rinehart et al.
2012/0179136 A1 7/2012 Rinehart et al.
2012/0185267 A1 7/2012 Kamen et al.
2012/0203177 A1 8/2012 Lanier
2012/0210123 A1 8/2012 Castelnuovo
2012/0245554 A1 9/2012 Kawamura
2012/0259978 A1 10/2012 Petersen et al.
2012/0260012 A1 10/2012 Gao-Saari et al.
2012/0277716 A1 11/2012 Ali et al.
2012/0283630 A1 11/2012 Lee et al.
2012/0284734 A1 11/2012 McQuaid et al.
2012/0323212 A1 12/2012 Murphy
2012/0330380 A1 12/2012 Corndorf
2013/0006666 A1 1/2013 Schneider
2013/0006702 A1 1/2013 Wu
2013/0012877 A1 1/2013 Debelser et al.
2013/0012879 A1 1/2013 Debelser et al.
2013/0012880 A1 1/2013 Blomquist
2013/0015980 A1 1/2013 Evans et al.
2013/0036403 A1 2/2013 Geist
2013/0036412 A1 2/2013 Birtwhistle et al.
2013/0066265 A1 3/2013 Grant
2013/0072872 A1 3/2013 Yodfat et al.
2013/0091350 A1 4/2013 Gluck
2013/0096444 A1 4/2013 Condurso et al.
2013/0096648 A1 4/2013 Benson
2013/0102963 A1 4/2013 Marsh et al.
2013/0114594 A1 5/2013 Van Zijst
2013/0116578 A1 5/2013 An
2013/0132721 A1 5/2013 Busser
2013/0133083 A1 5/2013 Kurumai
2013/0138452 A1 5/2013 Cork et al.
2013/0150824 A1 6/2013 Estes et al.
2013/0167245 A1 6/2013 Birtwhistle et al.
2013/0173473 A1 7/2013 Birtwhistle et al.
2013/0191770 A1 7/2013 Bartz et al.
2013/0204188 A1 8/2013 Kamen et al.
2013/0218080 A1 8/2013 Peterfreund et al.
2013/0274669 A1 10/2013 Stempfle et al.
2013/0275539 A1 10/2013 Gross et al.
2013/0276785 A1 10/2013 Melker et al.
2013/0291116 A1 10/2013 Homer
2013/0296823 A1 11/2013 Melker et al.
2013/0296984 A1 11/2013 Burnett et al.
2013/0317753 A1 11/2013 Kamen et al.
2013/0346108 A1 12/2013 Kamen et al.
2014/0025392 A1 1/2014 Chandrasenan
2014/0108783 A1 4/2014 Suzuki
2014/0142540 A1 5/2014 Imhof
2014/0142963 A1 5/2014 Hill et al.
2014/0163517 A1 6/2014 Finan et al.
2014/0172994 A1 6/2014 Raumann et al.
2014/0180711 A1 6/2014 Kamen et al.
2014/0197950 A1 7/2014 Shupp et al.
2014/0215490 A1 7/2014 Mathur et al.
2014/0249500 A1 9/2014 Estes et al.
2014/0257251 A1 9/2014 Bush et al.
2014/0266790 A1 9/2014 Al-Ali et al.
2014/0266794 A1 9/2014 Brown et al.
2014/0269643 A1 9/2014 Sun
2014/0276571 A1 9/2014 Ludolph
2014/0280522 A1 9/2014 Watte
2014/0294177 A1 10/2014 Shastry et al.
2014/0297329 A1 10/2014 Rock
2014/0316819 A1 10/2014 Dunsirn et al.
2014/0318639 A1 10/2014 Peret et al.
2014/0366878 A1 12/2014 Baron
2014/0371543 A1 12/2014 Steinhauer et al.
2015/0005935 A1 1/2015 Bae et al.
2015/0006907 A1 1/2015 Brouwer et al.
2015/0025503 A1 1/2015 Searle
2015/0045729 A1 2/2015 Denzer et al.
2015/0058960 A1 2/2015 Schmoyer et al.
2015/0066531 A1 3/2015 Jacobson et al.
2015/0081894 A1 3/2015 Blomquist
2015/0100038 A1 4/2015 McCann et al.
2015/0100787 A1 4/2015 Westin et al.
2015/0117234 A1 4/2015 Raman et al.
2015/0151051 A1 6/2015 Tsoukalis
2015/0161354 A1 6/2015 Blomquist
2015/0196709 A1 7/2015 Jacobson et al.
2015/0199192 A1 7/2015 Borges et al.
2015/0199485 A1 7/2015 Borges et al.
2015/0207626 A1 7/2015 Neftel et al.
2015/0220890 A1 8/2015 Seshadri et al.
2015/0230760 A1 8/2015 Schneider
2015/0281128 A1 10/2015 Sindhu
2015/0325064 A1 11/2015 Downey
2015/0328396 A1 11/2015 Adams et al.
2015/0352301 A1 12/2015 Stedman et al.
2015/0365512 A1 12/2015 MacKenzie
2015/0371004 A1 12/2015 Jones
2015/0379237 A1 12/2015 Mills et al.
2016/0001003 A1 1/2016 Perazzo et al.
2016/0006695 A1 1/2016 Prodoehl et al.
2016/0015885 A1 1/2016 Pananen et al.
2016/0034655 A1 2/2016 Gray et al.
2016/0045661 A1 2/2016 Gray et al.
2016/0063471 A1 3/2016 Kobres et al.
2016/0119445 A1 4/2016 Hsieh
2016/0158437 A1 6/2016 Biasi et al.
2016/0204937 A1 7/2016 Edwards et al.
2016/0228633 A1 8/2016 Welsch et al.
2016/0241391 A1 8/2016 Fenster
2016/0277152 A1 9/2016 Xiang et al.
2016/0285876 A1 9/2016 Perez et al.
2016/0317742 A1 11/2016 Gannon et al.
2016/0321480 A1 11/2016 Hamlin
2016/0378618 A1 12/2016 Cmielowski
2017/0034277 A1 2/2017 Jackson et al.
2017/0041151 A1 2/2017 Kommireddy
2017/0054563 A1 2/2017 Verma
2017/0063559 A1 3/2017 Wallrabenstein
2017/0099148 A1 4/2017 Ochmanski et al.
2017/0104645 A1 4/2017 Wooton et al.
2017/0111301 A1 4/2017 Robinson
2017/0134357 A1 5/2017 Ohlsson
2017/0140134 A1 5/2017 Brough et al.
2017/0146381 A1 5/2017 Eckel et al.
2017/0149567 A1 5/2017 Moskal
2017/0149929 A1 5/2017 Moskal
2017/0214762 A1 7/2017 Swain et al.
2017/0258401 A1 9/2017 Volpe
2017/0258986 A1 9/2017 Tsoiukalis
2017/0262590 A1 9/2017 Karakosta et al.
2017/0325091 A1 11/2017 Freeman et al.
2017/0331804 A1 11/2017 Jellison et al.
2017/0351841 A1 12/2017 Moskal
2018/0063724 A1 3/2018 Zhang et al.
2018/0121613 A1 5/2018 Connely, IV et al.
2018/0122502 A1 5/2018 Jones et al.
2018/0126067 A1 5/2018 Ledford et al.
2018/0157821 A1 6/2018 Fan
2018/0181712 A1 6/2018 Ensey et al.
2018/0247712 A1 8/2018 Muhsin et al.
2018/0272117 A1 9/2018 Fangrow
2018/0278594 A1 9/2018 Schiffman et al.
2018/0317826 A1 11/2018 Muhsin et al.
2018/0322948 A1 11/2018 Drost et al.
2018/0359085 A1 12/2018 Dervyn
2019/0006044 A1 1/2019 Brask
2019/0030329 A1 1/2019 Hannaman et al.
2019/0036688 A1 1/2019 Wasily et al.
2019/0066831 A1 2/2019 Mairs et al.
2019/0096518 A1 3/2019 Pace
2019/0116160 A1 4/2019 Bhat et al.
2019/0132196 A1 5/2019 Trivedi et al.
2019/0166501 A1 5/2019 Debates et al.
2019/0172590 A1 6/2019 Vesto et al.
2019/0182349 A1 6/2019 Goel et al.
2019/0207965 A1 7/2019 Espinosa
2019/0229982 A1 7/2019 Ikuta et al.
2019/0244689 A1 8/2019 Atkin

(56) References Cited

U.S. PATENT DOCUMENTS

| | | | |
|---|---|---|---|
| 2019/0244707 | A1 | 8/2019 | Becker |
| 2019/0245942 | A1 | 8/2019 | Moskal |
| 2019/0272365 | A1 | 9/2019 | Huh |
| 2019/0311803 | A1 | 10/2019 | Kohlbrecher et al. |
| 2019/0328618 | A1 | 10/2019 | Hasegawa |
| 2019/0329056 | A1 | 10/2019 | Sjoquist et al. |
| 2019/0348160 | A1 | 11/2019 | Heavelyn et al. |
| 2019/0392929 | A1 | 12/2019 | Gassman |
| 2020/0023127 | A1 | 1/2020 | Simpson et al. |
| 2020/0051190 | A1 | 2/2020 | Kamen et al. |
| 2020/0054825 | A1 | 2/2020 | Kamen et al. |
| 2020/0118692 | A1 | 4/2020 | Booker et al. |
| 2020/0153627 | A1 | 5/2020 | Wentz |
| 2020/0206413 | A1 | 7/2020 | Silkaitis et al. |
| 2020/0213946 | A1 | 7/2020 | Kruse |
| 2020/0220865 | A1 | 7/2020 | Finger et al. |
| 2020/0280608 | A1 | 9/2020 | Borges |
| 2020/0282139 | A1 | 9/2020 | Susi |
| 2020/0334497 | A1 | 10/2020 | Barrett et al. |
| 2020/0351376 | A1 | 11/2020 | Moskal |
| 2020/0353168 | A1 | 11/2020 | Keenan et al. |
| 2020/0382323 | A1 | 12/2020 | Keselman |
| 2021/0008457 | A1 | 1/2021 | Schouviller et al. |
| 2021/0014259 | A1 | 1/2021 | Harris et al. |
| 2021/0045640 | A1 | 2/2021 | Poltorak |
| 2021/0136157 | A1 | 5/2021 | Kauppila et al. |
| 2021/0375438 | A1 | 12/2021 | Xavier et al. |
| 2021/0409362 | A1 | 12/2021 | Katis et al. |
| 2022/0037011 | A1 | 2/2022 | Fryman |
| 2022/0037012 | A1 | 2/2022 | Fryman |
| 2022/0054746 | A1 | 2/2022 | Patel et al. |
| 2022/0062541 | A1 | 3/2022 | Kamen et al. |
| 2022/0070221 | A1 | 3/2022 | Labudde et al. |
| 2022/0129452 | A1 | 4/2022 | Butler et al. |
| 2022/0150307 | A1 | 5/2022 | Walsh et al. |
| 2022/0165404 | A1 | 5/2022 | Vivek et al. |
| 2022/0189605 | A1 | 6/2022 | Kelly et al. |
| 2022/0191191 | A1 | 6/2022 | Brockhaus |
| 2022/0223283 | A1 | 7/2022 | Biasi et al. |
| 2022/0331513 | A1 | 10/2022 | Howard et al. |
| 2022/0384059 | A1 | 12/2022 | Xavier et al. |
| 2023/0009417 | A1 | 1/2023 | Xavier et al. |
| 2023/0108034 | A1 | 4/2023 | Fischer et al. |
| 2023/0139360 | A1 | 5/2023 | Kohlbrecher et al. |
| 2023/0145267 | A1 | 5/2023 | Xavier et al. |
| 2023/0147762 | A1 | 5/2023 | Xavier et al. |
| 2023/0231834 | A1 | 7/2023 | Carter |
| 2023/0253108 | A1 | 8/2023 | Dharwad et al. |
| 2023/0298768 | A1 | 9/2023 | Jacobson et al. |
| 2024/0047035 | A1 | 2/2024 | Ruchti et al. |
| 2024/0062867 | A1 | 2/2024 | Lim |
| 2024/0071609 | A1 | 2/2024 | Rohlwing |
| 2024/0293610 | A1 | 9/2024 | Jacobson |
| 2024/0321441 | A1 | 9/2024 | Rohlwing |
| 2024/0371508 | A1 | 11/2024 | Mills et al. |
| 2024/0424211 | A1 | 12/2024 | Day et al. |
| 2025/0232033 | A1 | 7/2025 | Vivek et al. |
| 2025/0381344 | A1 | 12/2025 | Wehba et al. |
| 2026/0012334 | A1 | 1/2026 | Dandekar et al. |
| 2026/0018280 | A1 | 1/2026 | Arrizza et al. |
| 2026/0054005 | A1 | 2/2026 | Day et al. |

FOREIGN PATENT DOCUMENTS

| | | | |
|---|---|---|---|
| CA | 2 060 151 | 8/1997 | |
| CA | 2 125 300 | 10/1999 | |
| CA | 2 630 102 | 10/2008 | |
| CA | 2 687 587 | 12/2008 | |
| CA | 2 897 897 | 7/2014 | |
| CA | 2 898 825 | 7/2014 | |
| CA | 2 900 564 | 10/2014 | |
| CA | 2 606 968 | 1/2020 | |
| CN | 1759398 | 4/2006 | |
| CN | 102521474 | 6/2012 | |
| CN | 103816582 | 5/2014 | |
| CN | 103920206 | 7/2014 | |
| CN | 102300501 | 4/2015 | |
| CN | 104487976 | 4/2015 | |
| CN | 106960128 | 7/2017 | |
| CN | 107810536 | 1/2023 | |
| DE | 31 12 762 | 1/1983 | |
| DE | 34 35 647 | 7/1985 | |
| DE | 198 44 252 | 3/2000 | |
| DE | 199 32 147 | 1/2001 | |
| DE | 10053116 A1 * | 5/2001 | ............. G16Z 99/00 |
| DE | 103 52 456 | 7/2005 | |
| EP | 0 319 267 | 6/1989 | |
| EP | 0 380 061 | 8/1990 | |
| EP | 0 384 155 | 8/1990 | |
| EP | 0 460 533 | 12/1991 | |
| EP | 0 564 127 | 6/1993 | |
| EP | 0 633 035 | 1/1995 | |
| EP | 0 652 528 | 5/1995 | |
| EP | 0 672 427 | 9/1995 | |
| EP | 0 683 465 | 11/1995 | |
| EP | 0 880 936 | 12/1998 | |
| EP | 1 050 993 | 11/2000 | |
| EP | 1 157 711 | 11/2001 | |
| EP | 1 174 817 | 1/2002 | |
| EP | 0 664 102 | 4/2002 | |
| EP | 1 197 178 | 4/2002 | |
| EP | 0 830 775 | 8/2002 | |
| EP | 1 500 025 | 4/2003 | |
| EP | 1 487 171 | 7/2007 | |
| EP | 1 933 497 | 6/2008 | |
| EP | 2 026 223 | 2/2009 | |
| EP | 2 113 842 | 11/2009 | |
| EP | 2 228 004 | 9/2010 | |
| EP | 2 243 506 | 10/2010 | |
| EP | 2 410 448 | 1/2012 | |
| EP | 2 742 961 | 6/2014 | |
| EP | 2 874 087 | 5/2015 | |
| ES | 2 371 995 | 1/2012 | |
| FR | 2 717 919 | 9/1995 | |
| GB | 2 285 135 | 6/1995 | |
| JP | 04-161139 | 6/1992 | |
| JP | 07-502678 | 3/1995 | |
| JP | 11-500643 | 1/1999 | |
| JP | 2000-316820 | 11/2000 | |
| JP | 2002-531154 | 9/2002 | |
| JP | 2003-016183 | 1/2003 | |
| JP | 2003-296173 | 10/2003 | |
| JP | 2003-308586 | 10/2003 | |
| JP | 2005-021463 | 1/2005 | |
| JP | 2005-527284 | 9/2005 | |
| JP | 2005-284846 | 10/2005 | |
| JP | 2006-047319 | 2/2006 | |
| JP | 2006-520949 | 9/2006 | |
| JP | 2007-518479 | 7/2007 | |
| JP | 2007-525256 | 9/2007 | |
| JP | 2008-080036 | 4/2008 | |
| JP | 2008-516303 | 5/2008 | |
| JP | 2008-158622 | 7/2008 | |
| JP | 2008-529675 | 8/2008 | |
| JP | 2009-163534 | 7/2009 | |
| JP | 2010-502361 | 1/2010 | |
| JP | 2011-506048 | 3/2011 | |
| JP | 2012-011204 | 1/2012 | |
| JP | 2012-070991 | 4/2012 | |
| JP | 2012-523895 | 10/2012 | |
| JP | 2013-179973 | 9/2013 | |
| JP | 2014-068283 | 4/2014 | |
| JP | 5647644 | 1/2015 | |
| TW | 200426656 | 12/2004 | |
| TW | I631966 | 8/2018 | |
| TW | M589351 | 1/2020 | |
| TW | M598505 | 7/2020 | |
| WO | WO 84/001719 | 5/1984 | |
| WO | WO 91/016416 | 10/1991 | |
| WO | WO 92/010985 | 7/1992 | |
| WO | WO 92/013322 | 8/1992 | |
| WO | WO 94/005355 | 3/1994 | |
| WO | WO 96/008755 | 3/1996 | |
| WO | WO 96/025186 | 8/1996 | |

(56) References Cited

FOREIGN PATENT DOCUMENTS

| | | |
|---|---|---|
| WO | WO 96/025963 | 8/1996 |
| WO | WO 98/012670 | 3/1998 |
| WO | WO 98/019263 | 5/1998 |
| WO | WO 99/051003 | 10/1999 |
| WO | WO 00/013580 | 3/2000 |
| WO | WO 00/053243 | 9/2000 |
| WO | WO 01/014974 | 3/2001 |
| WO | WO 01/033484 | 5/2001 |
| WO | WO 01/045014 | 6/2001 |
| WO | WO 01/083007 | 11/2001 |
| WO | WO 02/005702 | 1/2002 |
| WO | WO 02/036044 | 5/2002 |
| WO | WO 02/049153 | 6/2002 |
| WO | WO 02/049279 | 6/2002 |
| WO | WO 02/069099 | 9/2002 |
| WO | WO 02/081015 | 10/2002 |
| WO | WO 02/088875 | 11/2002 |
| WO | WO 03/006091 | 1/2003 |
| WO | WO 03/023551 | 3/2003 |
| WO | WO 03/050917 | 6/2003 |
| WO | WO 03/091836 | 11/2003 |
| WO | WO 03/094092 | 11/2003 |
| WO | WO 2004/060455 | 7/2004 |
| WO | WO 2004/070557 | 8/2004 |
| WO | WO 2004/070562 | 8/2004 |
| WO | WO 2004/072828 | 8/2004 |
| WO | WO 2005/036447 | 4/2005 |
| WO | WO 2005/057175 | 6/2005 |
| WO | WO 2005/066872 | 7/2005 |
| WO | WO 2007/087443 | 8/2007 |
| WO | WO 2007/117705 | 10/2007 |
| WO | WO 2007/127879 | 11/2007 |
| WO | WO 2007/127880 | 11/2007 |
| WO | WO 2008/059495 | 5/2008 |
| WO | WO 2008/064254 | 5/2008 |
| WO | WO 2008/067245 | 6/2008 |
| WO | WO 2008/082854 | 7/2008 |
| WO | WO 2008/088490 | 7/2008 |
| WO | WO 2008/097316 | 8/2008 |
| WO | WO 2008/103915 | 8/2008 |
| WO | WO 2008/124478 | 10/2008 |
| WO | WO 2008/134146 | 11/2008 |
| WO | WO 2009/016504 | 2/2009 |
| WO | WO 2009/023406 | 2/2009 |
| WO | WO 2009/023407 | 2/2009 |
| WO | WO 2009/023634 | 2/2009 |
| WO | WO 2009/036327 | 3/2009 |
| WO | WO 2009/049252 | 4/2009 |
| WO | WO 2010/017279 | 2/2010 |
| WO | WO 2010/033919 | 3/2010 |
| WO | WO 2010/053703 | 5/2010 |
| WO | WO 2010/075371 | 7/2010 |
| WO | WO 2010/099313 | 9/2010 |
| WO | WO 2010/114929 | 10/2010 |
| WO | WO 2010/119409 | 10/2010 |
| WO | WO 2010/124127 | 10/2010 |
| WO | WO 2010/130992 | 11/2010 |
| WO | WO 2010/135646 | 11/2010 |
| WO | WO 2010/135654 | 11/2010 |
| WO | WO 2010/135686 | 11/2010 |
| WO | WO 2011/005633 | 1/2011 |
| WO | WO 2011/022549 | 2/2011 |
| WO | WO 2012/048833 | 4/2012 |
| WO | WO 2012/049214 | 4/2012 |
| WO | WO 2012/049218 | 4/2012 |
| WO | WO 2012/120078 | 9/2012 |
| WO | WO 2012/140547 | 10/2012 |
| WO | WO 2012/164556 | 12/2012 |
| WO | WO 2012/170942 | 12/2012 |
| WO | WO 2013/025394 | 2/2013 |
| WO | WO 2013/045506 | 4/2013 |
| WO | WO 2014/100557 | 6/2014 |
| WO | WO 2014/100687 | 6/2014 |
| WO | WO 2014/100736 | 6/2014 |
| WO | WO 2014/131729 | 9/2014 |
| WO | WO 2014/131730 | 9/2014 |
| WO | WO 2015/047595 | 4/2015 |
| WO | WO 2015/124569 | 8/2015 |
| WO | WO 2016/099551 | 6/2016 |
| WO | WO 2016/179389 | 11/2016 |
| WO | WO 2017/200989 | 11/2017 |
| WO | WO 2019/219290 | 11/2019 |
| WO | WO 00/003344 | 1/2020 |
| WO | WO 2020/227403 | 11/2020 |
| WO | WO 2021/201884 | 10/2021 |
| WO | WO 2022/006014 | 1/2022 |
| WO | WO 2022/051230 | 3/2022 |
| WO | WO 2023/044335 | 3/2023 |
| WO | WO 2023/159134 | 8/2023 |
| WO | WO 2024/196590 | 9/2024 |
| WO | WO 2025/122515 | 6/2025 |

OTHER PUBLICATIONS

Amano et al., "A Remote Drip Infusion Monitoring System Employing Bluetooth," 2012 Annual International Conference of the IEEE Engineering in Medicine and Biology Society, pp. 2029-2032.

Wang et al., "Infusion Monitoring System Based on Wireless Transmission", 2011 4th IEEE International Symposium on Microwave, Antenna, Propagation and EMC Technologies for Wireless Communications, pp. 656-659.

International Search Report and Written Opinion received in PCT Application No. PCT/US2012/061055, dated Jan. 7, 2013 in 9 pages.

International Preliminary Report on Patentability and Written Opinion received in PCT Application No. PCT/US2012/061055, dated May 1, 2014 in 8 pages.

Ahn et al., "Towards Scalable Authentication in Health Services", Eleventh IEEE International Workshops on Enabling Technologies: Infrastructure for Collaborative Enterprises, Jun. 2002, pp. 83-88.

Akridge, Jeannie, "New Pumps Outsmart User Error", Healthcare Purchasing News, Apr. 2011, pp. 10, <http://web.archive.org/web/20110426122450/http://www.hpnonline.com/inside/2011-04/1104-OR-Pumps.html>.

Alur et al., "Formal Specifications and Analysis of the Computer-Assisted Resuscitation Algorithm (CARA) Infusion Pump Control System", International Journal on Software Tools for Technology Transfer, Feb. 2004, vol. 5, No. 4, pp. 308-319.

Aragon, Daleen RN, Ph.D., CCRN, "Evaluation of Nursing Work Effort and Perceptions About Blood Glucose Testing in Tight Glycemic Control", American Journal of Critical Care, Jul. 2006, vol. 15, No. 4, pp. 370-377.

ASHP Advantage, "Improving Medication Safety in Health Systems Through Innovations in Automation Technology", Proceedings of Educational Symposium and Educational Sessions during the 39th ASHP Midyear Clinical Meeting, Dec. 5-9, 2004, Orlando, FL, pp. 28.

Banerjee et al., "Token-Based Authentication Techniques on Open Source Cloud Platforms", Sistemas y Telemática, vol. 16, No. 47, 2018, pp. 17.

Beard et al., "Total Quality Pain Management: History, Background, Resources", Abbott Laboratories, TQPM Survey History, available Feb. 2015 or earlier, pp. 1-3.

Bektas et al., "Bluetooth Communication Employing Antenna Diversity", Proceedings of Eight IEEE International Symposium on Computers and Communication, Jul. 2003, pp. 6.

Bellare et al., "Security Proofs for Identity-Based Identification and Signature Schemes", Lecture Notes in Computer Science, Jan. 2009, vol. 22, No. 1, pp. 18.

Bequette, Ph.D., "A Critical Assessment of Algorithms and Challenges in the Development of a Closed-Loop Artificial Pancreas", Diabetes Technology & Therapeutics, Feb. 28, 2005, vol. 7, No. 1, pp. 28-47.

Bequette, B. Wayne, Ph.D., "Analysis of Algorithms for Intensive Care Unit Blood Glucose Control", Journal of Diabetes Science and Technology, Nov. 2007, vol. 1, No. 6, pp. 813-824.

(56) References Cited

OTHER PUBLICATIONS

Block, Alexander, "Secret Sharing and 1-11 Threshold Signatures with BLS", Jul. 2, 2018, https://blog.dash.org/secret-sharing-and-threshold-signatures-with-bls-954d1587b5f, in 8 pages.
Braun, "Infusomat® Space and Accessories", Instructions for Use, Nov. 2010, pp. 68. <http://corp.bbraun.ee/Extranet/Infusionipumbad/Kasutusjuhendid/Vanad/Kasutusjuhend-Infusomat_Space(vers688J,inglise_k).pdf>.
Brownlee, Seth, "Product Spotlight: The Plum A+ with Hospira MedNet Infusion System", PP&P Magazine, Dec. 2005, vol. 2, No. 7, pp. 2.
Cannon, MD et al., "Automated Heparin-Delivery System to Control Activated Partial Thromboplastin Time", Circulation, Feb. 16, 1999, vol. 99, pp. 751-756.
Cardinal Health, "Alaris® Syringe Pumps" Technical Service Manual, Copyright 2002-2006, Issue 9, pp. 1-88, <http://www.frankshospitalworkshop.com/equipment/documents/infusion_pumps/service_manuals/Cardinal_Alaris_-_Service_Manual.pdf>.
"CareAware® Infusion Management", Cerner Store, as printed May 12, 2011, pp. 3, <https://store.cerner.com/items/7>.
Chan, Katherine Yin-Yee. "Mitigating Risks Associated with Secondary Intravenous Infusions: An Empirical Evaluation of a Technology-Based, Training-Based, and Practice-Based Intervention." Order No. 1570719 University of Toronto (Canada), 2013. Ann Arbor: ProQuest. Web. Nov. 23, 2024, pp. 182.
Chen et al., "Enabling Location-Based Services on Wireless LANs", The 11th IEEE International Conference on Networks, ICON 2003, Sep. 28-Oct. 1, 2003, pp. 567-572.
Cloudflare, "What Happens in a TLS Handshake? | SSL Handshake", as archived May 19, 2020, https://web.archive.org/web/20200519192121/https:/www.cloudflare.com/en-au/learning/ssl/what-happens- in-a-tls-handshake/, 4 pages.
"Computer Dictionary", Microsoft Press, Third Edition, Microsoft Press, 1997, pp. 430 & 506.
"Context-Free Grammar", Wikipedia.org, as last modified Mar. 5, 2010 in 11 pages, <https://en.wikipedia.org/w/index.php/?title=Context-free_grammar&oldid=347915989>.
Crawford, Anne J., MSN, RNC, "Building a Successful Quality Pain Service: Using Patient Satisfaction Data and the Clinical Practice Guideline", USA, 1995, pp. 1-6.
Crocker et al., "Augmented BNF for Syntax Specifications: ABNF", Network Working Group, Standards Track, Jan. 2008, pp. 16.
Davidson et al., "A Computer-Directed Intravenous Insulin System Shown to be Safe, Simple, and Effective in 120,618 h of Operation", Diabetes Care, Oct. 2005, vol. 28, No. 10, pp. 2418-2423.
Davies, T., "Cordless Data Acquisition in a Hospital Environment", IEE Colloquium on Cordless Computing—Systems and User Experience, 1993, pp. 4.
Dayhoff et al., "Medical Data Capture and Display: The Importance of Clinicians' Workstation Design", AMIA, Inc., 1994, pp. 541-545.
Diabetes Close Up, Close Concerns AACE Inpatient Management Conference Report, Consensus Development Conference on Inpatient Diabetes and Metabolic Control, Washington, D.C., Dec. 14-16, 2003, pp. 1-32.
Doesburg et al., "Improved Usability of a Multi-Infusion Setup Using a Centralized Control Interface: A Task-Based Usability Test", Aug. 11, 2017, PLoS ONE, vol. 12, No. 8, pp. 10.
"Download", Free On-Line Dictionary of Computing, as archived Jun. 16, 2010 in 1 page, http://web.archive.org/web/20100616010314/https://foldoc.org/download.
East PhD et al., "Digital Electronic Communication Between ICU Ventilators and Computers and Printers", Respiratory Care, Sep. 1992, vol. 37, No. 9, pp. 1113-1122.
Edworthy, Judy, "Medical Audible Alarms: A Review", Journal of the American Medical Informatics Association, vol. 20, No. 3, 2013, pp. 584-589.
Einhorn, George W., "Total Quality Pain Management: A Computerized Quality Assessment Tool for Postoperative Pain Management", Abbott Laboratories, Chicago, IL, Mar. 2, 2000, pp. 1-4.
Eskew et al., "Using Innovative Technologies to Set New Safety Standards for the Infusion of Intravenous Medications", Hospital Pharmacy, 2002, vol. 37, No. 11, pp. 1179-1189.
Fan et al., "Smart Medication Delivery Systems: Infusion Pumps", Supplementary Report, Healthcare Human Factors, Feb. 26, 2010, pp. 94.
Felleiter et al., "Data Processing in Prehospital Emergency Medicine", International journal of Clinical Monitoring and Computing, Feb. 1995, vol. 12, No. 1, pp. 37-41.
"File Verification", Wikipedia.org, as last modified Oct. 11, 2011 in 2 pages, <https://en.wikipedia.org/w/index.php?title=File_verification&oldid=455048290>.
Fogt et al., Development and Evaluation of a Glucose Analyzer for a Glucose-Controlled Insulin Infusion System (Biostator®), Clinical Chemistry, 1978, vol. 24, No. 8, pp. 1366-1372.
Gabel et al., "Camp: A Common API for Measuring Performance", 21st Large Installations System Administration Conference (LISA '07), 2007, pp. 49-61.
Gage et al., "Automated Anesthesia Surgery Medical Record System", International Journal of Clinical Monitoring and Computing, Dec. 1990, vol. 7, No. 4, pp. 259-263.
Galt et al., "Personal Digital Assistant-Based Drug Information Sources: Potential to Improve Medication Safety", Journal of Medical Library Association, Apr. 2005, vol. 93, No. 2, pp. 229-236.
Gardner, Ph.D. et al., "Real Time Data Acquisition: Recommendations for the Medical Information Bus (MIB)", 1992, pp. 813-817.
"General-Purpose Infusion Pumps", Health Devices, ECRI Institute, Oct. 1, 2002, vol. 31, No. 10, pp. 353-387.
Givens et al., "Exploring the Internal State of User Interfaces by Combining Computer Vision Techniques with Grammatical Inference", Proceedings of the 2013 International Conference on Software Engineering, San Francisco, CA, May 18-26, 2013, pp. 1165-1168.
Glaeser, "A Hierarchical Minicomputer System for Continuous Post-Surgical Monitoring", Computers and Biomedical Research, Aug. 31, 1975, pp. 336-361.
Goldberg et al., "Clinical Results of an Updated Insulin Infusion Protocol in Critically Ill Patients", Diabetes Spectrum, 2005, vol. 18, No. 3, pp. 188-191.
Gomez et al., "CLAM: Connection-Less, Lightweight, and Multiway Communication Support for Distributed Computing", Computer Science, 1997, vol. 1199, pp. 227-240.
"GPS Tracker for Medical Equipment", <http://www.trackingsystem.com/forbusinesses/corporate-trackingsystem/1098-gps-tracker-formedicalequipment.html>, Mar. 15, 2015, pp. 2.
Graseby, "Model 3000/500 and Micro 3100/505: Volumetric Infusion Pump", Technical Service Manual, Graseby Medical Ltd., Apr. 2002, Issue A, pp. 160.
Graseby, "Model 3000/500 and Micro 3100/505: Volumetric Infusion Pump: Illustrated Parts List for Pump Serial Numbers from 3000 to 59,999", Technical Service Manual, Graseby Medical Ltd., Apr. 2002, Issue A, pp. 71.
Gutwin et al., "Gone but Not Forgotten: Designing for Disconnection in Synchronous Groupware", CSCW 2010, Feb. 6-10, 2010, Savannah, Georgia, USA., pp. 179-188.
Halpern et al., "Changes in Critical Care Beds and Occupancy in the United States 1985-2000: Differences Attributable to Hospital Size", Critical Care Medical, Aug. 2006, vol. 34, No. 8, pp. 2105-2112.
Hamann et al., "Pumpsim: A Software Package for Simulating Computer-Controlled Drug Infusion Pumps", Annual International Conference of the IEEE Engineering in Medicine and Biology Society, 1990, vol. 12, No. 5, pp. 2019-2020.
Hasegawa et al., "On a Portable Memory Device for Physical Activities and Informations of Maternal Perception", Journal of Perinatal Medicine, 1988, vol. 16, No. 4, pp. 349-356.
Hawley et al., "Clinical Implementation of an Automated Medical Information Bus in an Intensive Care Unit", Proceedings of the Annual Symposium on Computer Application in Medical Care, Nov. 9, 1988, pp. 621-624.
Hayes-Roth et al., "Guardian: A Prototype Intelligent Agent for Intensive-Care Monitoring", Artificial Intelligence in Medicine, vol. 4, Dec. 31, 1992, pp. 165-185.

(56) References Cited

OTHER PUBLICATIONS

Hospira, GemStar® Pain Management Infusion System 9-084-PR1-2-2, <www.hospira.com/products/gemstar_painmanagement.aspx>, Jan. 28, 2010, pp. 1-2.

Huang et al., "Secure Identity-Based Data Sharing and Profile Matching for Mobile Healthcare Social Networks in Cloud Computing", vol. 6, Jul. 2018, pp. 36584-36594.

Introducing Abbott TQPM (Total Quality Pain Management), Abbott Laboratories, Abbott Park, IL, May 2000, pp. 1-4.

"Infusion Pump", Wikipedia.org, as last modified Mar. 27, 2014, in 3 pages, <https://web.archive.org/web/20140703024932/https://en.wikipedia.org/wiki/Infusion_pump>.

Isaka et al., "Control Strategies for Arterial Blood Pressure Regulation", IEEE Transactions on Biomedical Engineering, Apr. 1993, vol. 40, No. 4, pp. 353-363.

Johnson et al., "Using BCMA Software to Improve Patient Safety in Veterans Administration Medical Centers", Journal of Healthcare Information Management, Dec. 6, 2004, vol. 16, No. 1, pp. 46-51.

Kent Displays, "Reflex™ Electronic Skins", Product Brief 25127B, 2009, pp. 2.

Kent Displays, "Reflex Electronic Skins Engineering Evaluation Kit", 25136A, Mar. 10, 2009.

Lefkowitz et al., "A Trial of the Use of Bar Code Technology to Restructure a Drug Distribution and Administration System", Hospital Pharmacy, Mar. 31, 1991, vol. 26, No. 3, pp. 239-242.

Lenssen et al., "Bright Color Electronic Paper Technology and Applications", IDS '09 Publication EP1-2 (Phillips Research), 2009, pp. 529-532.

Leveson, Nancy, "Medical Devices: The Therac-25", Appendix A, University of Washington, 1995, pp. 49.

Li et al., "Hijacking an Insulin Pump: Security Attacks and Defenses for a Diabetes Therapy System", 2011 IEEE 13th International Conference on e-Health Networking, Applications and Services, 2011, pp. 150-156.

Linkens, D.A. "Computer Control for Patient Care", Computer Control of Real-Time Processes, IEE Control Engineering Series 41, 1990, Ch. 13, pp. 216-238.

Mako Hill et al., "The Official Ubuntu Book", Shoeisha Co., Ltd., 1st Edition, Jun. 11, 2007, pp. 115 to 125.

Marshall, et al., "New Microprocessor-Based Insulin Controller", IEEE Transactions on Biomedical Engineering, Nov. 1983, vol. BME-30, No. 11, pp. 689-695.

Martino et al., "Automation of a Medical Intensive Care Environment with a Flexible Configuration of Computer Systems", Proceedings of the Annual Symposium on Computer Application in Medical Care, Nov. 5, 1980, vol. 3, pp. 1562-1568.

Matsunaga et al., "On the Use of Machine Learning to Predict the Time and Resources Consumed by Applications", 2010 10th IEEE/ACM International Conference on Cluster, Cloud and Grid Computing (CCGrid), May 17-20, 2010, pp. 495-504.

Mauseth et al., "Proposed Clinical Application for Tuning Fuzzy Logic Controller of Artificial Pancreas Utilizing a Personalization Factor", Journal of Diabetes Science and Technology, Jul. 2010, vol. 4, No. 4, pp. 913-922.

"McKesson Automation and ALARIS Medical Systems Developing Point-of-Care Bar Coding Solution to Improve IV Medication Safety", PR Newswire, NY, Dec. 9, 2002, pp. 4.

Medfusion™, "Medfusion Syringe Infusion Pump Model 4000", Operator's Manual, Software Version V1.1, Sep. 2011, pp. 154. <http://www.medfusionpump.com/assets/literature/manuals/Operators_Manual_4000_40-5760-51A.pdf>.

Metnitz et al., "Computer Assisted Data Analysis in Intensive Care: the ICDEV Project-Development of a Scientific Database System for Intensive Care", International Journal of Clinical Monitoring and Computing, Aug. 1995, vol. 12, No. 3, pp. 147-159.

Michienzi, Kelly, "Managing Drug Library Updates", Pharmacy Purchasing Products, https://www.pppmag.com/article/1061, Feb. 2012, vol. 9, pp. 22-23.

Micrel Medical Devices, "MP Daily +" <http://web.archive.org/web/20130803235715/http://www.micrelmed.com/index.aspx?productid=9> as archived Aug. 3, 2013 in 1 page.

Moghissi, Etie, MD, FACP, FACE, "Hyperglycemia in Hospitalized Patients", A Supplement to ACP Hospitalist, Jun. 15, 2008, pp. 32.

Murphy, Robert, "The Design of Safety-Critical Medical Infusion Devices", May 30, 2007, Doctor of Philosophy submission, pp. 317.

Murray, Jr. et al., "Automated Drug Identification System (during surgery)", IEEE Proceedings of Southeastcon '91, Apr. 7-10, 1991, pp. 265.

Nicholson et al., "'Smart' Infusion Apparatus for Computation and Automated Delivery of Loading, Tapering, and Maintenance Infusion Regimens of Lidocaine, Procainamide, and Theophylline", Proceedings of the Seventh Annual Symposium on Computer Applications in Medical Care, Oct. 1983, pp. 212-213.

Nojoumian et al., "Social Secret Sharing in Cloud Computing Using a New Trust Function", 2012 Tenth Annual International Conference on Privacy, Security and Trust, pp. 161-167.

Nolan et al., "The P1073 Medical Information Bus Standard: Overview and Benefits for Clinical Users", 1990, pp. 216-219.

O'Brien et al., "Securing wireless infusion pumps", NIST Special Publication (1800): 8B, 2018, pp. 85.

Omnilink Systems, Inc., "Portable Medical Equipment Tracking", <http://www.omnilink.com/portablemedicalequipmenttracking/>, Mar. 15, 2015, pp. 2.

O'Shea, Kristen L., "Infusion Management: Working Smarter, Not Harder", Hospital Pharmacy, Apr. 2013, vol. 48, No. 3, pp. S1-S14.

Package Management in Debian GNU/Linux, Debian GNU/Linux Expert Desktop Use Special, Giutsu-Hyohron Co., Ltd., First Edition, Sep. 25, 2004, pp. 183-185.

Passos et al., "Distributed Software Platform for Automation and Control of General Anaesthesia", Eighth International Symposium on Parallel and Distributed Computing, ISPDC '09, Jun. 30-Jul. 4, 2009, pp. 8.

Phillips, "IntelliSpace Event Management and IntelliVue Patient Monitoring", Release 10, 2011, <http://incenter.medical.philips.com/doclib/enc/fetch/2000/4504/577242/577243/577247/582646/583147/8359175/Philips_Patient_Monitoring_and_IntelliSpace_Event_Management_Interoperability.pdf%3fnodeid%3d8508574%26vernum%3d-2>, pp. 2.

Pretty et al., "Hypoglycemia Detection in Critical Care Using Continuous Glucose Monitors: An in Silico Proof of Concept Analysis", Journal of Diabetes Science and Technology, Jan. 2010, vol. 4, No. 1, pp. 15-24.

Rahmani et al., "Smart e-Health Gateway: Bringing Intelligence to Internet-of-Things Based Ubiquitous Healthcare Systems", 2015 12th Annual IEEE Consumer Communications and Networking Conference (CCNC), Jul. 2015, pp. 826-834.

Rappoport, Arthur E., "A Hospital Patient and Laboratory machine-Readable Identification System (MRIS) Revisited", Journal of Medical Systems, Apr. 1984, vol. 8, Nos. 1/2, pp. 133-156.

Ritchie et al., "A Microcomputer Based Controller for Neuromuscular Block During Surgery", Annals of Biomedical Engineering, Jan. 1985, vol. 13, No. 1, pp. 3-15.

Saager et al., "Computer-Guided Versus Standard Protocol for Insulin Administration in Diabetic Patients Undergoing Cardiac Surgery", Annual Meeting of the American Society of Critical Care Anesthesiologists, Oct. 13, 2006.

Sabir et al., "Authentication Model Based on JWT and Local PKI for Communication Security in Multi-agent Systems", International Conference Europe Middle East & North Africa Information Systems and Technologies to Support Learning. Springer, Cham, 2019, pp. 469-479.

Sanders et al., "The Computer in a Programmable Implantable Medication System (PIMS)", Proceedings of the Annual Symposium on Computer Application in Medical Care, Nov. 2, 1982, pp. 682-685.

Schilling et al., "Optimizing Outcomes! Error Prevention and Evidence-Based Practice with IV Medications", A Pro-Ce Publication, Hospira, Inc., Feb. 6, 2012, pp. 56.

Schulze et al., "Advanced Sensors Technology Survey", Final Report, Feb. 10, 1992, pp. 161.

(56) References Cited

OTHER PUBLICATIONS

Scott, et al., "Using Bar-Code Technology to Capture Clinical Intervention Data in a Hospital with a Stand-Alone Pharmacy Computer System", Mar. 15, 1996, American Journal of Health-System Pharmacy, vol. 53, No. 6, pp. 651-654.
Sebald et al., "Numerical Analysis of a Comprehensive in Silico Subcutaneous Insulin Absorption Compartmental Model", 31st Annual International Conference of the IEEE Engineering in Medicine and Biology Society, Sep. 2-6, 2009, pp. 3901-3904.
Sethia et al., "Security Framework for Portable NFC Mobile Based Health Record System", Oct. 2016, IEEE 12th International Conference on Wireless and Mobile Computing, Networking and Communications, pp. 1-8.
Shabot, M. Michael, "Standardized Acquisition of Bedside Data: The IEEE P1073 Medical Information Bus", International Journal of Clinical Monitoring and Computing, vol. 6, Sep. 27, 1989, pp. 197-204.
Sheppard, Louis, Ph.D., "Automation of the Infusion of Drugs Using Feedback Control", Journal of Cardiothoracic and Vascular Anesthesia, Feb. 28, 1989, vol. 3, No. 1, pp. 1-3.
Sheppard, Louis, Ph.D., "Computer Control of the Infusion of Vasoactive Drugs", Annals of Biomedical Engineering, Jul. 1980, vol. 8, No. 4-6, pp. 431-444.
Sheppard, Louis, Ph.D., "The Application of Computers to the Measurement, Analysis, and Treatment of Patients Following Cardiac Surgical Procedures", The University of Alabama in Birmingham, Oct. 31, 1977, pp. 297-300.
Sheppard, Louis, Ph.D., "The Computer in the Care of Critically Ill Patients", Proceedings of the IEEE, Sep. 1979, vol. 67, No. 9, pp. 1300-1306.
"Sigma Spectrum: Operator's Manual", May 15, 2008, pp. 63. <https://usme.com/content/manuals/sigma-spectrum-operator-manual.pdf>.
"Sigma Spectrum: Operator's Manual", Oct. 2009, pp. 72. <http://static.medonecapital.com/manuals/userManuals/Sigma-Spectrum-Operator-Manual-October-2009.pdf>.
Simonsen, Michael Ph.D., POC Testing, New Monitoring Strategies on Fast Growth Paths in European Healthcare Arenas, Biomedical Business & Technology, Jan. 2007, vol. 30, No. 1, pp. 1-36.
Siv-Lee et al., "Implementation of Wireless 'Intelligent' Pump IV Infusion Technology in a Not-for-Profit Academic Hospital Setting", Hospital Pharmacy, Sep. 2007, vol. 42, No. 9, pp. 832-840. <http://www.thomasland.com/hpj4209-832.pdf>.
Slack, W.V., "Information Technologies for Transforming Health Care", <https://www.andrew.cmu.edu/course/90-853/medis.dir/otadocs.dir/03ch2.pdf>, Ch. 2, 1995, pp. 29-78.
Smith, Joe, "Infusion Pump Informatics", CatalyzeCare: Transforming Healthcare, as printed May 12, 2011, pp. 2.
Sodders, Lisa, "VA Center Keeps Medicine in Right Hands", The Capital-Journal, Dec. 4, 1999, pp. 1-2.
"Software Versioning", Wikipedia.org, dated Oct. 16, 2011 in 11 pages, <https://en.wikipedia.org/w/index.php?title=Software_versioning&oldid=455859110>.
Solapurkar et al., "Building Secure Healthcare Services Using OAuth 2.0 and JSON Web Token in IOT Cloud Scenario", Dec. 2016, 2nd International Conference on Contemporary Computing and Informatics, pp. 99-10.
Stack Exchange, "Avoiding SSL handshake for each call", as archived Sep. 22, 2021, https://web.archive.org/web/20210922184153/https:/security.stackexchange.com/questions/56623/avoiding-ssl-handshake-for-each-call, 3 pages.
Stitt, F.W., "The Problem-Oriented Medical Synopsis: a Patient-Centered Clinical Information System", Proceedings of the Annual Symposium on Computer Application in Medical Care, 1994, pp. 88-92.
Stokowski, Laura A. RN, MS, "Using Technology to Improve Medication Safety in the Newborn Intensive Care Unit", Advances in Neonatal Care, Dec. 2001, vol. 1, No. 2, pp. 70-83.
Sutton et al., "The Syntax and Semantics of the PROforma Guideline Modeling Language", Journal of the American Medical Informatics Association, Sep./Oct. 2003, vol. 10, No. 5, pp. 433-443.
Szeinbach et al., "Automated Dispensing Technologies: Effect on Managed Care", Journal of Managed Care Pharmacy (JMCP), Sep./Oct. 1995, vol. 1, No. 2, pp. 121-127.
Szolovits et al., "Guardian Angel: Patient-Centered Health Information Systems", Technical Report MIT/LCS/TR-604, Massachusetts Institute of Technology Laboratory for Computer Science, May 1994, pp. 39.
"TCG TPM v2.0 Provisioning Guidance", Reference, Version 1, Revision 1, Mar. 15, 2017, pp. 1-43.
Van Den Berghe, M.D., Ph.D., et al., "Intensive Insulin Therapy in Critically Ill Patients", The New England Journal of Medicine, Nov. 8, 2001, vol. 345, No. 19, pp. 1359-1367.
Van Den Berghe, M.D., Ph.D., et al., "Intensive Insulin Therapy in the Medical ICU", The New England Journal of Medicine, Feb. 2, 2006, vol. 354, No. 5, pp. 449-461.
Van Der Maas et al., "Requirements for Medical Modeling Languages", Journal of the American Medical Informatics Association, Mar./Apr. 2001, vol. 8, No. 2, pp. 146-162.
Villalobos et al., "Computerized System in Intensive Care medicine", Medical Informatics, vol. 11, No. 3, 1986, pp. 269-275.
Wilkins et al., "A Regular Language: The Annotated Case Report Form", PPD Inc., PharmaSUG2011—Paper CD18, 2011, pp. 1-9.
Ying et al., "Regulating Mean Arterial Pressure in Postsurgical Cardiac Patients. A Fuzzy Logic System to Control Administration of Sodium Nitroprusside", IEEE Engineering in Medicine and Biology Magazine, vol. 13, No. 5, Nov.-Dec. 1994, pp. 671-677.
Yoo et al., "Code-Based Authentication Scheme for Lightweight Integrity Checking of Smart Vehicles", IEEE Access, 2018, vol. 6, pp. 46731-46741.
Yue, Ying Kwan, "A Healthcare Failure Mode and Effect Analysis on the Safety of Secondary Infusions", Thesis, Institute of Biomaterials and Biomedical Engineering, University of Toronto, 2012, pp. 168.
Yurkonis et al., "Computer Simulation of Adaptive Drug Infusion", IEEE Transactions on Biomedical Engineering, vol. BME-34, No. 8, Aug. 1987, pp. 633-635.
Zakariah et al., "Combination of Biphasic Transmittance Waveform with Blood Procalcitonin Levels for Diagnosis of Sepsis in Acutely Ill Patients", Critical Care Medicine, 2008, vol. 36, No. 5, pp. 1507-1512.
Reexamination Application 90/015,392, Filed Jul. 17, 2025, Carefusion 303, Inc (Patent Owner).
Reexamination Application 90/015,419, Filed Jul. 31, 2025, Carefusion 303, Inc (Patent Owner).
Marinkovic et al., "Ultra Low Power Signal Oriented Approach for Wireless Health Monitoring", Sensors, 2012, vol. 12, pp. 7917-7937.
Shah et al., "Implementation of Smart Infusion Pumps: A Scoping Review and Case Study Discussion of the Evidence of the Role of the Pharmacist", Pharmacy, 2020, vol. 8, No. 239, pp. 13.

* cited by examiner

MEDICAL DEVICE UPDATE SYSTEM

BACKGROUND OF THE INVENTION

Field of the Invention

This disclosure relates in general to medical devices. More particularly, the present disclosure relates to a novel system and method for updating software and configuration files in medical devices, such as infusion pumps.

Description of the Related Art

Intravenous infusion therapy is prescribed where it is desirable to administer medications and other fluids directly into the circulatory system of a patient. Some conventional infusion pumps are provided with a hospital customized drug library and warn the clinician when they are trying to enter or program a dose or other configuration parameter that is outside the recommended range of the established clinical practice of the hospital. There are various types of infusion pumps used by medical personnel to infuse medicinal fluids into a patient's body. As mentioned above, some pumps use a customized drug library for electronically downloadable drug pumps. For example United States Patent Application No. 2007/0213598, which is incorporated by reference herein in its entirety, describes a system for maintaining drug information and communicating with medication delivery devices. In addition to updating a customized drug library, it is often desirable to update software running on a medical device, such as an infusion pump. However, prior art systems have several drawbacks. Following is a description of a novel medical device update system that solves various problems found in the prior art.

SUMMARY OF THE INVENTION

A method is described for providing updates to a medication administering device, the method including sending a message to the medication administering device, the message containing information relating to one or more update files available to the medication administering device, receiving the message at the medication administering device, downloading and storing one or more update files identified by the message, and installing the one or more update files on the medication administering device.

Another example provides a medical device system including a server, a communication network, and a plurality of medical devices in communication with the server over the communication network, the plurality of medical devices each having a storage location, and a control unit for controlling the operation of the medical device, wherein the control units are configured to pull update files in response to an update message received from the server, and wherein the control units are configured to manage the installation of downloaded update files.

Other features and advantages of the present disclosure will be apparent from the accompanying drawings and from the detailed description that follows below.

BRIEF DESCRIPTION OF THE DRAWINGS

The present disclosure is illustrated by way of example and not limitation in the figures of the accompanying drawings, in which like references indicate similar elements and in which.

DETAILED DESCRIPTION OF THE PREFERRED EMBODIMENT

Figure 1:
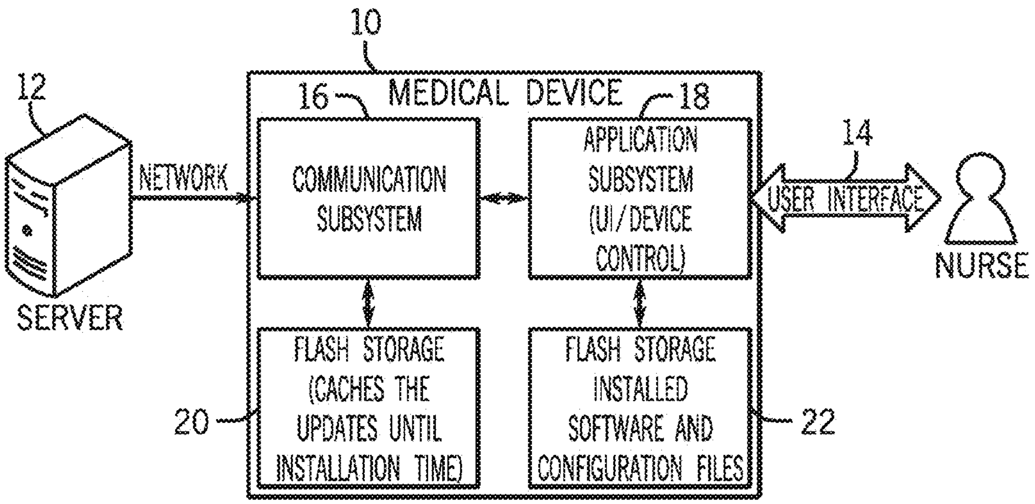
FIG. 1 is a block diagram illustrating a medical device in a hospital environment.

In general, the present disclosure describes a system and method for providing updates to medical devices or medical devices systems, such as medication administrating devices like medical infusion devices or infusion pumps. It is sometimes desirable to update the software running on a medical device to improve the performance, address problems, add features, or otherwise modify the operation of the medical device. For medical devices using a customized drug library, it is also sometimes desirable to update the drug library. In one example, software and configuration updates are "pulled" by the medical devices, rather than being "pushed" by a server (described in detail below).

While the system and methods described below may be applied to any desired medical device, the system and methods will be described in the exemplary context of infusion pumps. For example, the techniques disclosed may be used with infusion pumps such as a PLUM A+™ infuser or pump, available from Hospira, Inc. of Lake Forest, IL. Other types of pumps may also be used with the present disclosure. For example, the techniques may be used with patient-controlled analgesia (PCA) pumps, ambulatory pumps, enteral pumps, as well as IV infusion pumps. Application of the present invention to other medical devices such as ventilators, imaging systems, patient physiological condition monitors, glucose meters, diagnostic equipment and the like is also contemplated.

When configuring systems to update medical devices, numerous factors should be considered. For example, sometimes updates to the software and to the configuration of medical devices deployed into clinical settings are difficult to achieve in a timely and coordinated manner. The costs in time and labor are significant, also there may be opportunities for confusion in that two otherwise identical medical devices may operate or behave in different ways if a staggered update process is implemented and different configurations and software are in operation side-by-side.

There are typically two types of update processes which are preformed on deployed medical devices. These two types of update processes include updates to the operational software of the medical device, and updates to the device configuration. In the example of an infusion pump, an update to the device configuration may include updates to a customized drug library, which may include but is not limited to defaults, ranges (hard and/or soft limits) of acceptable pump configuration parameters like dose, rate, and volume; device-specific settings; acceptable ranges of monitored values, etc.

The task of updating software for medical devices deployed in clinical settings has traditionally required that the medical devices be physically removed from the clinical floor and transported to a specially prepared location such as a biomed center (a location where pumps are cleaned and serviced). Once removed from the floor, the devices may require special configuration, or partial disassembly by manufacturers' technicians in preparation for the update process. The software updates are then applied by technicians using a special update station in the biomed center. Updated devices, which required disassembly, are then reassembled by the manufactures' technicians. If necessary, the device can be specially configured to allow for verification that the update is successful. Once an update has been verified, the device is reconfigured for the clinical floor, typically by the hospital biomed technician. The device is also cleaned, completing the update process. The device is now ready to be returned to the clinical floor.

The update process described above typically takes more than an hour per device and does not scale well due to the number of manual steps and limiting mechanical steps, such as the time spent in the special programming station. Updating a hospital with thousands of devices, for example, using such a process, will take a considerable amount of time and effort. For example, a hospital with 2000 devices takes approximately one man year of effort to update.

Updating the configuration of a medical device is typically performed more often than the updating the software for the medical device. In one example, the device configuration is customized by the hospital directly and is updated quarterly (or more often) by the hospital, without any interaction with or assistance from manufacturers' technicians. Of course, configuration updates can be performed more or less frequently, as desired. In addition, configuration updates can be performed by hospital personnel, manufacturers' technicians, or other users.

In many cases, the configuration of a medical device may be updated electronically, if the medical devices are networked. In one example, the mechanism used to electronically deploy these updates is to 'push' the update data in small packets from a central server to the medical devices which are being updated. One drawback to this approach is that this process is so resource intensive at the server, that it is typically only effective when preformed to small groups of medical devices at a time, perhaps fifteen devices, in one example. In some examples, the medical devices are removed from the clinical floor and placed into a special state by the biomed technician to allow the update to be transferred to the device. As with the software updates, these manual steps limit the number of devices which may be updated in a given period of time.

In the example of pushing configuration updates, a hospital IT technician will begin the update process by manually selecting the medical devices which are to be updated. The technician then waits for the transfer of configuration updates to the devices to complete before additional devices are selected. In one example, the transfer time to the devices may take approximately thirty minutes, although the transfer time can also take over an hour for large configuration files. Also, in some examples, this type of transfer requires that if the transfer fails for any reason, it must then start again from the beginning—regardless of how much of the configuration was correctly received by the device. This leads to lengthy deployment times and inefficient utilization of the IT technicians' time as they must monitor the process and wait for completion before scheduling additional medical devices to update. If the medical devices require a biomed technician interaction or assistance, such as getting the device into a specific mode to accept the configuration update, then the biomed technician's actions will need to be synchronized with the IT technicians, which is another drain on hospital resources.

As mentioned above, the present disclosure also describes a system and method for providing updates to medical devices, such as infusion pumps, by pulling updates at the medical devices, rather than pushing updates from a server. This approach allows medical devices to remain on the clinical floor during software and configuration updates. Updates performed in this manner are installed by the medical device itself, without requiring the disassembly, manual programming or other special handling by either manufactures' technicians or hospital biomed technicians. In this example, updates are transferred to the medical devices using the hospital networking infrastructure. Also, in some examples, the installation of updates on a medical device is triggered by a user, such as a nurse, or other hospital personnel.

FIG. 1 is a block diagram illustrating a medical device in a hospital environment. As shown in FIG. 1, a medical device 10 (for example, an infusion device) and a remote server 12 are coupled by a computer network, allowing the server and medical devices to communicate with one another. The server 12 could be located in the hospital, at a location away from the hospital, at a manufacturer's facility, in another hospital, or anywhere else, as desired. The medical device 10 includes a user interface 14, allowing a user (e.g., a doctor, nurse, technician, patient, etc.) to monitor and/or operate the medical device 10. The user interface may include displays, key pads, touch screens, buttons and knobs, audio indicators, etc. Also note that, as is described in detail below, updates from the server 12 may also be transferred to a medical device using a physical storage medium (e.g., a removable USB flash drive, etc.), rather than using the network. Also, a variety of communication networking methods could be used to accomplish the transfer depending on the networking infrastructure available; for example Ethernet, Wi-Fi and Cellular networks could all be used for this purpose.

FIG. 1 also shows several subsystems of the medical device 10. A communication subsystem 16 facilitates communications between the medical device 10 and the server 12, as well as between the medical device 10 and other devices. An application subsystem 18 controls the operation of the medical device 10, as well as user interface 14. The medical device 10 also has a plurality of storage locations (described below). In the example of FIG. 1, a first flash storage location 20 caches updates until the updates are installed. A second flash storage location 22 stores installed software and configuration files. The operation of the first and second flash storage locations 20 and 22 is described in detail below, but generally, when updates are downloaded, they are cached and installed at a later time. At the same time, the current software and configuration files are cached, and are available to the system in the event that an update fails. This way, the medical device can return to the operating state that it was in prior to an attempted update. Also note that the storage locations, as described above, are merely examples. More or less storage locations could be used. Also, any desired type of storage medium could be used, besides flash memory. For example, the storage locations could use hard drives, solid state drives, or any other type of non-volatile memory.

Figure 2:
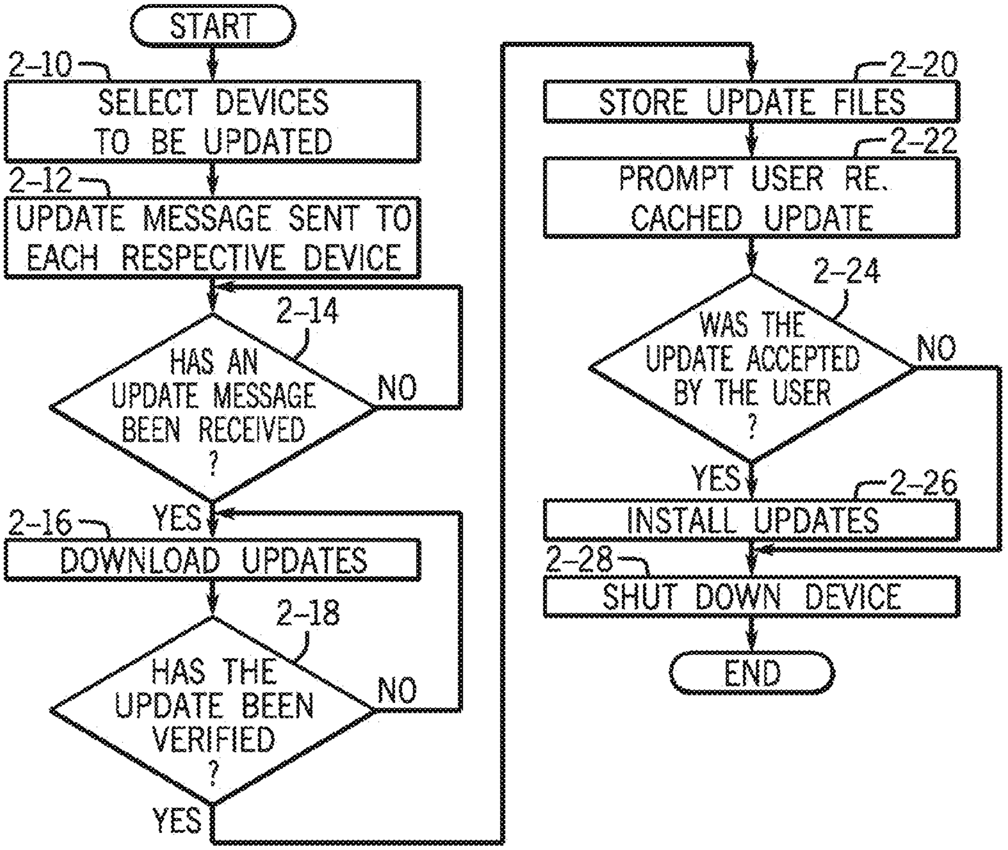
FIG. 2 is a flowchart illustrating one example of the process of updating a medical device.

FIG. 2 is a flowchart illustrating one example of the operation of a process of updating a medical device. The updating process is generally the same whether the software or configuration of the medical device is being updated.

The process illustrated in FIG. 2 begins at step 2-10 with a hospital IT technician (or other user) selecting the medical devices which are to be updated. Examples of the selection process are described in more detail below. After the medical device(s) are selected, the server will transmit an update message (in one example, a single message) over the network to each of the selected medical devices in the selected set of medical devices (step 2-12). In one example, each medical device receives a unique message. In other examples, the same message can be sent to the devices, with each device being able to parse the information relevant to that particular device. Devices that are not actively connected to the network will receive the update message when the server reestablishes communication with the device. In one example, the update message contains information about the update that the medical device will need to download and install the update. For example, the update message may identify the files that make up the update as well as the files' location on the network. One reason for this is to eliminate scaling issues which might otherwise force the server to manage the segmentation and transfer of updates to the devices at the application level.

At step 2-14, the process determines whether an update message has been received by the communication subsystem. If an update message has not been received, the process will keep waiting for a message. If an update message has been received, the process continues. At this point, the medical devices are now responsible for downloading the files of the update using networking operating system level interfaces, rather than an application level interface directly to each device. This distributes the workload to the devices (rather than being a burden on the server); with the further advantage of allowing the update file transfer to resume from a point when the network connection is lost to when it is reestablished. The continuing download can be accomplished without starting the process over.

At step 2-16, the update identified in the received update message is downloaded or pulled by the medical device. At step 2-18, the process determines whether the downloaded update has been verified. In one example, a downloaded update can be verified by using a checksum, or by using any other desired verification method. If the downloaded update files cannot be verified, the process proceeds back to step 2-16, where the updates are downloaded again. As mentioned before, the download process can continue where it left off, and the entire download process does not need to be restarted. Once the update is verified as being transferred correctly, the update files are stored in the storage location (step 2-20) by the communication subsystem, until needed by the installation process. In one example, at this point, the medical device waits for a signal from a user (e.g., a nurse, caregiver, or patient, etc.) to begin the installation process.

After the updates files are downloaded, verified, and stored, the communication subsystem signals to the application subsystem that an update is available. At this point, the system waits until such time that the updates can be installed. In one example, updates can be performed during a device power off process. In this example, when a user (e.g., a nurse, caregiver or patient) powers off the medical device, the user interface will prompt the user (step 2-22) with the information that an update (software, configuration, or both) is cached in the communication subsystem, and may now be installed. The process then proceeds to step 2-24, where the process determines whether the user accepts the update or rejects the update. If the user accepts the update, the installation process (step 2-26) will begin automatically. Once the update is complete, the device will shutdown normally (step 2-28). If, at step 2-24, the user rejects the update, the medical device will shutdown normally, without installing the update. The user interface will continue to notify the user of the available update until it is accepted. Throughout the update process described above, the status of the update process (e.g., update message received, update downloaded, update installed, update failed, etc.) is sent to the server by the communication subsystem. This way, the server will be able to track the status if each medical device in the system. If the medical device is unable to communicate with the server, the device will inform the server of its status when communication is established at a future later time. Similar status messages can be displayed on the user interface of the medical device.

Also note that, in one example, steps 2-10 through 2-20 can be performed in the background while the medical device is operating in its normal manner. As a result, the device does not need to be pulled from the clinical floor or placed into a special update mode in order to download and cache update files. In the example of an infusion pump, updates can be downloaded and stored at the same time that the infusion pump is being used to administer medications to a patient, without affecting the normal operation of the infusion pump. Also note that the process illustrated in FIG. 2 is described in the context of a single medical device. However, the update system can use the same process to administer updates to many of devices at the same time.

Following is a more detailed description of an exemplary update processes. Of course, updates may be performed in numerous ways, within the scope of this disclosure.

As mentioned above, an early step in the update process is to select one or more medical devices to be updated. Devices can be selected individually, or in groups, sets or subsets based on device type, device model, device location, etc. In one exemplary implementation of this feature, a wizard-based selection mechanism (described below) is provided to allow any number of the devices to be selected for updates. The wizard can run on the server, or on a network client that communicates with the server. Once an update process is triggered, the status of the update as it progresses will be displayed using the user interface of the server or network client, and will be available for viewing, and for use in standard reports.

One benefit of the update process illustrated in FIG. 2 relates to scalability. As mentioned above, as device update systems are scaled up, the load on a server can be overwhelming, preventing devices from being updated in a timely, cost-effective manner. By utilizing the 'pull' updating process illustrated in FIG. 2, an update process can be easily scaled up, without overwhelming the server. To help understand the differences between the 'push' technique mentioned above and the 'pull' technique illustrated in FIG. 2, a brief explanation of each technique is provided below.

Figure 3:
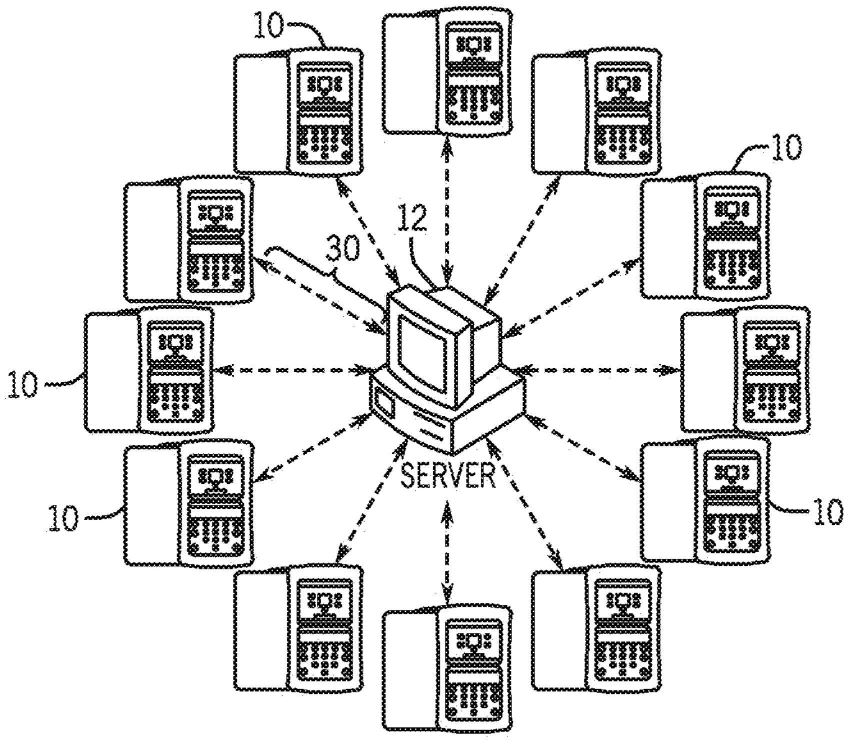
FIG. 3 is a block diagram of an update system using a 'push' update technique.

FIG. 3 is a block diagram of an update system using a 'push' update technique. FIG. 3 shows a server 12 and a plurality of medical devices 10, which are capable of communicating with the server 12 over a network. When a device 10 is selected for an update, the server 12 will segment the software or configuration file(s) into a plurality of chunks 30, and will calculate a checksum over the first chunk 30, which will be used later by the respective device 12 to verify that the transfer of the chunks 30 was completed without corruption or error. The server 12 opens and maintains a connection to the device 12 across the network. During an update process, each of the chunks 30 will be individually sent to the respective device 10. The server 12 monitors the delivery status of each chunk.

The device 10 receives and verifies each chunk 30 and sends a delivery success or delivery failure message to the server 12. The server 12 will then prepare, checksum, and send the next chunk 30. This process will repeat until the entire update file(s) has been transferred correctly or has failed. The failure recovery for this technique is to start over with the download beginning with the first chunk.

Using the example shown in FIG. 3, the load on the server 12 to segment and track the files as they are pushed to the medical devices is quite high, and may quickly saturate the server 12. As a result, perhaps only a few devices can be updated simultaneously, in order to maintain adequate resources to service devices that are not being updated. For example, the server receives status and log information from the devices and communicates therapy programming information to the devices, and is hampered in those activities.

Figure 4:
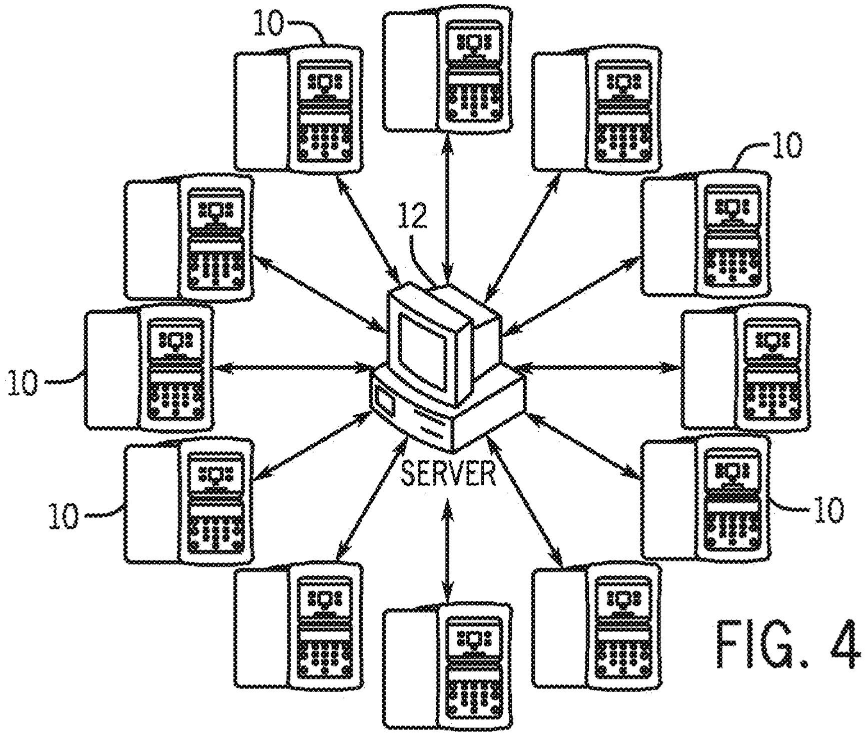
FIG. 4 is a block diagram of an update system using a 'pull' update technique

FIG. 4 is a block diagram of an update system using a 'pull' update technique, such as that described with respect to FIG. 2. FIG. 4 shows a server 12 and a plurality of medical devices 10, which are capable of communicating with the server 12 over a network. Using this method, in comparison to the method illustrated in FIG. 3, the server 12 sends to each medical device 10 to be updated an update message, which contains the location of files which makeup the update, called a manifest. From this point on, the medical devices themselves are responsible for downloading the update files. This results in a dramatic reduction in the amount of work the server 12 is responsible for at the application layer. A direct result of this is linear scalability of the update system, to the limit of system resources, chiefly network bandwidth.

Should the transfer of an update file fail, the device 10 automatically resumes the transfer from the point of the failure, rather than starting the download over. In this example, the device 10 will inform the server 12 of the status of the transfer. This messaging exchange provides only a light load on the server 12, freeing the server 12 to service the above-mentioned needs of the devices which are not being updated.

An additional improvement with this technique is that the manifest contains a checksum and version information. Therefore, the files which are already present on the device 10 are not transferred again. This will improve network utilization and system performance. Note that the same technique is used for software updates as well as for configuration updates.

Figure 5:
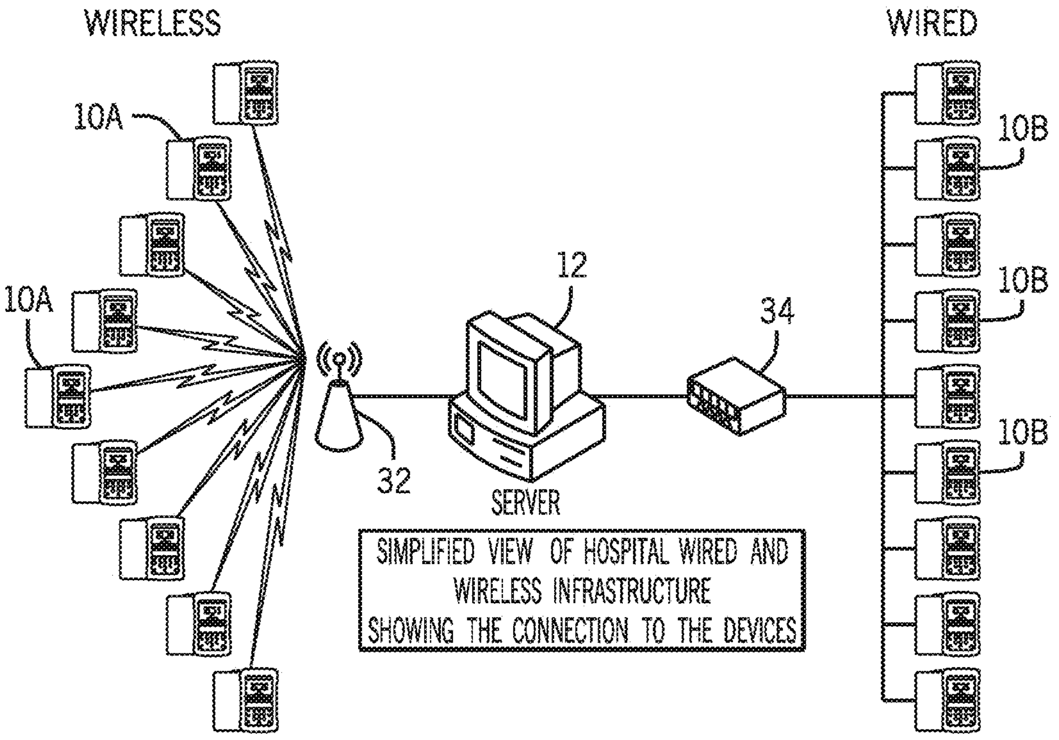
FIG. 5 is a block diagram showing a high level view of a hospital network.

The update mechanism described above supports wired and wireless infrastructures in a medical facility. FIG. 5 is a block diagram showing a high level view of a hospital network, including both wired and wireless connections to medical devices which may receive updates. FIG. 5 shows a server 12 coupled to a wireless router 32 for communicating with a plurality of medical devices IOA that have a wireless interface with the network. The server 12 is also coupled to a wired network router 34 for communicating with a plurality of medical devices 10B that have a wired interface with the network. Note that the network configuration shown is merely an example, and that other network configurations may also be used. Also, as described below, a medical device may also receive update files using a physical storage medium, such as a removable disk or USB flash drive.

Figure 6:
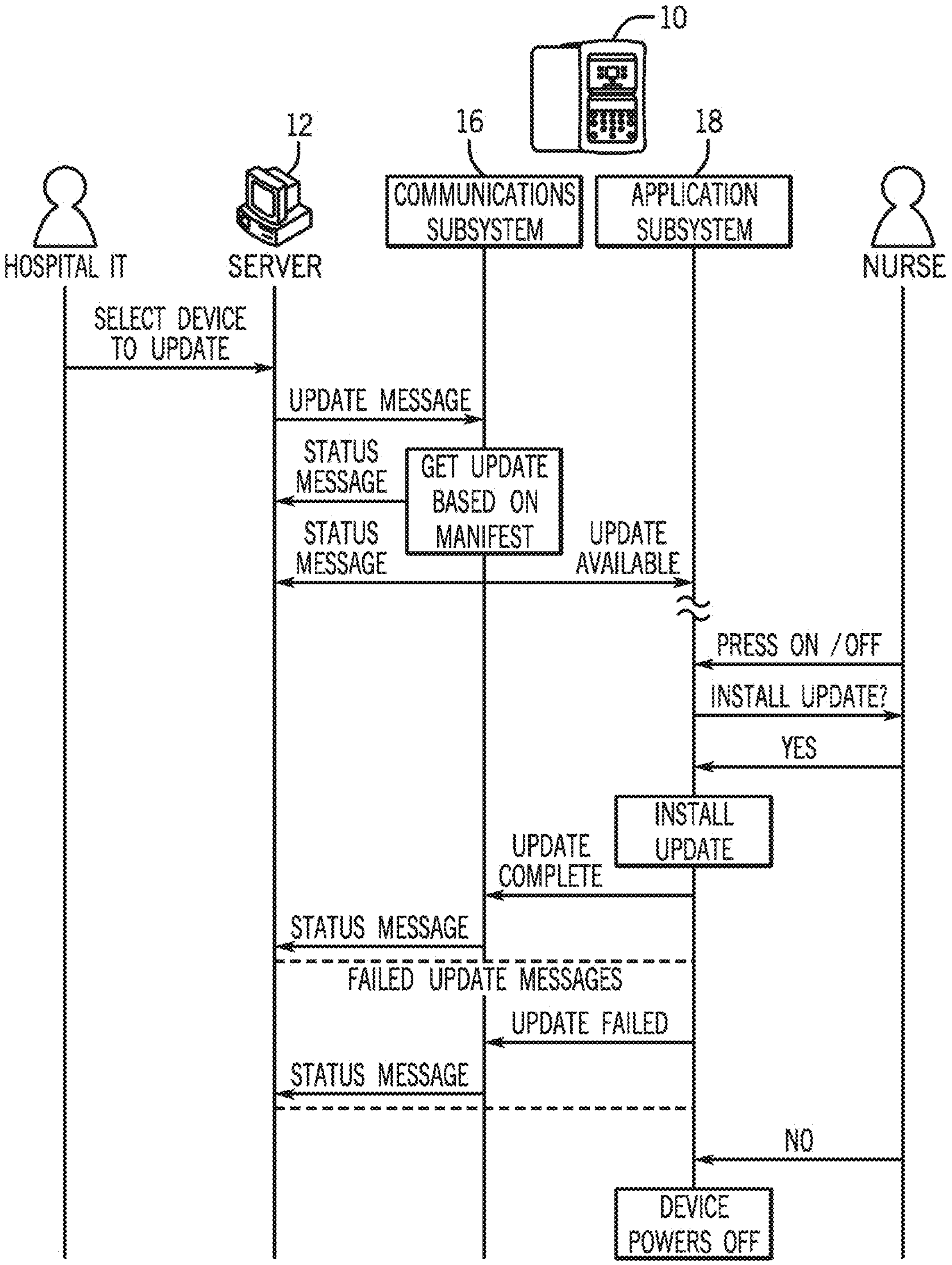
FIG. 6 is a sequence diagram illustrating an example of an update process.

FIG. 6 is a sequence diagram illustrating an example of the high level message handling and actions for the update process described above. FIG. 6 shows the server 12 and medical device 10 (including the communication subsystem 16 and application subsystem 18) described above with respect to FIG. 1. FIG. 6 also illustrates the actions of a first user (shown as hospital IT personnel) and a second user (shown as a nurse, caregiver or patient) in the process.

As shown, a first user selects one or more devices to be updated (software and/or configuration updates). In response, the server 12 generates and sends an update message for the medical device 10. The update message contains the network location of the update files. The communication subsystem 16 receives the update message and in response, downloads the update files (checking any files it already has against the manifest in the update). Once the files are downloaded and verified to have been transferred correctly, the communication subsystem will write the files to local flash storage to cache them on the device 10, awaiting the time when the user initiates the update process. When all of the update files are cached, the communication subsystem 16 will send a message to the application subsystem 18, indicating that an update is available.

During a normal shutdown of the medical device the application subsystem 18 will ask the user (a nurse, in this example) whether the updates should be installed. If the user accepts, the updates will be installed, and the medical device 10 will shutdown. During the updating process, the medical device will provide status messages to the server 12, indicating the status of the update process (e.g., files successfully downloaded, download failed, update complete, update failed, etc.).

As mentioned above with respect to FIG. 1, the medical device 10 also has first and second flash storage locations 20 and 22 for caching updates and installed and configuration files. In one example, the storage locations can be utilized as follows.

After an update has been downloaded and the files have been cached, the communication subsystem 16 advertises the availability of the update to the application subsystem 18. As such, there is a window during which the update has not been transferred to the application subsystem 18. During the window, if a new update (i.e., a second new update) is transferred to the communication subsystem 16, it should also be verified and stored. Until this process is complete, the previous update is considered the active update, and will be what is sent to the application subsystem 18, if an update is requested by the user.

However, once the new update (the second new update) is successfully transferred from the server and written to the alternate cache location, this new update (the second new update) becomes the active update, and will be what is sent to the application subsystem if an update is requested by the user.

Figure 7:
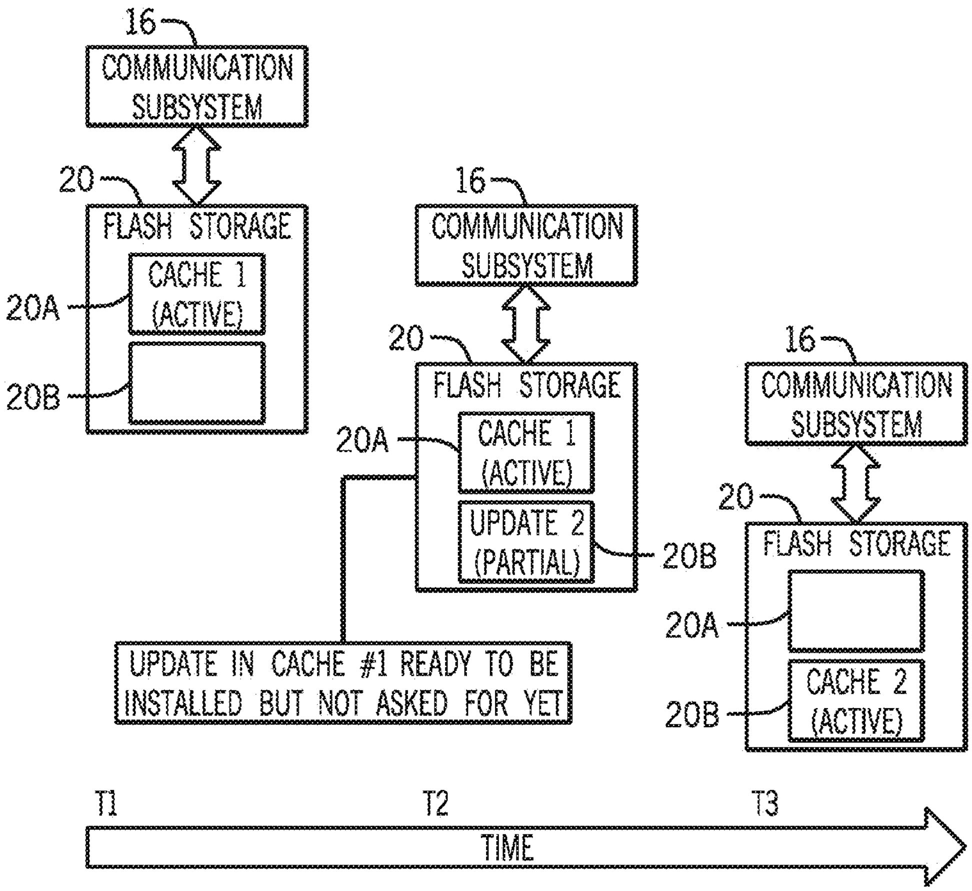
FIG. 7 is a timing diagram showing a process where two new updates are downloaded prior to installation.

FIG. 7 is a timing diagram showing this process (where 2 new updates are downloaded).

FIG. 7 shows the communication subsystem 16 and the storage location 20 at three different time periods—T1, T2, and T3. The storage location 20 includes two partitions (cache locations 20A and 20B). At time Tl, a first update has been downloaded and stored in storage location 20A. At time T1, this update is considered the active update, meaning that, if an update request were to come from the user at time T1, that is the update that would be installed.

At time T2, the first update is still cached, but there has still been no request from a user to install the update. At the same time, a newer update (a second new update) is currently downloading to storage location 20B. At time T2, the first update (the stored in cache 20A) is still considered the active update, meaning that, if an update request were to come from the user at time T2, that is the update that would be installed.

At time T3, the second new update has finished downloading, has been verified, and is stored in storage location 20B. Now, since this update is the newest, this update is considered the active update, and would replace the previous uninstalled update. If an update request were to come from the user after time T3, the second update (stored in storage location 20B) would be the update that would be installed. This situation may be a rare, but possible circumstance.

To ensure the continued proper operation of a medical device, precautions should be taken to maintain the proper operation software and/or configuration of the medical device. For example, some medical devices cannot operate without a correct configuration. In this case, special care can be taken to preserve the previous configuration (if it is still acceptable) when a configuration update installation fails. In one example, when updates are transferred from the communication subsystem, until they are successfully received and committed to flash, the previous configuration remains in effect.

Once the new updated configuration is committed to flash, the former configuration is deactivated and becomes the previous configuration and this location is where the next new configuration will be written. If the receipt of a new configuration fails, or if the write to flash of the new configuration fails, then the active partition remains unchanged. If the receipt and write are successful, then the new configuration becomes the active configuration.

Figure 8:
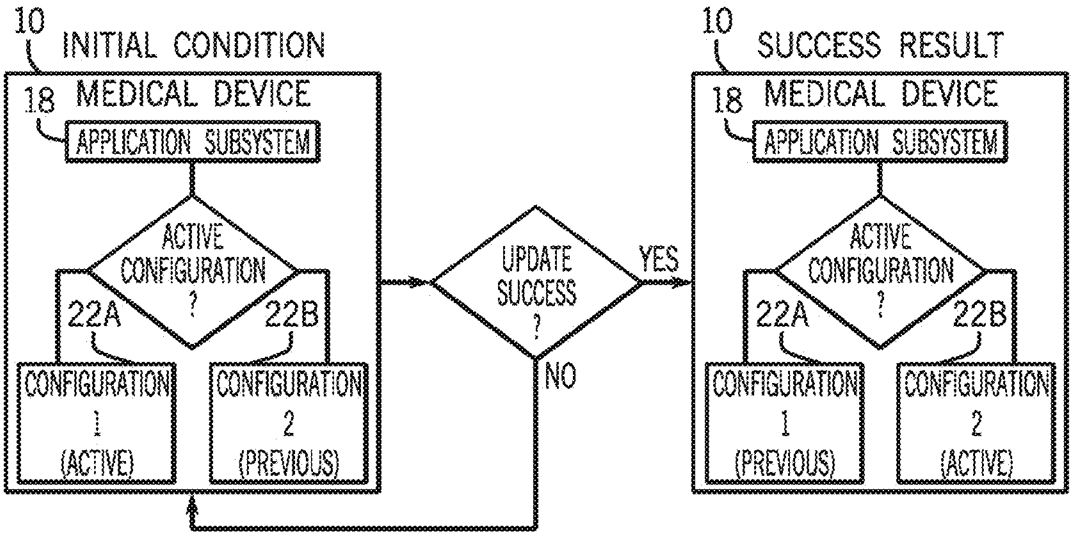
FIG. 8 is a diagram and flow chart illustrating the state of a medical device before and after an attempted update.

FIG. 8 is a diagram and flow chart illustrating the state of a medical device before and after an update. The left portion of FIG. 8 shows the medical device in an initial condition. In the initial condition (the left side), two configurations are cached, the active configuration (stored in storage location 22A), and the previous configuration (stored in storage location 22B). If the installation of new configuration is successful (the right side of FIG. 8), the new configuration becomes the active configuration, and the former configuration is deactivated and becomes the previous configuration (this is where the next new configuration will be written). If the installation of new configuration fails, then the active partition remains unchanged.

In one example, the processing of updates follows a script which is contained in the update message. The communication subsystem uses the script to orchestrate the processes and sequences which will be followed. For example, the script may dictate which portions of the system are updated first and how they are updated. The system may also provide for some flexibility in the update process to counter unforeseen issues.

In one example, the scripting can be used to force the update to occur during the power off processing without offering the option to a user to not perform or defer the update. In other words, the assent of the user is not required. This may be useful in a situation where an update is very important, or if the update fixes a known problem with the medical device.

In another example, the scripting can be used to have an update be staged on the device until a specific time, so that all updates would be available after a specific time in the future, but not before. In another example, the scripting can be used to ensure an update is installed by a certain date and/or time, or on a specific date and/or time. Scripting may also be used for numerous other features, as desired.

Since the proper operation of a medical device is very important, some measures should be taken to ensure that updates are performed securely. The security of the update files is insured by encrypting the update file in such a way that the medical device will be able to decrypt the files after transfer. However, if update files are intercepted during transfer it would be impossible to view the data in the update. Any desired conventional encryption scheme could be used.

The encryption mechanism will also insure that if an update file is intercepted, it cannot be modified and then replayed to the medical device as a valid update. If attempted, the device will reject the update as an invalid file. Only correctly encrypted files will be accepted by the medical device as the most basic level of integrity check on the update that is transferred.

As mentioned above, in other examples of the basic mechanism for software and configuration updates is an extension to a physical device for transport of the updates, rather than utilizing the hospital network infrastructure. While any desired physical device may be used, an example will be described using a USB flash disk. In this example, the server creates and stores an update(s) on a USB flash disk which will contain the update files and an associated script. When the USB flash drive is inserted into a device to be updated, the communications subsystem will copy the update files from the USB interface just as if the update was transferred across the network infrastructure.

Figure 9:
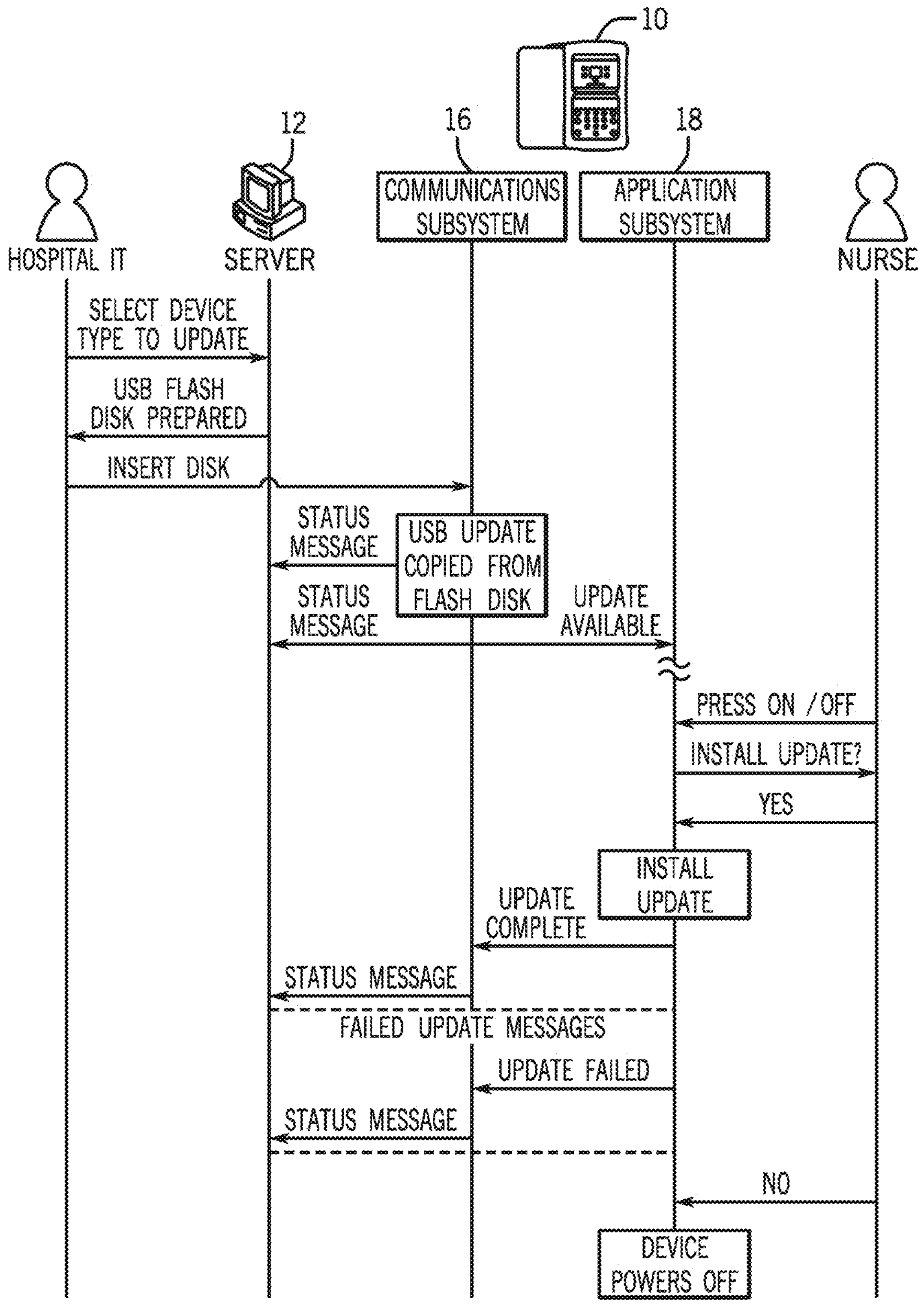
FIG. 9 is a sequence diagram illustrating an example of the high level message handling and actions for an update process using a removable USB flash drive.

If the medical device is networked, it will continue to operate as it would for a network delivered update and report the status of the update as it occurs. FIG. 9 is a sequence diagram illustrating an example the high level message handling and actions for an update process using a USB flash disk to transport updates. FIG. 9 shows the server 12 and medical device 10 (including the communication subsystem 16 and application subsystem 18) described above with respect to FIG. 1. FIG. 9 also illustrates the actions of a first user (shown as hospital IT personnel) and a second user (shown as a nurse) in the process.

As shown, a first user selects a device or device type to be updated (software and/or configuration updates). In response, the server generates a USB flash disk that contains the update(s) and the script. At the medical device 10, a user inserts the USB disk into a USB port on the device 10. At this point, the script takes over, and the update is copied by the communications subsystem 16. Once the files are copied from the flash disk and verified, the update files will be stored in cache, awaiting the time when the second user initiates the update process. When the update files are cached, the communication subsystem 16 will send a message to the application subsystem 18, indicating that an update is available.

During a normal shutdown of the medical device 10, the application subsystem 18 will ask the user (a nurse, in this example) whether the updates should be installed. If the nurse accepts, the updates are installed, and then the medical device 10 will shutdown. During the updating process, the medical device will provide status messages to the server 12 (assuming that the device 10 is networked), indicating the status of the update process (e.g., files successfully downloaded, download failed, update complete, update failed, etc.). If the medical device 10 is not networked, the status messages will be sent to the server the next time the device is connected to the network.

The description above of a medical device update system has been described in general terms, with some more specific examples included. Following is a description illustrating an exemplary implementation in specific medical device system. The following description describes a system based upon Plum A+TM infusion pumps and Hospira MedNet™ software working together through a network system in a hospital environment. Plum A+™ infusion pumps and Hospira MedNet™ software are available from Hospira, Inc. of Lake Forest, IL and can be adapted or modified according to the present invention.

An infusion pump system is provided for delivering and installing a drug libraries and infusion pump software electronically. The installation of software is integrated with a drug library download and installation process. Described below are representations of the display screens and actions that occur during software and drug library installations, including for both success and failed installations. Sequence diagrams show at a high level the interaction and interface with the various systems.

Figure 10:
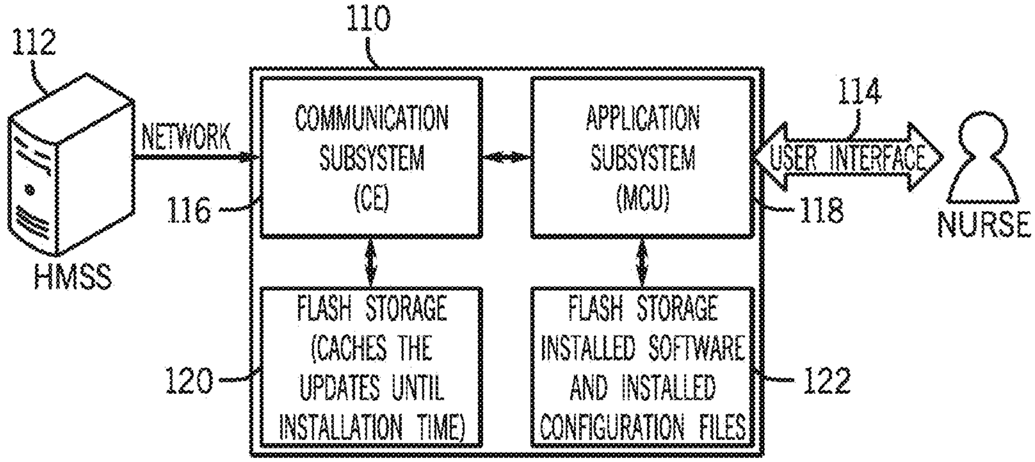
FIG. 10 is a block diagram of an infusion pump system.

FIG. 10 is an infusion pump system block diagram. FIG. 10 shows an infusion pump 110 (i.e., an infuser) and a Hospira MedNet™ server 112 or HMSS coupled by a computer network, allowing the server and infusion pump to communication with one another. The infusion pump 110 includes a user interface 114, allowing a nurse, or other user, to monitor and/or operate the infusion pump 110. The infusion pump 110 includes a communication subsystem 116 (i.e., a communication engine) and an application subsystem 118 (i.e., an MCU (master control unit)), as shown. The communication subsystem 116 has access to flash storage 120 for caching updates until installation time. The application subsystem 118 has access to flash storage 122 for storing installed software and configuration files.

Figure 11:
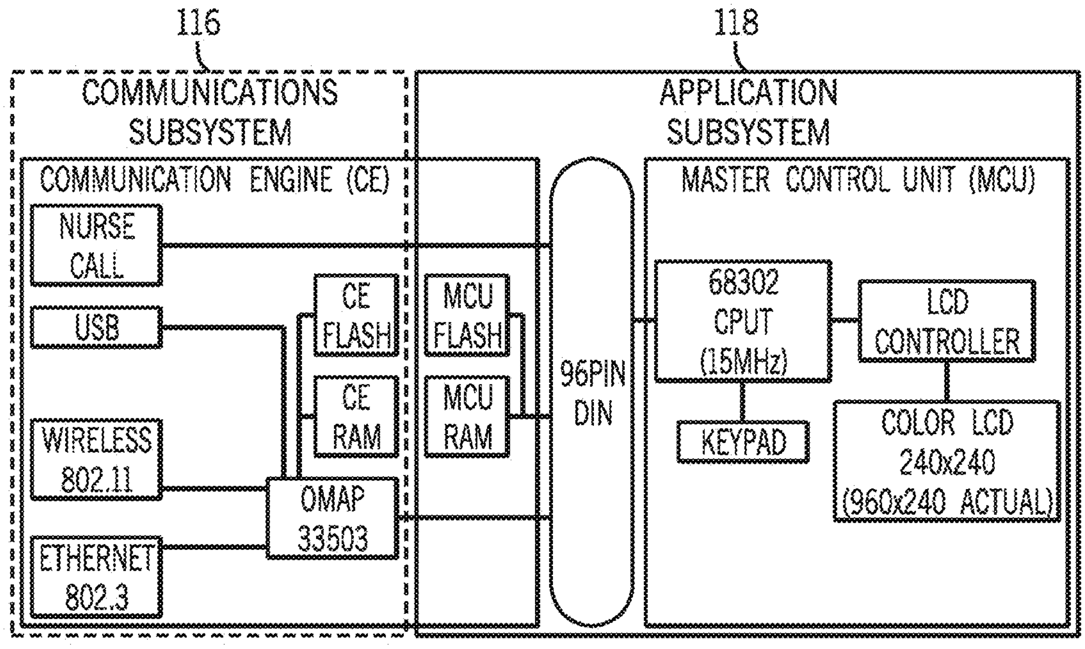
FIG. 11 is a block diagram of an infusion device physical/subsystem.

FIG. 11 is an infusion device physical/subsystem block diagram illustrating the physical arrangement of some features of the infusion pump communication subsystem 116 and application subsystem 118. Both subsystems have access to RAM and flash memory. The communication subsystem 116 includes interfaces to outside systems (wired and wireless). The MCU of the application subsystem 118 includes a CPU, and also provides control of the pumping action, as well as the user interface devices.

Figure 12:
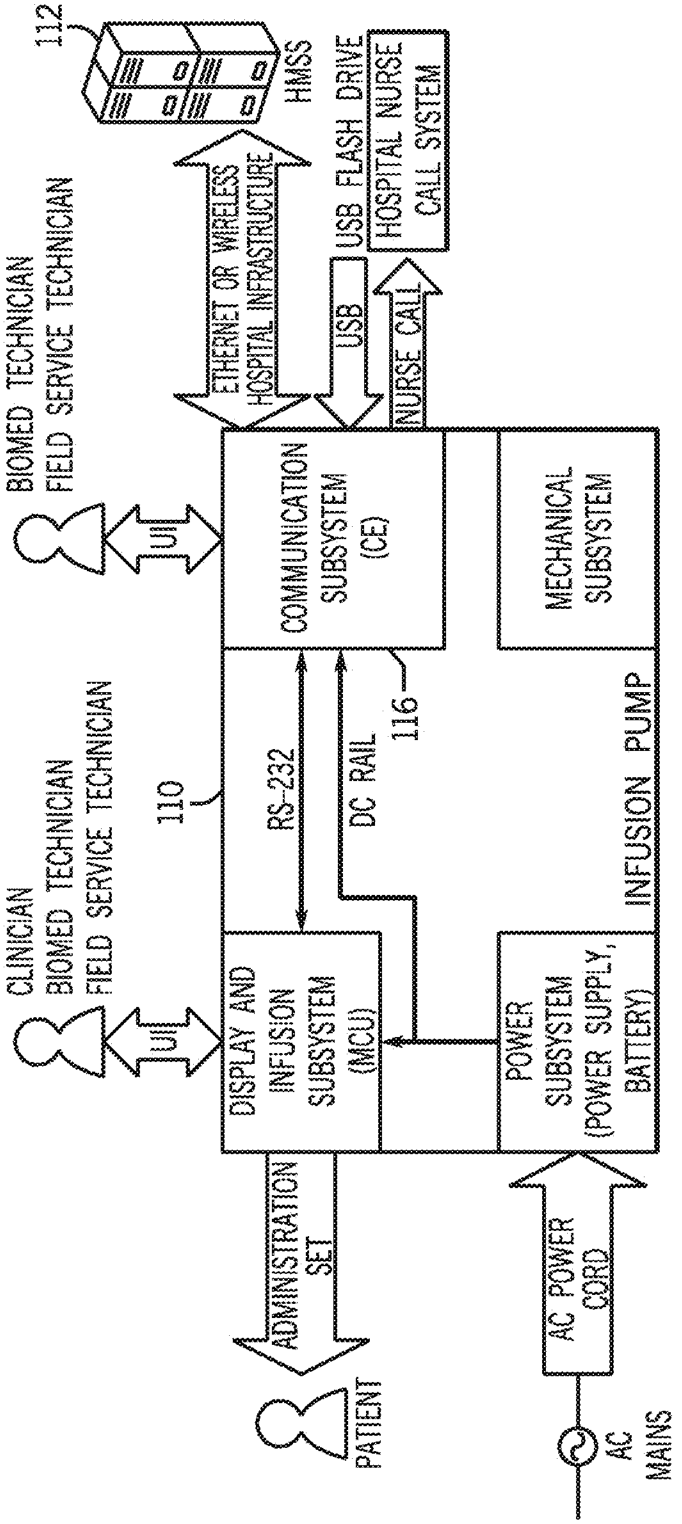
FIG. 12 is a block diagram of an infusion pump system architecture.

FIG. 12 is an infusion pump system architecture block diagram. FIG. 12 shows an infusion pump 110, including the communication subsystem 116, which provides a communication interface with the server 112 and a hospital nurse call system. The infusion pump 110 also includes a mechanical subsystem, a power subsystem, and a display and infusion subsystem (part of the MCU).

Like the examples described above, the infusion pump system illustrated in FIGS. 10-12 is capable of handling updates to the infusion pump software and to the drug library. When the communication subsystem 116 receives an update request from the server 112, the received message will contain a manifest of files which make up the update. In this example the update will be for a drug library or software and a drug library.

In most cases, a software update will come with a new custom library. In this case, when a new software update is provided, the update will comprise a matched set, including a software update and a drug library update, since the drug library is closely tied to the application and a change in the software affects the drug library. In some examples, the system is configured to not allow receiving just software without a custom drug library prepared with the drug library editor (DLE) application. This is controlled by the server.

The received manifest also includes the network location (path) to each of the files in the update. The communication subsystem is responsible for downloading the update files, verifying them, and storing them locally in communication subsystem flash. The communication subsystem will then notify the MCU that there is a custom drug library or software update and a drug library to transfer and install.

It is important to note that, in this example; the communication subsystem is running and possibly connected to the server when the infuser is plugged into AC power. Powering off the infuser while plugged into AC power will only power off MCU—the communication subsystem will continue to operate, enabling updates to be transferred to and installed on the medical device even when the medical device is powered off.

Once informed of a pending drug library update, the MCU will cause a screen on the infuser to display when the user attempts to power off the infuser. This screen gives the user a choice to install the drug library at that time, or to defer the installation to a later time. If the user chooses to install the drug library, the AC power status is first verified (to reduce the chances power loss during the installation) and the communication subsystem will transfer the data to MCU. When the transfer is complete, the installation process will continue without operator input.

If the user chooses not to install the drug library, the MCU will power down without installing the new drug library. The user will continue to be notified that there is a drug library update available each time the infuser is powered down until the drug library is ultimately installed.

In the case of an installation failure, the user will be alerted with a failure screen on the subsequent power on. The operator may then re-attempt the installation by powering off the infuser, or may continue to operate with the previous custom drug library.

Figure 13:
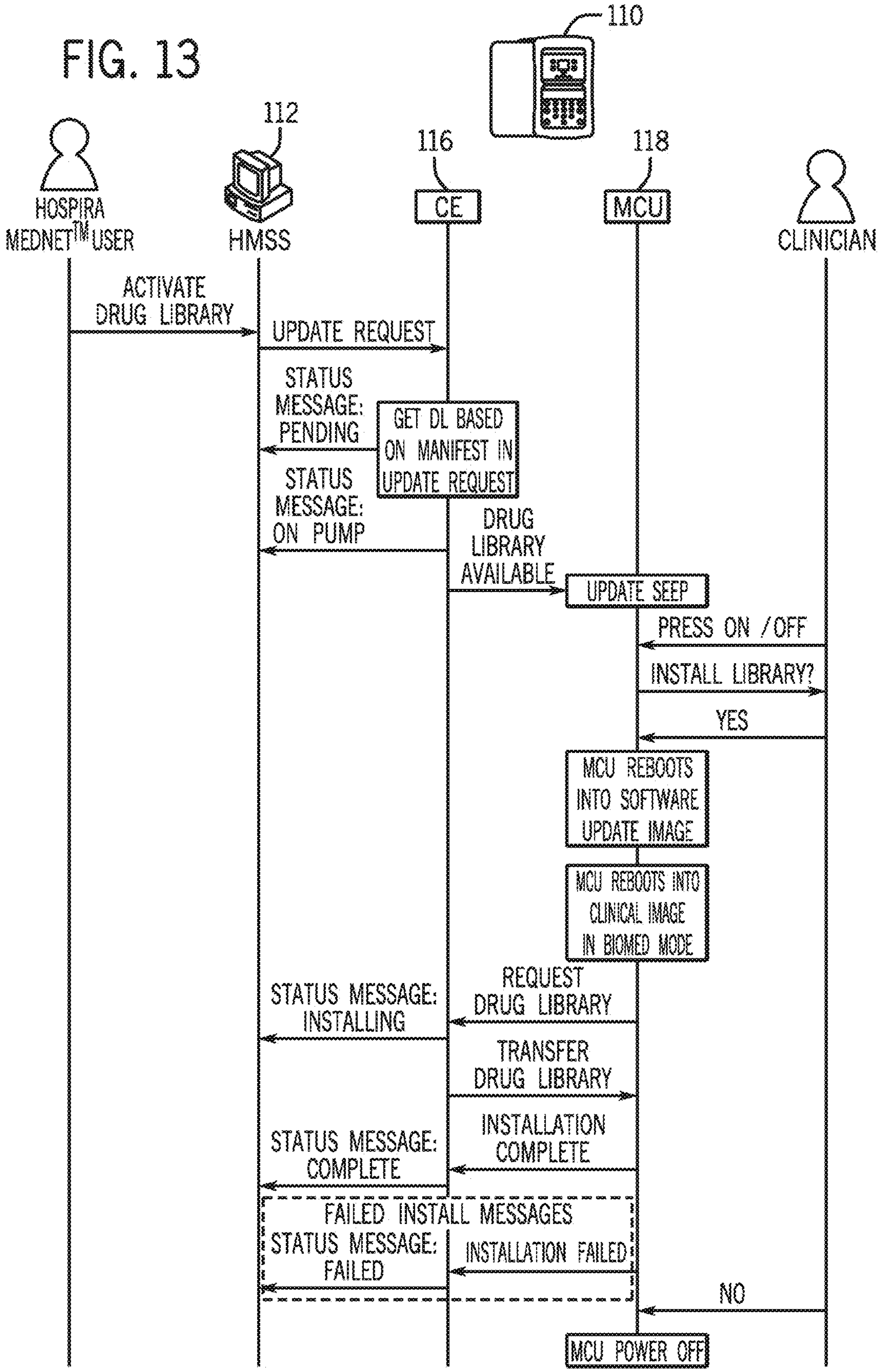
FIG. 13 is a sequence diagram showing the exchange for a library download, transfer, and installation.

FIG. 13 is a sequence diagram showing the exchange for a drug library download, transfer and installation. As shown, a Hospira MedNet™ user activates a drug library for one or more infusion pumps. In response, the server 112 generates and sends an update message for the medical device 10. The communication subsystem 116 receives the update message and in response, downloads the drug library update files (checking any files it already has against the manifest in the update). Once the files are downloaded and verified, the communication subsystem 116 will send a message to the application subsystem 118, indicating that an update is available.

During the shutdown of the infuser, the MCU will ask the user whether the updates should be installed. If the user accepts, the MCU reboots into a software update image. The MCU then reboots into a clinical image in a biomed mode. Next, after a request, the drug library is transferred from the communication subsystem to the MCU and installed. Finally, the infuser will shutdown. During this process, the infuser will provide status messages to the server 112, indicating the status of the update process (e.g., files successfully downloaded, download failed, update complete, update failed, etc.).

The process for updating MCU software is similar to the custom drug library installation insomuch as it occurs when the operator powers down the infuser. At that point, the communication subsystem will have received and verified the software and or drug library against the information sent from the server (the manifest file with checksums, and version information for the packages to install). The communication subsystem will advertise this new software and custom drug library to the MCU across its serial interface. The MCU will mark this in a special memory location called SEEP—Serial EEPROM in FIG. 14).

When the infuser is powered down (based on a user pressing the On/Off button) a screen will be displayed by the MCU offering to begin the software installation process.

Figure 14:
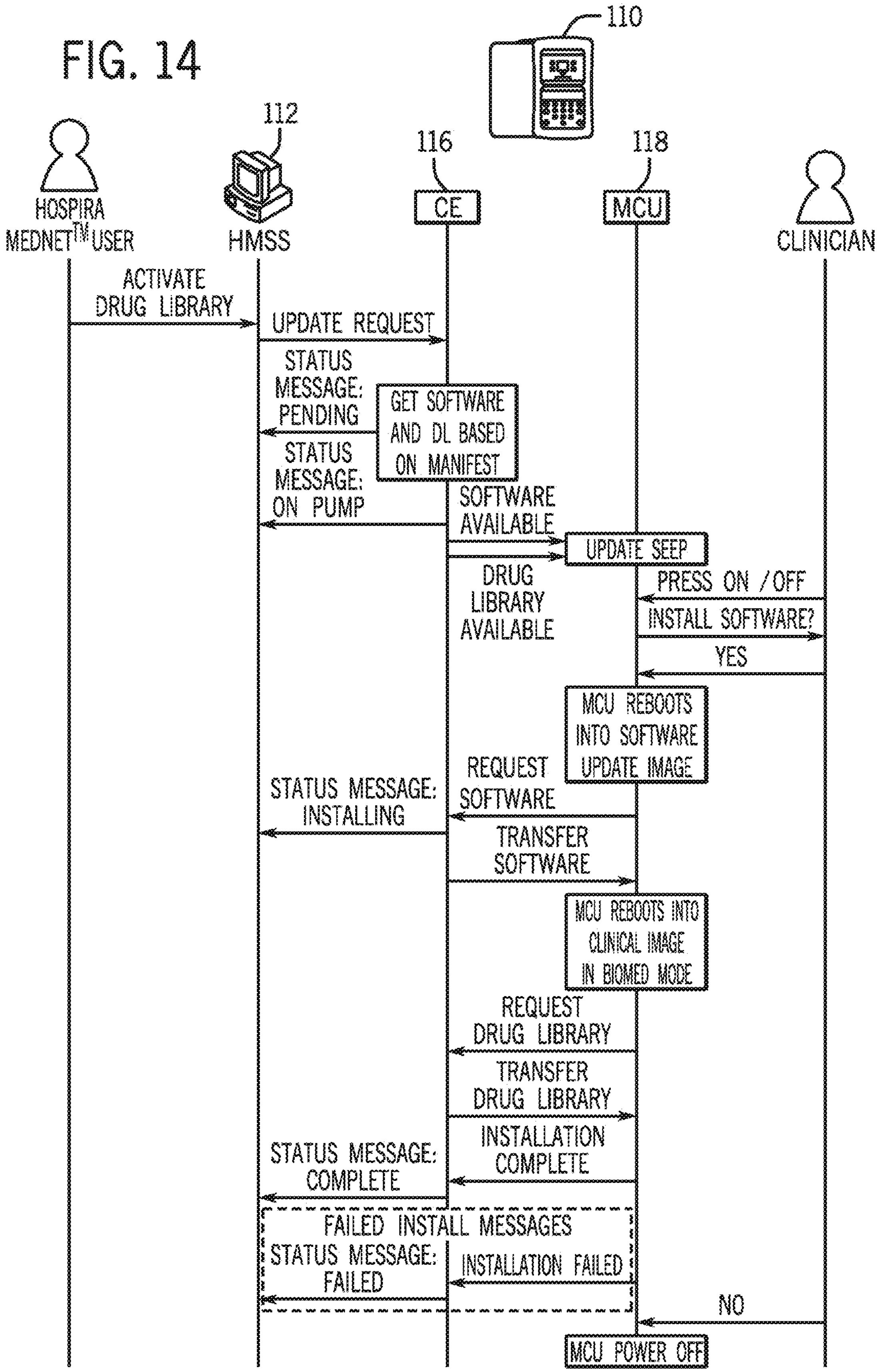
FIG. 14 is a sequence diagram showing the exchange for a software and library download, transfer, and installation.

FIG. 14 is a sequence diagram showing the exchange for a software and library download, transfer and installation. As shown, a Hospira MedNet™ software user activates a drug library for one or more infusion pumps. In response, the server 112 generates and sends an update message for the medical device 10. The communication subsystem 116 receives the update message and in response, downloads the software and drug library update files (checking any files it already has against the manifest in the update). Once the files are downloaded and verified, the communication subsystem 116 will send a message to the application subsystem 118, indicating that software and drug library updates are available.

During the shutdown of the infuser, the MCU will ask the user whether the updates should be installed. If the user accepts, the MCU reboots into a software update image. Next, after a request, the software is transferred from the communication subsystem to the MCU. The MCU then reboots into a clinical image in a biomed mode. Next, after a request, the drug library is transferred from the communication subsystem to the MCU and the updates are installed. Finally, the infuser will shutdown. During this process, the infuser will provide status messages to the server 112, indicating the status of the update process (e.g., files successfully downloaded, download failed, update complete, update failed, etc.).

Note that if there is a software update for the communication subsystem as part of the software update package from the server, the communication subsystem update will install first before the software will install on the MCU. In any case, the last thing installed from a software update package will be the custom drug library for the MCU.

As discussed above with respect to FIG. 8, to ensure the continued proper operation of an infuser, precautions should be taken to maintain its proper operation. For example, an infuser may not operate without a correct configuration. Therefore, special care can be taken to preserve the previous configuration when a configuration update installation fails. In one example, when updates are transferred from the communication subsystem, until they are successfully received and committed to flash, the previous configuration remains in effect.

Figure 15:
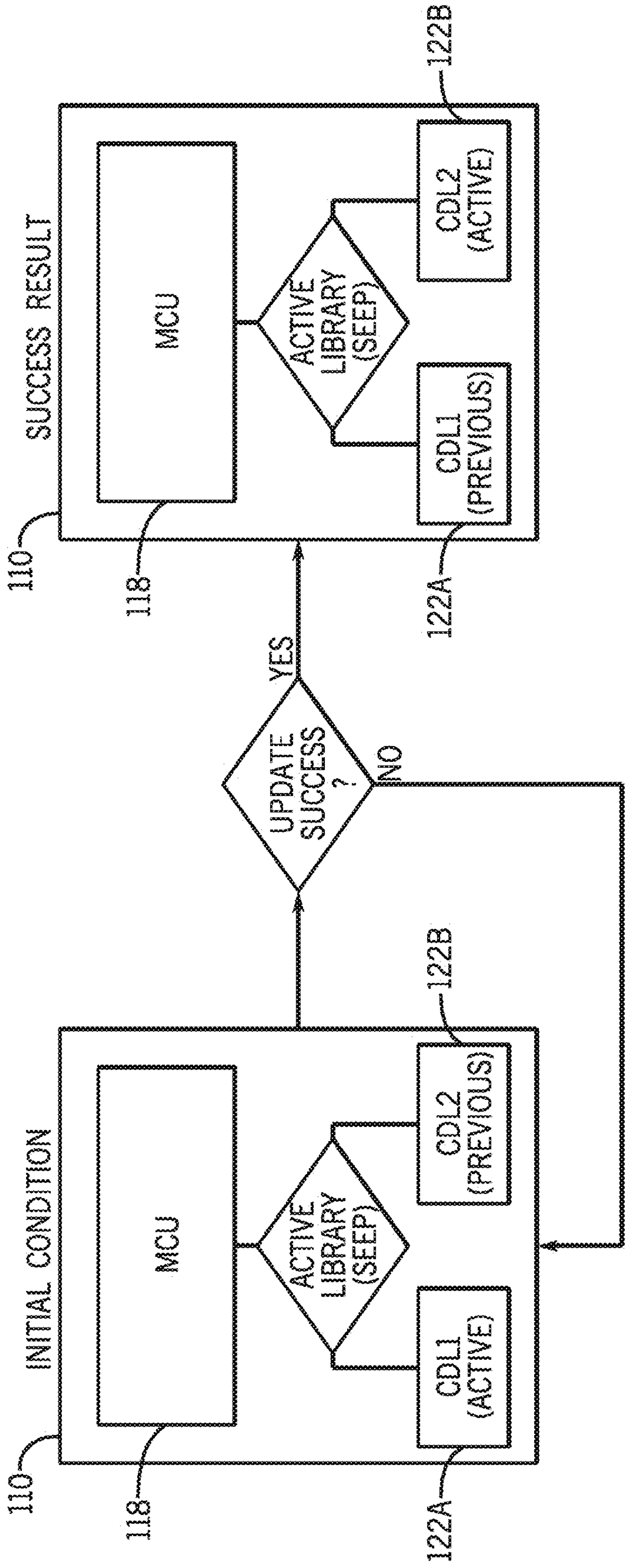
FIG. 15 is a diagram and flow chart illustrating the state of an infuser before and after an attempted update.

FIG. 15 is a diagram and flow chart illustrating the state of an infuser before and after an update is attempted. As shown, the MCU 118 maintains two drug library locations 122A and 122B in its flash memory. The SEEP controls which is the active library. As new libraries are loaded onto the MCU, the previous active library is maintained as a failover option. When new software is installed on the MCU, all previous custom drug libraries are erased as the format may have changed. As a part of the installation process for new software, the default drug library which comes with the new software is copied to one of the custom drug library (CDL) locations and SEEP is updated with this information as the active library. The communication subsystem will send the custom drug library, which is part of the update package, and the MCU will store the custom drug library in the unused custom drug library flash location and update SEEP with the newly stored custom drug library as the active CDL.

Subsequent updates will then cause the oldest library to be replaced with the new library and updates to SEEP will control which is the active library on the next power up.

If a custom drug library installation fails there will be no update in SEEP, so the previous active drug library will continue to be the active drug library. When the user next powers the MCU off, the drug library install screen will again offer to install this or any newly delivered custom drug library.

FIGS. 16-19 are diagrams illustrating processes for updating drug libraries and software, from the perspective of a user of the device. FIGS. 16-19 illustrate walkthroughs that provide the important points of a user's experience and show the sequence and state information as the process is preformed for the custom drug library installation and software installation, as well as the failure processing when an update operation fails.

Figure 16:
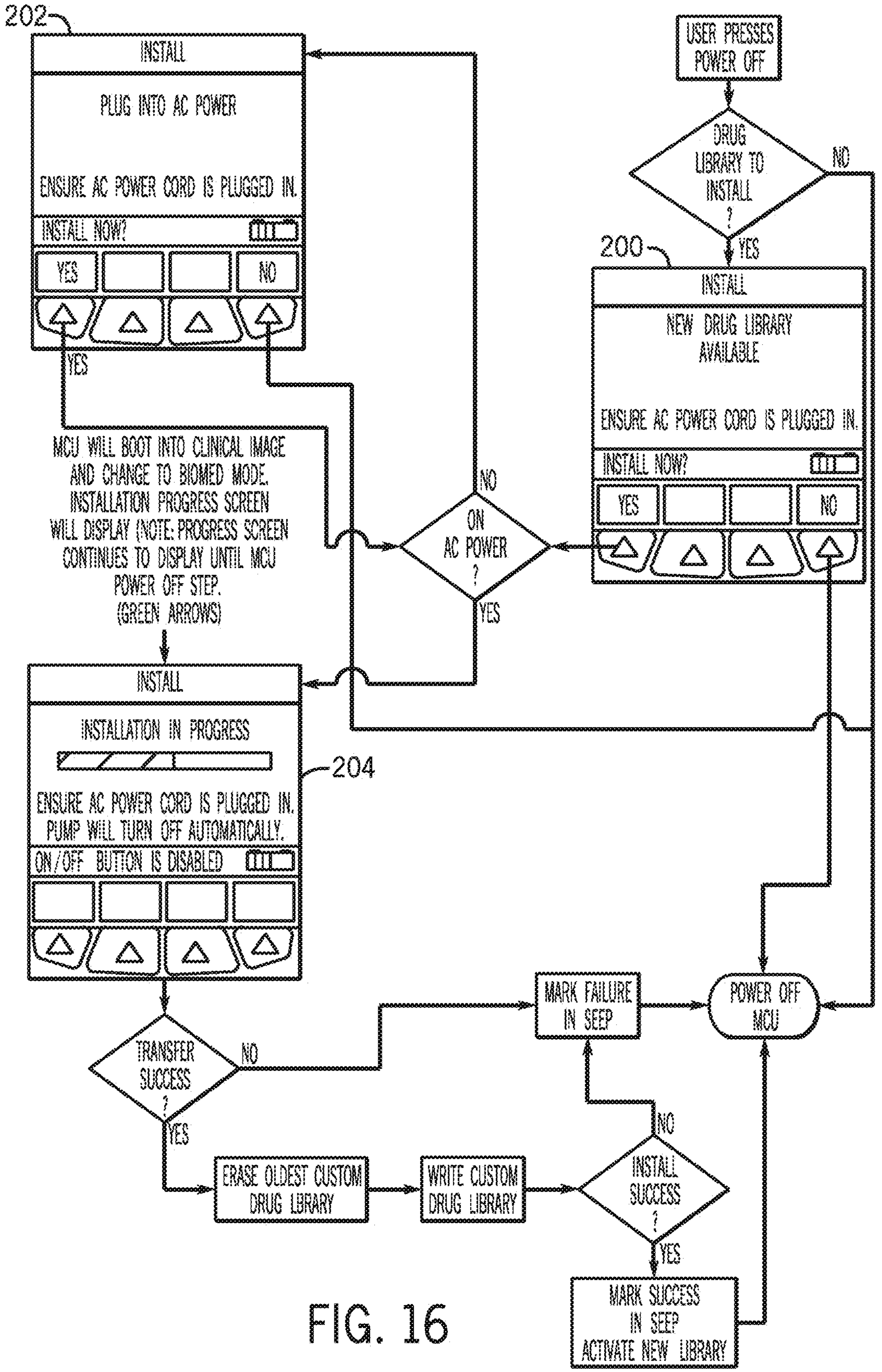
FIGS. 16-19 are diagrams illustrating processes for updating drug libraries and software, from the perspective of a user.

FIG. 16 illustrates an infuser screen walkthrough for a drug library installation, showing the steps and screens which will occur during the drug library transfer and installation process. The process begins when the user presses the power off button. If there is a drug library ready to be installed, screen 200 appears, and the user is asked to install the update. If the user selects "No", to MCU powers off. If the user selects "yes", the system verifies whether the infuser is plugged into AC power. If not, window 202 appears, telling to user to plug the unit it. Next, screen 204 appears, and the installation begins. If the transfer is successful, the oldest drug library is erased and the new library is written to memory. Next, the SEEP memory is marked as either a success or failure, and the MCU is powered off.

Figure 17:
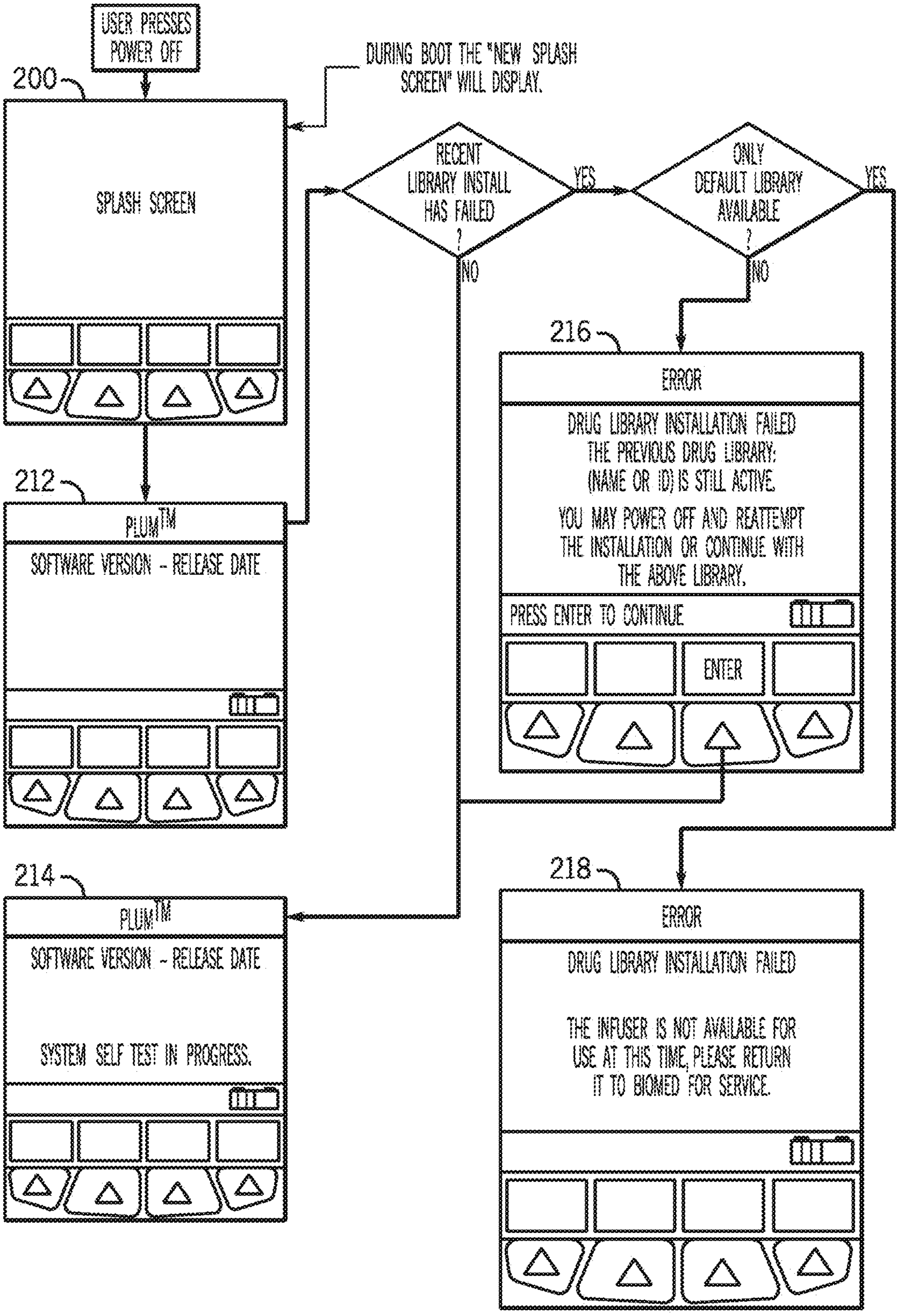

FIG. 17 illustrates an infuser screen walkthrough for a failed drug library installation. The screenshots of FIG. 17 show the steps and screens which result from a failed Library installation during subsequent power on processing. The drug libraries on the infuser are stored such that if a new drug library fails to install correctly the previous library is available and is used until the user can reattempt the installation. However if the only previous drug library available is the default drug library then the infuser is not available for use. This will be the case if new software is installed and the custom drug library that came as part of the software update fails to install correctly.

The process begins when the user presses the power on button, and the splash screen 210 appears. If the install was successful, or if the user pressed the 'Enter' button on a failed screen where the only remaining library is not the default library, then the normal flow of screens (screens 212,214) will be displayed. After a failed installation, either error screen 216 (where the user has the option of using the previously installed drug library) or screen 218 (where the infuser will be inoperable) will appear.

Figure 18:
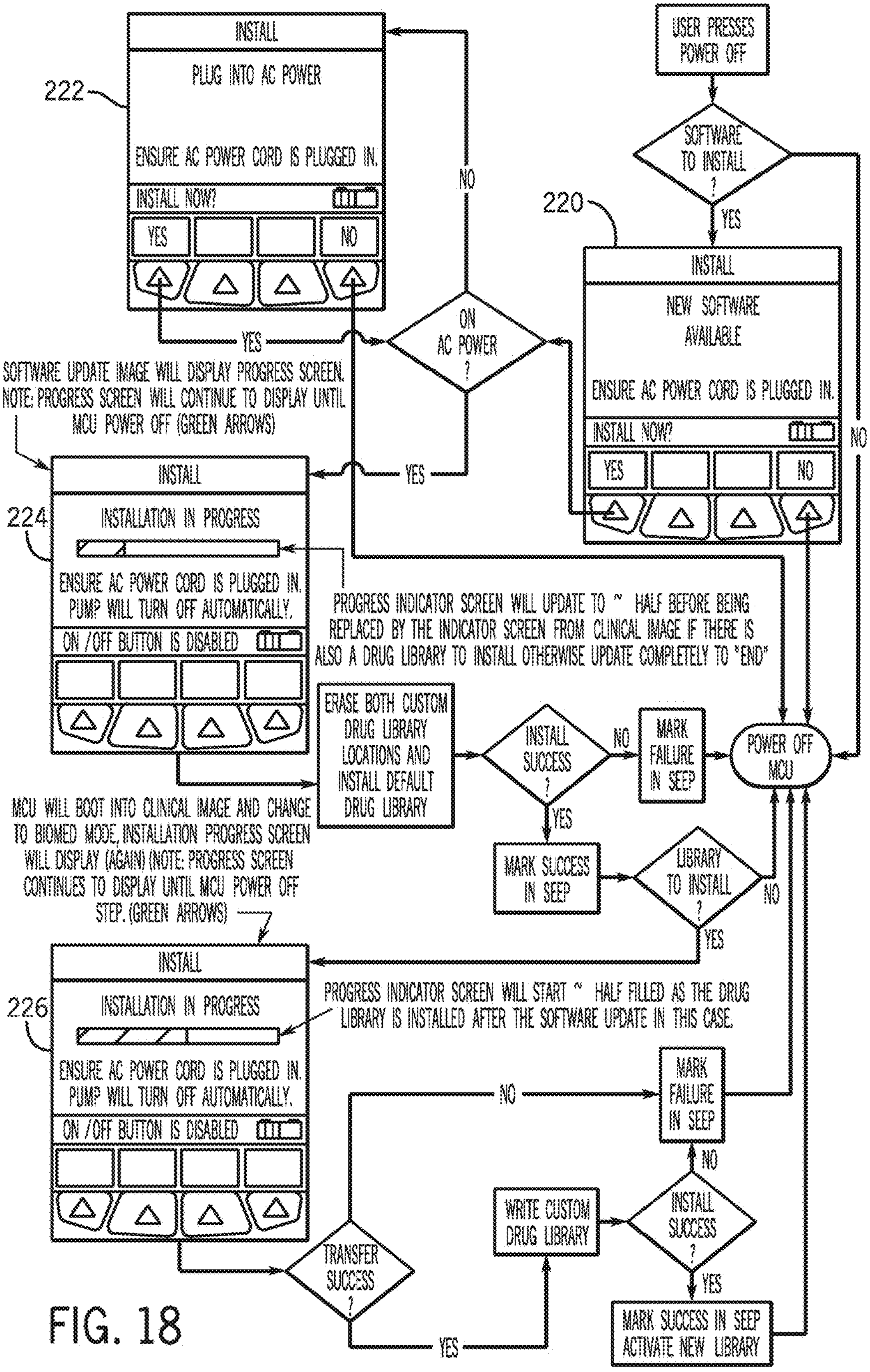

FIG. 18 illustrates an infuser screen walkthrough for a software installation process. The screenshots of FIG. 18 show the steps and screens which result in the processing for the installation process. In the case of a failure the process will repeat until successful or for three failed attempts.

When the user presses the power off button, and there is software ready to be installed, screen 220 will appear, asking the user to install the software. If the user selects "No", to MCU powers off. If the user selects "yes", the system verifies whether the infuser is plugged into AC power. If not, window 222 appears, telling to user to plug the unit into an AC power source. Alternatively, in another embodiment the installation can proceed with battery or DC power alone. Next, screen 224 appears, and the software installation begins, and both custom library locations are erased. If the software installation failed, the failure is marked in the SEEP memory, and the MCU powers off. If the software installation was successful, screen 226 appears, and the drug library installation begins. If the library installation failed, the failure is marked in the SEEP memory, and the MCU powers off. If the library transfer was successful, the custom drug library is written to memory. Next, the SEEP memory is marked as either a success or failure, and the MCU is powered off.

Figure 19:
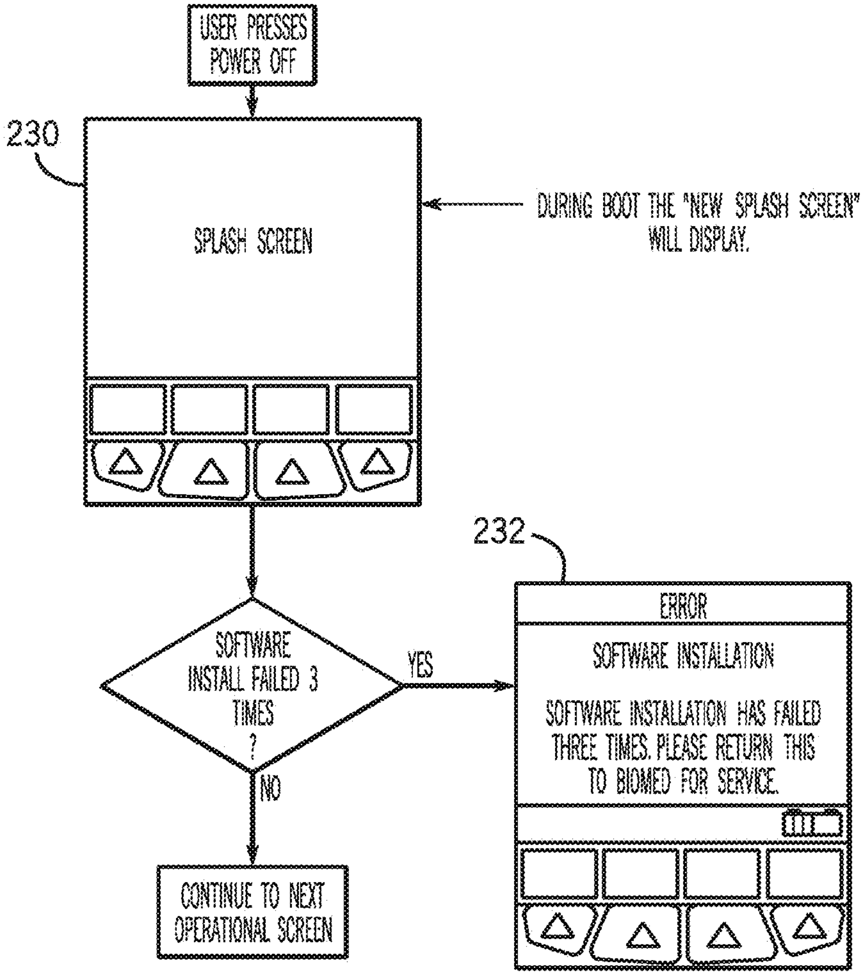

FIG. 19 illustrates an infuser screen walkthrough for a failed software installation. After a user presses the power on button, splash screen 230 appears. If the software installation has failed 3 times (in this example), screen 232 appears, instructing the user to return the infuser to the biomed center for service. If the software has not failed 3 times, the software update process can be repeated.

As described above, updates will be available to medical devices after a user goes through a selection process to selects one or more updates for one or more medical devices. In one example, a wizard-based selection mechanism is provided to allow any number of the devices to be selected for updates. The wizard can run on the server, or on a network client that communicates with the server.

Figure 20:
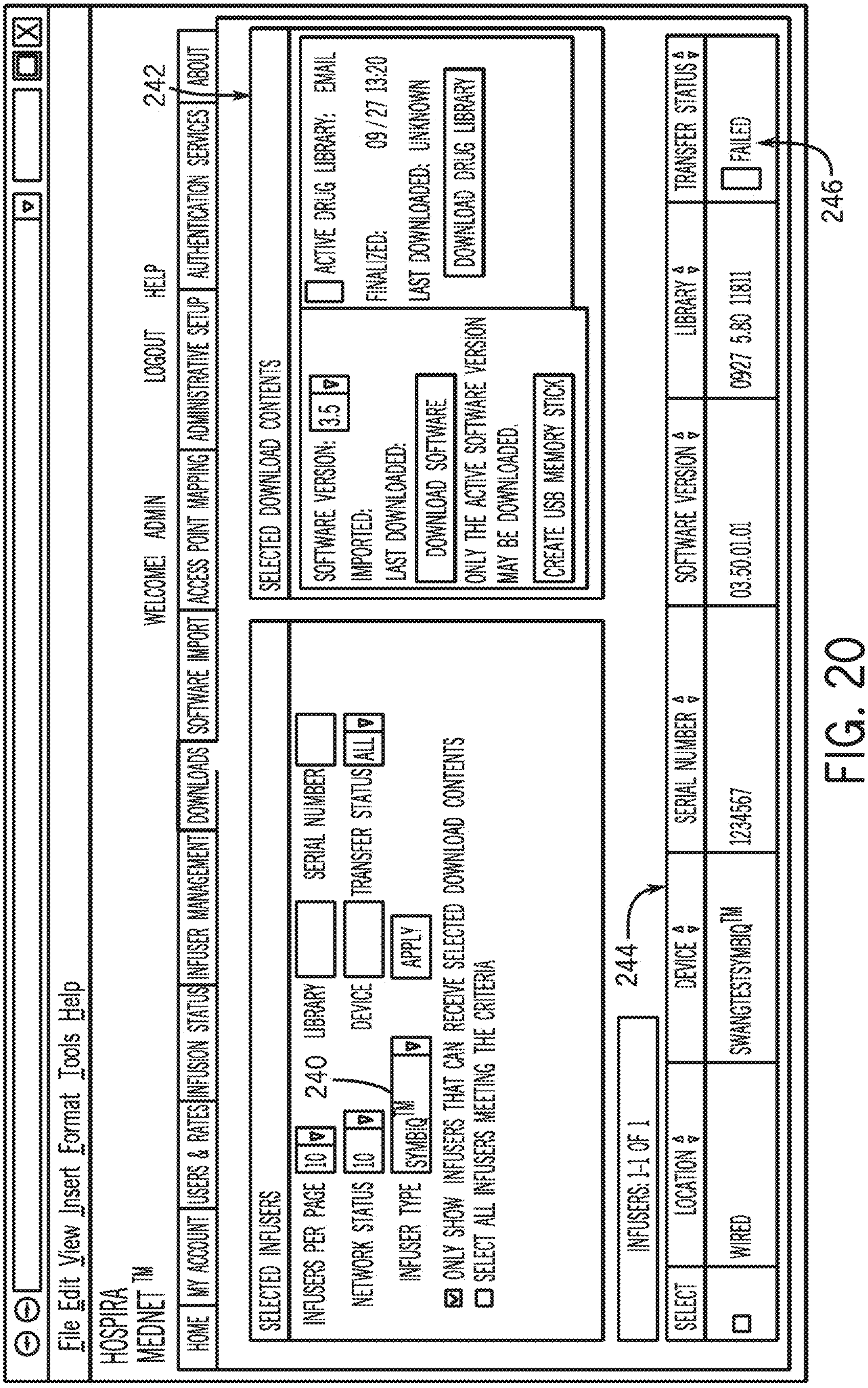
FIG. 20 is a screenshot of an exemplary selection wizard used by a user to select software and drug library updates and devices to be updated.

FIG. 20 is a screenshot of an exemplary selection wizard used by a user to select updates and devices for updates. Using the wizard, an IT technician can configure an update on the server. The wizard is flexible enough to allow for many different implementations. In this example, a type of device is selected (pull down menu 240) and the available software and configuration files are presented (box 242). The IT technician can then select the devices (displayed in table 244) to update and which files will be part of the update. The server will package the update into some number of files, implemented as JAR zip compressed files, in one example. The screen will also display the status 246 of the updates during the update process.

The update message (described above) is prepared for the devices. The update message contains a manifest or list of the files and their locations on the server. The update may be a single file on one server or can be composed of multiple files from multiple servers or locations on one server. The server will send this message to each of the selected devices informing the devices of the availability and location of the update(s).

As described above, the devices will then pull the update file(s) from the server(s) and store the update locally on the device. The device will then prompt the nurse during power off to install the update. The update will install and then the device will power down normally. A scripting interface in the update may make the updates available at a future time allowing for staged delivery of the updates to all the devices before the update is made available.

In the preceding detailed description, the disclosure is described with reference to specific exemplary embodiments thereof. Various modifications and changes may be made thereto without departing from the broader scope of the disclosure as set forth in the claims. The specification and drawings are, accordingly, to be regarded in an illustrative rather than a restrictive sense.

What is claimed is:

1. An infusion pump configured to administer medication to a patient, the infusion pump comprising:
- a display screen comprising a user interface configured to permit a user to monitor and operate the infusion pump; and
- one or more memory storage locations;
- said infusion pump configured to enable:
  - downloading, wirelessly, one or more update files for a drug library from a remote server, the drug library comprising information about drug dosing rate and volume, and the downloading being pulled by the infusion pump such that after receiving a location of the one or more update files on the remote server, the infusion pump controls the downloading of the one or more update files;
  - storing the one or more update files in the one or more memory storage locations of the infusion pump while the infusion pump is administering medication to a patient, without affecting normal operation of the infusion pump; and
  - waiting for an update time when the one or more update files can be installed, wherein the installation of the one or more update files requires receiving an acceptance of the installation from a user through the user interface.

2. The infusion pump of claim 1, wherein the installation of the one or more update files includes changing a status of the one or more memory storage locations of the one of more update files to become an active drug library memory location and changing the status of another one or more memory locations to be where a subsequent update can be stored.

3. The infusion pump of claim 1, wherein the infusion pump is further configured to enable:
- determining a state of the infusion pump, wherein the state includes at least one of administering an infusion to a patient or after receiving a power-down command for the infusion pump; and
- determining the update time based on the determined state of the infusion pump.

4. The infusion pump of claim 1, wherein the infusion pump is further configured to download one or more update files for operating software.

5. The infusion pump of claim 1, wherein the one or more update files are encrypted in such a way that the infusion pump is able to decrypt the one or more update files after the one or more update files are downloaded.

6. The infusion pump of claim 1, wherein the infusion pump is further configured to enable providing a status update for the installation to the remote server.

7. The infusion pump of claim 1, wherein the infusion pump is further configured to enable displaying a status update for the installation on the display screen.

8. The infusion pump of claim 1, wherein the installation is independently powered from an infusion subsystem.

9. An infusion pump configured to administer medication to a patient, the infusion pump comprising:

a display screen comprising a user interface configured to permit a user to monitor and operate the infusion pump; and one or more memory storage locations;

said infusion pump configured to enable:

downloading, wirelessly, one or more update files for a drug library from a remote server, the drug library comprising information about drug dosing rate and volume, and the downloading being pulled by the infusion pump such that after receiving a location of the one or more update files on the remote server, the infusion pump controls the downloading of the one or more update files;

storing the one or more update files in the one or more memory storage locations of the infusion pump while the infusion pump is administering medication to a patient, without affecting normal operation of the infusion pump; and waiting for an update time when the one or more update files can be installed, wherein the installation of the one or more update files does not require assent of the user.

10. The infusion pump of claim 9, wherein the installation of the one or more update files includes changing a status of the one or more memory storage locations of the one of more update files to become an active drug library memory location and changing the status of another one or more memory locations to be where a subsequent update can be stored.

11. The infusion pump of claim 9, wherein the infusion pump is further configured to enable:

determining a state of the infusion pump, wherein the state includes at least one of administering an infusion to a patient or after receiving a power-down command for the infusion pump; and determining the update time based on the determined state of the infusion pump.

12. The infusion pump of claim 9, wherein the one or more update files includes an update for operating software.

13. The infusion pump of claim 9, wherein the one or more update files are encrypted in such a way that the infusion pump is able to decrypt the one or more update files after the one or more update files are downloaded.

14. The infusion pump of claim 9, wherein the infusion pump is further configured to enable providing a status update for the installation to the remote server.

15. The infusion pump of claim 9, wherein the infusion pump is further configured to enable displaying a status update for the installation on the display screen.

16. The infusion pump of claim 9, wherein the installation is independently powered from an infusion subsystem.

17. An infusion pump configured to administer medication to a patient, the infusion pump comprising:

a display screen comprising a user interface configured to permit a user to monitor and operate the infusion pump; and one or more memory storage locations;

said infusion pump configured to enable:

downloading, wirelessly, one or more update files for a drug library from a remote server, the drug library comprising information about drug dosing rate and volume, and the downloading being pulled by the infusion pump such that after receiving a location of the one or more update files on the remote server, the infusion pump controls the downloading of the one or more update files;

storing the one or more update files in the one or more memory storage locations of the infusion pump while the infusion pump is administering medication to a patient, without affecting normal operation of the infusion pump; and waiting for an update time when the one or more update files can be installed when the infusion pump is powered off, with or without requiring acceptance by the user.

18. The infusion pump of claim 17, wherein said powering off the infusion pump comprises powering off an infusion subsystem, wherein the installation is independently powered to install the one or more update files while the infusion subsystem is powered off.

19. An infusion pump configured to administer medication to a patient, the infusion pump comprising:

a display screen comprising a user interface configured to permit a user to monitor and operate the infusion pump; and one or more memory storage locations;

said infusion pump configured to enable:

downloading, wirelessly, one or more update files for a drug library from a remote server, the drug library comprising information about drug dosing rate and volume, and the downloading being pulled by the infusion pump such that after receiving a location of the one or more update files on the remote server, the infusion pump controls the downloading of the one or more update files;

storing the one or more update files in the one or more memory storage locations of the infusion pump while the infusion pump is administering medication to a patient, without affecting normal operation of the infusion pump; and waiting for an update time when the one or more update files can be installed.

20. The infusion pump of claim 19, wherein the one or more update files are encrypted.

21. The infusion pump of claim 19, wherein the installation of the one or more update files includes changing a status of the one or more memory storage locations of the one of more update files to become an active drug library memory location and changing the status of another one or more memory locations to be where a subsequent update can be stored.

* * * * *